(12) United States Patent
Yasui et al.

(10) Patent No.: US 7,765,996 B2
(45) Date of Patent: Aug. 3, 2010

(54) DEVICE AND METHOD OF CONTROLLING EXHAUST GAS SENSOR TEMPERATURE, AND RECORDING MEDIUM FOR EXHAUST GAS SENSOR TEMPERATURE CONTROL PROGRAM

(75) Inventors: Yuji Yasui, Wako (JP); Yoshihisa Iwaki, Wako (JP)

(73) Assignee: Honda Giken Kogyo Kabushiki Kaisha, Minato-Ku, Tokyo (JP)

( * ) Notice: Subject to any disclaimer, the term of this patent is extended or adjusted under 35 U.S.C. 154(b) by 0 days.

(21) Appl. No.: 12/292,612

(22) Filed: Nov. 21, 2008

(65) Prior Publication Data

US 2009/0077953 A1 Mar. 26, 2009

Related U.S. Application Data

(62) Division of application No. 10/517,139, filed on Dec. 7, 2004, now Pat. No. 7,490,596.

(51) Int. Cl.
*F02D 41/14* (2006.01)
(52) U.S. Cl. ........................... 123/697; 701/109
(58) Field of Classification Search ............... 123/672, 123/674, 676, 679, 687, 697; 701/105, 101–103, 701/109; 204/425, 426; 369/283; 60/274, 60/276

See application file for complete search history.

(56) References Cited

U.S. PATENT DOCUMENTS

| | | | |
|---|---|---|---|
| 5,214,267 A | 5/1993 | Hoshi et al. |
| 5,787,866 A | 8/1998 | Sugiyama et al. |
| 5,935,399 A | 8/1999 | Tanaka et al. |
| 6,304,813 B1 | 10/2001 | Ikeda et al. |
| 6,673,223 B2 | 1/2004 | Kunimoto et al. |
| 6,823,839 B2 | 11/2004 | Yasui et al. |

FOREIGN PATENT DOCUMENTS

| | | |
|---|---|---|
| DE | 19629552 C1 | 12/1997 |
| JP | 60-72561 | 5/1985 |
| JP | 61-34469 | 3/1986 |
| JP | 01-172745 | 7/1989 |
| JP | 4-369471 | 12/1992 |
| JP | 07-167830 | 7/1995 |
| JP | 08-278279 | 10/1996 |
| JP | 10-010074 | 1/1998 |
| JP | 11-324767 | 11/1999 |

(Continued)

*Primary Examiner*—Willis R. Wolfe, Jr.
*Assistant Examiner*—Johnny H Hoang
(74) *Attorney, Agent, or Firm*—Squire, Sanders & Dempsey L.L.P.

(57) ABSTRACT

A control input (DUT) for controlling a heater (13) which heats an active element (10) of an exhaust gas sensor (8) includes at least one of another component depending on the difference between temperature data of the active element (10) and a target temperature, a component depending on the target temperature, and a component depending on the temperature data of the active element (10). The control input is determined by an optimum control algorithm. A component depending on the temperature of an exhaust gas and the component depending on the target temperature are determined based on a predictive control algorithm. The temperature of the active element (10) of the exhaust gas sensor (8) is thus controlled stably at a desired temperature.

12 Claims, 13 Drawing Sheets

FOREIGN PATENT DOCUMENTS

| | | |
|---|---|---|
| JP | 2000-249677 | 9/2000 |
| JP | 2000-292407 | 10/2000 |
| JP | 2000-304721 | 11/2000 |
| JP | 2001-324469 | 11/2001 |
| JP | 2003-065999 | 3/2003 |
| JP | 2003-097323 | 4/2003 |

DEVICE AND METHOD OF CONTROLLING EXHAUST GAS SENSOR TEMPERATURE, AND RECORDING MEDIUM FOR EXHAUST GAS SENSOR TEMPERATURE CONTROL PROGRAM

TECHNICAL FIELD

The present invention relates to an apparatus for and a method of controlling the temperature of an exhaust gas sensor disposed in the exhaust passage of an internal combustion engine, and a recording medium storing a program for controlling the temperature of such an exhaust gas sensor.

BACKGROUND ART

Exhaust gas sensors are often disposed in the exhaust passages of internal combustion engines for detecting a physical quantity as to an exhaust gas component state, such as an exhaust gas component concentration, for the purpose of controlling the operation of the internal combustion engine or monitoring the status of an exhaust gas purifying system. Specifically, the exhaust gas sensor is disposed at a certain location in the exhaust gas passage and has an element sensitive to an exhaust gas component state to be detected, the element being positioned for contact with an exhaust gas flowing through the exhaust passage. For example, an air-fuel ratio sensor such as an $O_2$ sensor or the like is disposed as an exhaust gas sensor upstream or downstream of an exhaust gas purifying catalyst disposed in the exhaust passage for the purpose of controlling the air-fuel ratio of the internal combustion engine in order to keep well the purifying ability of the catalyst.

Some air-fuel ratio sensors have a built-in heater for heating the active element thereof for increasing the temperature of the element and activating the element to enable the element to perform its essential functions and also removing foreign matter deposited on the element. For example, an air-fuel ratio sensor such as an $O_2$ sensor or the like usually has an electric heater for heating the active element thereof. After the internal combustion engine has started to operate, the electric heater is energized to increase the temperature of the active element of the $O_2$ sensor to activate the active element and keep the active element active.

As shown in FIG. 3 of the accompanying drawings, the $O_2$ sensor produces an output voltage Vout which changes with a large gradient with respect to a change in the air-fuel ratio of an exhaust gas, i.e., which is highly sensitive to a change in the air-fuel ratio, only in a small range $\Delta$ (near a stoichiometric air-fuel ratio) of values of the air-fuel ratio that is represented by an oxygen concentration in the exhaust gas to which the active element is sensitive. A change in the output voltage Vout of the $O_2$ sensor, i.e., a gradient of the output voltage Vout with respect to the air-fuel ratio, is smaller in air-fuel ratio ranges that are richer and leaner than the highly sensitive range $\Delta$. The output characteristics of the $O_2$ sensor, i.e., the gradient of the highly sensitive range $\Delta$, etc., vary depending on the temperature of the active element. When the air-fuel ratio is to be controlled using the output voltage from the $O_2$ sensor, therefore, it is desirable to keep the output characteristics of the $O_2$ sensor in a desired range as much as possible and hence to keep the temperature of the active element of the $O_2$ sensor in a desired temperature range as stably as possible for better air-fuel ratio control.

Not only $O_2$ sensors but also many exhaust gas sensors have their output characteristics affected by the temperature of the active element. If the internal combustion engine is to be controlled using the output signal from the $O_2$ sensor, then it is preferable to keep the temperature of the active element of the exhaust gas sensor in a desired temperature range as stably as possible for better engine control. When the active element of the exhaust gas sensor is heated to clean the active element, it is also preferable to keep the temperature of the active element of the exhaust gas sensor in a desired temperature range for a better cleaning effect.

As disclosed in Japanese laid-open patent publication No. 2000-304721 by the applicant of the present application, it is known to estimate the temperature of the active element of an exhaust gas sensor (an air-fuel ratio sensor in the publication) and control the energization of a heater (an electric heater) based on the estimated temperature for thereby keep the temperature of the active element in a desired temperature range to obtain appropriate output characteristics from the exhaust gas sensor. According to the disclosed arrangement, the resistance of the heater is recognized from detected values of a current flowing through the heater and a voltage applied across the heater, and the temperature of the active element is estimated based on the detected resistance of the heater.

According to the disclosure of the above publication, however, since a duty cycle which determines the electric power to be supplied to the heater is uniquely determined by a table from an estimated value of the temperature of the active element of the exhaust gas sensor, it is difficult to control the temperature of the active element of the exhaust gas sensor stably at a desired temperature because of a change in the temperature of the exhaust gas, an ambient air temperature, etc. Furthermore, if the temperature of the active element of the exhaust gas sensor is low, then in order to keep the duty cycle of the heater at a certain maximum level, the heater tends to consume more electric power than required and the actual temperatures of the heater and the active element are liable to be excessively high, causing damage to the heater and the active element.

The present invention has been made in view of the above background. It is an object of the present invention to provide an apparatus for and a method of controlling the temperature of the active element of an exhaust gas sensor stably at a desired temperature. Another object of the present invention is to provide a recording medium storing a temperature control program for controlling the temperature of the active element of an exhaust gas sensor stably at a desired temperature.

DISCLOSURE OF THE INVENTION

An apparatus for controlling the temperature of an exhaust gas sensor according to the present invention is an apparatus for controlling the temperature of an exhaust gas sensor disposed in an exhaust passage of an internal combustion engine and having an active element for contacting an exhaust gas flowing through the exhaust passage and a heater for heating the active element. To achieve the above object, according to a first aspect of the present invention, an apparatus for controlling the temperature of an exhaust gas sensor is characterized by comprising means for sequentially acquiring element temperature data representing the temperature of the active element, means for sequentially acquiring heater temperature data representing the temperature of the heater, and heater control means for sequentially generating a control input which defines an amount of heat generating energy supplied to the heater so as to equalize the temperature of the active element represented by the element temperature data to a predetermined target temperature, and controlling the heater depending on the control input, and characterized in that the control input generated by the heater control means includes at least an input component depending on the difference between the temperature of the active element represented by the element temperature data and the target temperature and an input component depending on the temperature of the heater represented by the heater temperature data.

Similarly, a method of controlling the temperature of an exhaust gas sensor according to the present invention is a method of controlling the temperature of an exhaust gas sensor disposed in an exhaust passage of an internal combustion engine and having an active element for contacting an exhaust gas flowing through the exhaust passage and a heater for heating the active element. According to the first aspect of the present invention, a method of controlling the temperature of an exhaust gas sensor is characterized by comprising the steps of sequentially acquiring element temperature data representing the temperature of the active element and heater temperature data representing the temperature of the heater, sequentially generating a control input which defines an amount of heat generating energy supplied to the heater so as to equalize the temperature of the active element represented by the element temperature data to a predetermined target temperature, and controlling the heater depending on the control input, and characterized in that when the control input is generated, the control input is generated so as to include at least an input component depending on the difference between the temperature of the active element represented by the element temperature data and the target temperature and an input component depending on the temperature of the heater represented by the heater temperature data.

Furthermore, a recording medium storing a temperature control program for an exhaust gas sensor according to the present invention is a recording medium readable by a computer and storing a temperature control program for enabling the computer to perform a process of controlling the temperature o an active element of an exhaust gas sensor disposed in an exhaust passage of an internal combustion engine and having the active element for contacting an exhaust gas flowing through the exhaust passage and a heater for heating the active element. According to the first aspect of the present invention, a recording medium storing a temperature control program for an exhaust gas sensor is characterized in that the temperature control program includes a program for enabling the computer to perform a process of sequentially acquiring element temperature data representing the temperature of the active element and heater temperature data representing the temperature of the heater, a control input generating program for enabling the computer to perform a process of sequentially generating a control input which defines an amount of heat generating energy supplied to the heater so as to equalize the temperature of the active element represented by the element temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the active element represented by the element temperature data and the target temperature and an input component depending on the temperature of the heater represented by the heater temperature data.

According to the first aspect of the present invention, since the heater is controlled based on a control input (a manipulated variable for an object to be controlled) including an input component depending on the difference between the temperature of the active element represented by the element temperature data and the target temperature and an input component depending on the temperature of the heater represented by the heater temperature data, or stated otherwise, a control input generated by combining at least the above input components, when the temperature of the active element varies with respect to the target temperature, it is possible to converge the temperature of the active element to the target temperature while suppressing excessive variations of the control input which defines an amount of heat generating energy supplied to the heater. As a result, the temperature of the active element of the exhaust gas sensor can stably be controlled at the target temperature.

According to the first aspect of the present invention, the element temperature data representative of the temperature of the active element may directly be detected and acquired using a temperature sensor, or may be estimated and acquired based on a suitable parameter or a model. The heater temperature data representative of the temperature of the heater may also be acquired in the same manner.

The input component depending on the difference between the temperature of the active element and the target temperature in the control input may be a component proportional to the difference, a component proportional to an accumulative sum (integrated value) of values of the difference at respective times, or a sum of these components. This also applies to a second aspect, a third aspect, and a fourth aspect of the present invention which will be described later.

According to a second aspect of the present invention, an apparatus for controlling the temperature of an exhaust gas sensor is characterized by comprising means for sequentially acquiring element temperature data representing the temperature of the active element, means for sequentially acquiring exhaust gas temperature data representing the temperature of the exhaust gas, and heater control means for sequentially generating a control input which defines an amount of heat generating energy supplied to the heater so as to equalize the temperature of the active element represented by the element temperature data to a predetermined target temperature, and controlling the heater depending on the control input, and characterized in that the control input generated by the heater control means includes at least an input component depending on the difference between the temperature of the active element represented by the element temperature data and the target temperature and an input component depending on the temperature of the exhaust gas represented by the exhaust gas temperature data.

Similarly, according to the second aspect of the present invention, a method of controlling the temperature of an exhaust gas sensor is characterized by comprising the steps of sequentially acquiring element temperature data representing the temperature of the active element and exhaust gas temperature data representing the temperature of the exhaust gas, sequentially generating a control input which defines an amount of heat generating energy supplied to the heater so as to equalize the temperature of the active element represented by the element temperature data to a predetermined target temperature, and controlling the heater depending on the control input, and characterized in that when the control input is generated, the control input is generated so as to include at least an input component depending on the difference between the temperature of the active element represented by the element temperature data and the target temperature and an input component depending on the temperature of the exhaust gas represented by the exhaust gas temperature data.

Furthermore, according to the second aspect of the present invention, a recording medium storing a temperature control program for an exhaust gas sensor is characterized in that the temperature control program includes a program for enabling the computer to perform a process of sequentially acquiring element temperature data representing the temperature of the active element and exhaust gas temperature data representing the temperature of the exhaust gas, a control input generating program for enabling the computer to perform a process of sequentially generating a control input which defines an amount of heat generating energy supplied to the heater so as to equalize the temperature of the active element represented by the element temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the active element represented by the element temperature data and the target temperature and an input component depending on the temperature of the exhaust gas represented by the exhaust gas temperature data.

According to the second aspect of the present invention, since the heater is controlled based on a control input including an input component depending on the difference between the temperature of the active element represented by the element temperature data and the target temperature and an input component depending on the temperature of the exhaust gas represented by the exhaust gas temperature data, or stated otherwise, a control input generated by combining at least the above input components, it is possible to converge the temperature of the active element to the target temperature while compensating for variations of the temperature of the exhaust gas with respect to the temperature of the active element. Stated otherwise, it is possible to converge the temperature of the active element to the target temperature while suppressing variations of the temperature of the active element due to variations of the temperature of the exhaust gas. As a result, the temperature of the active element of the exhaust gas sensor can stably be controlled at the target temperature (desired temperature).

According to the second aspect of the present invention, the element temperature data representative of the temperature of the active element may directly be detected and acquired using a temperature sensor, or may be estimated and acquired based on a suitable parameter or a model, as with the first aspect. The exhaust gas temperature data representative of the temperature of the exhaust gas may also be acquired in the same manner.

According to a third aspect of the present invention, an apparatus for controlling the temperature of an exhaust gas sensor is characterized by comprising means for sequentially acquiring element temperature data representing the temperature of the active element, and heater control means for sequentially generating a control input which defines an amount of heat generating energy supplied to the heater so as to equalize the temperature of the active element represented by the element temperature data to a predetermined target temperature, and controlling the heater depending on the control input, and characterized in that the control input generated by the heater control means includes at least an input component depending on the difference between the temperature of the active element represented by the element temperature data and the target temperature and an input component depending on the target temperature.

Similarly, according to the third aspect of the present invention, a method of controlling the temperature of an exhaust gas sensor is characterized by comprising the steps of sequentially acquiring element temperature data representing the temperature of the active element, sequentially generating a control input which defines an amount of heat generating energy supplied to the heater so as to equalize the temperature of the active element represented by the element temperature data to a predetermined target temperature, and controlling the heater depending on the control input, and characterized in that when the control input is generated, the control input is generated so as to further include at least an input component depending on the difference between the temperature of the active element represented by the element temperature data and the target temperature and an input component depending on the target temperature.

Furthermore, according to the third aspect of the present invention, a recording medium storing a temperature control program for an exhaust gas sensor is characterized in that the temperature control program includes a program for enabling the computer to perform a process of sequentially acquiring element temperature data representing the temperature of the active element, a control input generating program for enabling the computer to perform a process of sequentially generating a control input which defines an amount of heat generating energy supplied to the heater so as to equalize the temperature of the active element represented by the element temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the active element represented by the element temperature data and the target temperature and an input component depending on the target temperature.

According to the third aspect of the present invention, since the heater is controlled based on a control input including an input component depending on the difference between the temperature of the active element represented by the element temperature data and the target temperature and an input component depending on the target temperature, or stated otherwise, a control input generated by combining at least the above input components, it is possible to converge the temperature of the active element quickly to the target temperature. As a result, the temperature of the active element of the exhaust gas sensor can stably be controlled at the target temperature.

According to the third aspect of the present invention, the element temperature data representative of the temperature of the active element may directly be detected and acquired using a temperature sensor, or may be estimated and acquired based on a suitable parameter or a model, as with the first aspect.

According to a fourth aspect of the present invention, an apparatus for controlling the temperature of an exhaust gas sensor is characterized by comprising means for sequentially acquiring element temperature data representing the temperature of the active element, and heater control means for sequentially generating a control input which defines an amount of heat generating energy supplied to the heater so as to equalize the temperature of the active element represented by the element temperature data to a predetermined target temperature, and controlling the heater depending on the control input, and characterized in that the control input generated by the heater control means includes at least an input component depending on the difference between the temperature of the active element represented by the element temperature data and the target temperature and an input component depending on the temperature of the active element.

Similarly, according to the fourth aspect of the present invention, a method of controlling the temperature of an exhaust gas sensor is characterized by comprising the steps of sequentially acquiring element temperature data representing the temperature of the active element, sequentially generating a control input which defines an amount of heat generating energy supplied to the heater so as to equalize the temperature of the active element represented by the element temperature data to a predetermined target temperature, and controlling the heater depending on the control input, and characterized in that when the control input is generated, the control input is generated so as to include at least an input component depending on the difference between the temperature of the active element represented by the element temperature data and the target temperature and an input component depending on the temperature of the active element.

Furthermore, according to the fourth aspect of the present invention, a recording medium storing a temperature control program for an exhaust gas sensor is characterized in that the temperature control program includes a program for enabling the computer to perform a process of sequentially acquiring element temperature data representing the temperature of the active element, a control input generating program for enabling the computer to perform a process of sequentially generating a control input which defines an amount of heat generating energy supplied to the heater so as to equalize the temperature of the active element represented by the element temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the active element represented by the element temperature data and the target temperature and an input component depending on the temperature of the active element.

According to the fourth aspect of the present invention, since the heater is controlled based on a control input including an input component depending on the difference between the temperature of the active element represented by the element temperature data and the target temperature and an input component depending on the target temperature for the active element, or stated otherwise, a control input generated by combining at least the above input components, it is possible to reduce overshooting of the temperature of the active element with respect to the target temperature, and to allow the temperature of the active element to smoothly follow the target temperature. As a result, the temperature of the active element of the exhaust gas sensor can stably be controlled at the target temperature.

According to the fourth aspect of the present invention, the element temperature data representative of the temperature of the active element may directly be detected and acquired using a temperature sensor, or may be estimated and acquired based on a suitable parameter or a model, as with the first aspect.

In the first through fourth aspects of the invention, the temperature of the active element is directly controlled at the target temperature. Generally, the temperature of the heater and the temperature of the active element are highly correlated to each other in a steady state where those temperatures are substantially constant. Therefore, when the temperature of the heater is controlled at a certain target temperature, the temperature of the active element can indirectly be controlled at a temperature corresponding to the target temperature for the heater.

In view of the foregoing, according to a fifth aspect of the present invention, an apparatus for controlling the temperature of an exhaust gas sensor is characterized by comprising means for sequentially acquiring element temperature data representing the temperature of the active element, means for sequentially acquiring heater temperature data representing the temperature of the heater, and heater control means for sequentially generating a control input which defines an amount of heat generating energy supplied to the heater so as to equalize the temperature of the heater represented by the heater temperature data to a predetermined target temperature, and controlling the heater depending on the control input, and characterized in that the control input generated by the heater control means includes at least an input component depending on the difference between the temperature of the heater represented by the heater temperature data and the target temperature, and an input component depending on the temperature of the active element represented by the element temperature data.

Similarly, according to the fifth aspect of the present invention, a method of controlling the temperature of an exhaust gas sensor is characterized by comprising the steps of sequentially acquiring element temperature data representing the temperature of the active element and heater temperature data representing the temperature of the heater, sequentially generating a control input which defines an amount of heat generating energy supplied to the heater so as to equalize the temperature of the heater represented by the heater temperature data to a predetermined target temperature, and controlling the heater depending on the control input, and characterized in that when the control input is generated, the control input is generated so as to include at least an input component depending on the difference between the temperature of the heater represented by the heater temperature data and the target temperature, and an input component depending on the temperature of the active element represented by the element temperature data.

Furthermore, according to the fifth aspect of the present invention, a recording medium storing a temperature control program for an exhaust gas sensor is characterized in that the temperature control program includes a program for enabling the computer to perform a process of sequentially acquiring element temperature data representing the temperature of the active element and heater temperature data representing the temperature of the heater, a control input generating program for enabling the computer to perform a process of sequentially generating a control input which defines an amount of heat generating energy supplied to the heater so as to equalize the temperature of the heater represented by the heater temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the heater represented by the heater temperature data and the target temperature, and an input component depending on the temperature of the active element represented by the element temperature data.

The fifth aspect of the invention corresponds to the first aspect of the invention, and provides advantages similar to those of the first aspect in relation to controlling the temperature of the heater at the target temperature. Specifically, according to the fifth aspect of the invention, since the heater is controlled based on a control input (a manipulated variable for an object to be controlled) including an input component depending on the difference between the temperature of the heater represented by the heater temperature data and the target temperature (a target temperature for the heater) and an input component depending on the temperature of the active element represented by the element temperature data, or stated otherwise, a control input generated by combining at least the above input components, when the temperature of the heater varies with respect to the target temperature, it is possible to converge the temperature of the heater to the target temperature while suppressing excessive variations of the control input. As a result, the temperature of the heater of the exhaust gas sensor can stably be controlled at the target temperature, and hence the temperature of the active element can stably be controlled at a temperature corresponding to the target temperature for the heater.

According to the fifth aspect of the present invention, the element temperature data representative of the temperature of the active element and the heater temperature data representative of the temperature of the heater may be detected and acquired by a temperature sensor, or may be estimated and acquired, as with the first aspect.

The input component depending on the difference between the temperature of the heater and the target temperature in the control input may be a component proportional to the difference, a component proportional to an accumulative sum (integrated value) of values of the difference at respective times, or a sum of these components. This also applies to a sixth aspect, a seventh aspect, and an eighth aspect of the present invention which will be described later.

According to a sixth aspect of the present invention, an apparatus for controlling the temperature of an exhaust gas sensor is characterized by comprising means for sequentially acquiring heater temperature data representing the temperature of the heater, means for sequentially acquiring exhaust gas temperature data representing the temperature of the exhaust gas, and heater control means for sequentially generating a control input which defines an amount of heat generating energy supplied to the heater so as to equalize the temperature of the heater represented by the heater temperature data to a predetermined target temperature, and controlling the heater depending on the control input, and characterized in that the control input generated by the heater control means includes at least an input component depending on the difference between the temperature of the heater represented by the heater temperature data and the target temperature, and an input component depending on the temperature of the temperature of the exhaust gas represented by the exhaust gas temperature data.

Similarly, according to the sixth aspect of the present invention, a method of controlling the temperature of an exhaust gas sensor is characterized by comprising the steps of sequentially acquiring heater temperature data representing the temperature of the heater and exhaust gas temperature data representing the temperature of the exhaust gas, sequentially generating a control input which defines an amount of heat generating energy supplied to the heater so as to equalize the temperature of the heater represented by the heater temperature data to a predetermined target temperature, and controlling the heater depending on the control input, and characterized in that when the control input is generated, the control input is generated so as to include at least an input component depending on the difference between the temperature of the heater represented by the heater temperature data and the target temperature, and an input component depending on the temperature of the temperature of the exhaust gas represented by the exhaust gas temperature data.

Furthermore, according to the sixth aspect of the present invention, a recording medium storing a temperature control program for an exhaust gas sensor is characterized in that the temperature control program includes a program for enabling the computer to perform a process of sequentially acquiring heater temperature data representing the temperature of the heater and exhaust gas temperature data representing the temperature of the exhaust gas, a control input generating program for enabling the computer to perform a process of sequentially generating a control input which defines an amount of heat generating energy supplied to the heater so as to equalize the temperature of the heater represented by the heater temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the heater represented by the heater temperature data and the target temperature and an input component depending on the temperature of the exhaust gas represented by the exhaust gas temperature data.

The sixth aspect of the invention corresponds to the second aspect of the invention, and provides advantages similar to those of the second aspect in relation to controlling the temperature of the heater at the target temperature. Specifically, according to the sixth aspect of the invention, since the heater is controlled based on a control input including an input component depending on the difference between the temperature of the heater represented by the heater temperature data and the target temperature and an input component depending on the temperature of the exhaust gas represented by the exhaust gas temperature data, or stated otherwise, a control input generated by combining at least the above input components, it is possible to converge the temperature of the heater to the target temperature while compensating for variations of the temperature of the exhaust gas with respect to the temperature of the active element and the temperature of the heater. Stated otherwise, it is possible to control the temperature of the heater to the target temperature while suppressing variations of the temperature of the heater due to variations of the temperature of the exhaust gas. As a result, the temperature of the heater of the exhaust gas sensor can stably be controlled at the target temperature, and the temperature of the active element of the exhaust gas sensor can stably be controlled at a temperature corresponding to the target temperature for the heater.

According to the sixth aspect of the present invention, the heater temperature data representative of the temperature of the heater and the exhaust gas temperature data representative of the temperature of the exhaust gas may be detected and acquired or estimated and acquired, as with the first aspect.

According to a seventh aspect of the present invention, an apparatus for controlling the temperature of an exhaust gas sensor is characterized by comprising means for sequentially acquiring heater temperature data representing the temperature of the heater, and heater control means for sequentially generating a control input which defines an amount of heat generating energy supplied to the heater so as to equalize the temperature of the heater represented by the heater temperature data to a predetermined target temperature, and controlling the heater depending on the control input, and characterized in that the control input generated by the heater control means includes at least an input component depending on the difference between the temperature of the heater represented by the heater temperature data and the target temperature and an input component depending on the target temperature.

Similarly, according to the seventh aspect of the present invention, a method of controlling the temperature of an exhaust gas sensor is characterized by comprising the steps of sequentially acquiring heater temperature data representing the temperature of the heater, sequentially generating a control input which defines an amount of heat generating energy supplied to the heater so as to equalize the temperature of the heater represented by the heater temperature data to a predetermined target temperature, and controlling the heater depending on the control input, and characterized in that when the control input is generated, the control input is generated so as to include at least an input component depending on the difference between the temperature of the heater represented by the heater temperature data and the target temperature and an input component depending on the target temperature.

Furthermore, according to the seventh aspect of the present invention, a recording medium storing a temperature control program for an exhaust gas sensor is characterized in that the temperature control program includes a program for enabling the computer to perform a process of sequentially acquiring heater temperature data representing the temperature of the heater, a control input generating program for enabling the computer to perform a process of sequentially generating a control input which defines an amount of heat generating energy supplied to the heater so as to equalize the temperature of the heater represented by the heater temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the heater represented by the heater temperature data and the target temperature and an input component depending on the target temperature.

The seventh aspect of the invention corresponds to the third aspect of the invention, and provides advantages similar to those of the third aspect in relation to controlling the temperature of the heater at the target temperature. Specifically, according to the seventh aspect of the invention, since the heater is controlled based on a control input including an input component depending on the difference between the temperature of the heater represented by the heater temperature data and the target temperature and an input component depending on the target temperature, or stated otherwise, a control input generated by combining at least the above input components, it is possible to converge the temperature of the heater quickly to the target temperature. As a result, the temperature of the heater of the exhaust gas sensor can stably be controlled at the target temperature and the temperature of the active element can stably be controlled at a temperature corresponding to the target temperature for the heater.

According to the seventh aspect of the present invention, the heater temperature data representative of the temperature of the heater may be detected by a temperature sensor and acquired or may be estimated and acquired, as with the third aspect.

According to an eighth aspect of the present invention, an apparatus for controlling the temperature of an exhaust gas sensor is characterized by comprising means for sequentially acquiring heater temperature data representing the temperature of the heater, and heater control means for sequentially generating a control input which defines an amount of heat generating energy supplied to the heater so as to equalize the temperature of the heater represented by the heater temperature data to a predetermined target temperature, and controlling the heater depending on the control input, and characterized in that the control input generated by the heater control means includes at least an input component depending on the difference between the temperature of the heater represented by the heater temperature data and the target temperature and an input component depending on the temperature of the heater.

Similarly, according to the eighth aspect of the present invention, a method of controlling the temperature of an exhaust gas sensor is characterized by comprising the steps of sequentially acquiring heater temperature data representing the temperature of the heater, sequentially generating a control input which defines an amount of heat generating energy supplied to the heater so as to equalize the temperature of the heater represented by the heater temperature data to a predetermined target temperature, and controlling the heater depending on the control input, and characterized in that when the control input is generated, the control input is generated so as to include at least an input component depending on the difference between the temperature of the heater represented by the heater temperature data and the target temperature and an input component depending on the temperature of the heater.

Furthermore, according to the eighth aspect of the present invention, a recording medium storing a temperature control program for an exhaust gas sensor is characterized in that the temperature control program includes a program for enabling the computer to perform a process of sequentially acquiring heater temperature data representing the temperature of the heater, a control input generating program for enabling the computer to perform a process of sequentially generating a control input which defines an amount of heat generating energy supplied to the heater so as to equalize the temperature of the heater represented by the heater temperature data to a predetermined target temperature, and a program for enabling the computer to perform a process of controlling the heater depending on the control input, wherein the control input generating program has an algorithm for enabling the computer to generate the control input so as to include at least an input component depending on the difference between the temperature of the heater represented by the heater temperature data and the target temperature and an input component depending on the temperature of the heater.

The eighth aspect of the invention corresponds to the fourth aspect of the invention, and provides advantages similar to those of the fourth aspect in relation to controlling the temperature of the heater at the target temperature. Specifically, according to the eighth aspect of the invention, since the heater is controlled based on a control input including an input component depending on the difference between the temperature of the heater represented by the heater temperature data and the target temperature and an input component depending on the temperature of the heater, or stated otherwise, a control input generated by combining at least the above input components, it is possible to reduce overshooting of the temperature of the heater with respect to the target temperature, and to allow the temperature of the heater to smoothly follow the target temperature. As a result, the temperature of the heater of the exhaust gas sensor can stably be controlled at the target temperature and the temperature of the active element can stably be controlled at a temperature corresponding to the target temperature for the heater.

According to the eighth aspect of the present invention, the heater temperature data representative of the temperature of the heater may directly be detected and acquired using a temperature sensor, or may be estimated and acquired based on a suitable parameter or a model, as with the fourth aspect.

It is preferable to combine two or more of the first through fourth aspects of the present invention with respect to any of the temperature control apparatus, the temperature control method, and the recording medium. If the temperature control apparatus according to the first and second aspects are combined, then the temperature control apparatus according to the first aspect is characterized by means for sequentially acquiring exhaust gas temperature data representing the temperature of the exhaust gas, wherein the control input generated by the heater control means includes an input component depending on the temperature of the exhaust gas represented by the exhaust gas temperature data. Similarly, if the temperature control methods according to the first and second aspects are combined, then the temperature control method according to the first aspect is characterized by the step of sequentially acquiring exhaust gas temperature data representing the temperature of the exhaust gas, wherein when the control input is generated, the control input is generated so as to further include an input component depending on the temperature of the exhaust gas represented by the exhaust gas temperature data. Furthermore, if the recording mediums according to the first and second aspects are combined, then the recording medium according to the first aspect is characterized in that the temperature control program further includes a program for enabling the computer to perform a process of sequentially acquiring exhaust gas temperature data representing the temperature of the exhaust gas, wherein the control input generating program has an algorithm for enabling the computer to generate the control input so as to further include an input component depending on the temperature of the exhaust gas represented by the exhaust gas temperature data.

By thus combining the first and second aspects, the advantages of those aspects are added together for controlling the temperature of the active element more stably at the target temperature.

In the temperature control apparatus according to the first aspect or the combination thereof with the temperature control apparatus according to the second aspect, the control input generated by the heater control means may include an input component depending on the target temperature, providing an invention based on the combination of the temperature control apparatus according to the first and third aspects or an invention based on the combination of the temperature control apparatus according to the first through third aspects. Similarly, in the temperature control method according to the first aspect or the combination thereof with the temperature control method according to the second aspect, when the control input is generated, the control input may be generated so as to further include an input component depending on the target temperature, providing an invention based on the combination of the temperature control methods according to the first and third aspects or an invention based on the combination of the temperature control methods according to the first through third aspects. Furthermore, in the recording medium according to the first aspect or the combination thereof with the recording medium according to the second aspect, the control input generating program may have an algorithm for enabling the computer to generate the control input so as to further include an input component depending on the target temperature, providing an invention based on the combination of the recording mediums according to the first and third aspects or an invention based on the combination of the recording mediums according to the first through third aspects.

If the first and third aspects are thus combined, the advantages of those aspects are added together for controlling the temperature of the active element more stably at the target temperature. Particularly, if the first through third aspects are combined, the advantages of those aspects are added together for appropriately increasing the stability of the temperature of the active element with respect to the target temperature.

Moreover, in the temperature control apparatus according to the first aspect or the combination thereof with the temperature control apparatus according to one or more of the second and third aspects, the control input generated by the heater control means may include an input component depending on the temperature of the active element represented by the element temperature data, providing an invention based on the combination of the temperature control apparatus according to the first and fourth aspects or an invention based on the combination thereof with the temperature control apparatus according to one or more of the second and third aspects. Similarly, in the temperature control method according to the first aspect or the combination thereof with the temperature control method according to one or more of the second and third aspects, when the control input is generated, the control input may be generated so as to further include an input component depending on the temperature of the active element represented by the element temperature data, providing an invention based on the combination of the temperature control methods according to the first and fourth aspects or an invention based on the combination thereof with the temperature control method according to one or more of the second and third aspects. Furthermore, in the recording medium according to the first aspect or the combination thereof with the recording medium according to one or more of the second and third aspects, the control input generating program may have an algorithm for enabling the computer to generate the control input so as to further include an input component depending on the temperature of the active element represented by the element temperature data, providing an invention based on the combination of the recording mediums according to the first and fourth aspects or an invention based on the combination thereof with the recording medium according to one or more of the second and third aspects.

By thus combining two or more of the first through fourth aspects, the advantages of those aspects are added together for increasing the stability of the temperature of the active element with respect to the target temperature.

In the temperature control apparatus according to the second aspect, the control input generated by the heater control means may include an input component depending on the target temperature, providing an invention based on the combination of the temperature control apparatus according to the second and third aspects. Similarly, in the temperature control method according to the second aspect, when the control input is generated, the control input may be generated so as to further include an input component depending on the target temperature, providing an invention based on the combination of the temperature control methods according to the second and third aspects. Furthermore, in the recording medium according to the second aspect, the control input generating program may have an algorithm for enabling the computer to generate the control input so as to further include an input component depending on the target temperature, providing an invention based on the combination of the recording mediums according to the second and third aspects.

With the above arrangement, the advantages of the second and third aspects are added together for controlling the temperature of the active element more stably at the target temperature.

In the temperature control apparatus according to the second aspect or the combination thereof with the temperature control apparatus according to the third aspect, the control input generated by the heater control means may include an input component depending on the temperature of the active element represented by the element temperature data, providing an invention based on the combination of the temperature control apparatus according to the second and fourth aspects or an invention based on the combination of the temperature control apparatus according to the second through fourth aspects. Similarly, in the temperature control method according to the second aspect or the combination thereof with the temperature control method according to the third aspect, when the control input is generated, the control input may be generated so as to further include an input component depending on the temperature of the active element represented by the element temperature data, providing an invention based on the combination of the temperature control methods according to the second and fourth aspects or an invention based on the combination of the temperature control methods according to the second through fourth aspects. Furthermore, in the recording medium according to the second aspect or the combination thereof with the recording medium according to the third aspect, the control input generating program may have an algorithm for enabling the computer to generate the control input so as to further include an input component depending on the temperature of the active element represented by the element temperature data, providing an invention based on the combination of the recording mediums according to the second and fourth aspects or an invention based on the combination of the recording mediums according to the second through fourth aspects.

By thus combining those aspects, the advantages of the aspects are added together for increasing the stability of the temperature of the active element with respect to the target temperature.

In the temperature control apparatus according to the third aspect, the control input generated by the heater control means may include an input component depending on the temperature of the active element represented by the element temperature data, providing an invention based on the combination of the temperature control apparatus according to the third and fourth aspects. Similarly, in the temperature control method according to the third aspect, when the control input is generated, the control input may be generated so as to further include an input component depending on the temperature of the active element represented by the element temperature data, providing an invention based on the combination of the temperature control methods according to the third and fourth aspects. Furthermore, in the recording medium according to the third aspect, the control input generating program may have an algorithm for enabling the computer to generate the control input so as to further include an input component depending on the temperature of the active element represented by the element temperature data, providing an invention based on the combination of the recording mediums according to the third and fourth aspects.

With the above combination, the advantages of the third and fourth aspects are added together for increasing the stability of the temperature of the active element with respect to the target temperature.

According to the present invention, it is preferable to combine all the first through third aspects or all the first through fourth aspects. If all the first through third aspects are combined, then the input component depending on the difference between the temperature of the active element and the target temperature should preferably comprise a component proportional to an accumulative sum (integrated value) of values of the difference at respective times and a component proportional to the difference, for example. If all the first through fourth aspects are combined, then the input component depending on the difference between the temperature of the active element and the target temperature should preferably comprise a component proportional to an accumulative sum (integrated value) of values of the difference at respective times.

The combination of the inventions according to the first through fourth aspects is also applicable to the inventions according to the fifth through eighth aspects, and two or more of the fifth through eighth aspects should preferably be combined. Specifically, if the temperature control apparatus according to the fifth and sixth aspects are combined, then the temperature control apparatus according to the fifth aspect is characterized by means for sequentially acquiring exhaust gas temperature data representing the temperature of the exhaust gas, wherein the control input generated by the heater control means includes an input component depending on the temperature of the exhaust gas represented by the exhaust gas temperature data. Similarly, if the temperature control methods according to the fifth and sixth aspects are combined, then the temperature control method according to the fifth aspect is characterized by the step of sequentially acquiring exhaust gas temperature data representing the temperature of the exhaust gas, wherein when the control input is generated, the control input is generated so as to further include an input component depending on the temperature of the exhaust gas represented by the exhaust gas temperature data. Furthermore, if the recording mediums according to the fifth and sixth aspects are combined, then the recording medium according to the fifth aspect is characterized in that the temperature control program further includes a program for enabling the computer to perform a process of sequentially acquiring exhaust gas temperature data representing the temperature of the exhaust gas, wherein the control input generating program has an algorithm for enabling the computer to generate the control input so as to further include an input component depending on the temperature of the exhaust gas represented by the exhaust gas temperature data.

By thus combining the fifth and sixth aspects, the advantages of those aspects are added together for controlling the temperature of the active element more stably at the target temperature and for controlling the temperature of the active element more stably at a temperature corresponding to the target temperature for the heater.

In the temperature control apparatus according to the fifth aspect or the combination thereof with the temperature control apparatus according to the sixth aspect, the control input generated by the heater control means may include an input component depending on the target temperature (a target value for the temperature of the heater), providing an invention based on the combination of the temperature control apparatus according to the fifth and seventh aspects or an invention based on the combination of the temperature control apparatus according to the fifth through seventh aspects. Similarly, in the temperature control method according to the fifth aspect or the combination thereof with the temperature control method according to the sixth aspect, when the control input is generated, the control input may be generated so as to further include an input component depending on the target temperature, providing an invention based on the combination of the temperature control methods according to the fifth and seventh aspects or an invention based on the combination of the temperature control methods according to the fifth through seventh aspects. Furthermore, in the recording medium according to the fifth aspect or the combination thereof with the recording medium according to the sixth aspect, the control input generating program may have an algorithm for enabling the computer to generate the control input so as to further include an input component depending on the target temperature, providing an invention based on the combination of the recording mediums according to the fifth and sixth aspects or an invention based on the combination of the recording mediums according to the fifth through seventh aspects.

If the fifth and seventh aspects are thus combined, the advantages of those aspects are added together for controlling the temperature of the heater more stably at the target temperature and for controlling the temperature of the active element more stably at a temperature corresponding to the target temperature for the heater. Particularly, if the fifth through seventh aspects are combined, the advantages of the fifth through seventh aspects are added together for appropriately increasing the stability of the temperature of the heater and the temperature of the active element.

Moreover, in the temperature control apparatus according to the fifth aspect or the combination thereof with the temperature control apparatus according to one or more of the sixth and seventh aspects, the control input generated by the heater control means may include an input component depending on the temperature of the heater represented by the heater temperature data, providing an invention based on the combination of the temperature control apparatus according to the fifth and eighth aspects or an invention based on the combination thereof with the temperature control apparatus according to one or more of the sixth and seventh aspects. Similarly, in the temperature control method according to the fifth aspect or the combination thereof with the temperature control method according to one or more of the sixth and seventh aspects, when the control input is generated, the control input may be generated so as to further include an input component depending on the temperature of the heater represented by the heater temperature data, providing an invention based on the combination of the temperature control methods according to the fifth and eighth aspects or an invention based on the combination thereof with the temperature control method according to one or more of the sixth and seventh aspects. Furthermore, in the recording medium according to the fifth aspect or the combination thereof with the recording medium according to one or more of the sixth and seventh aspects, the control input generating program may have an algorithm for enabling the computer to generate the control input so as to further include an input component depending on the temperature of the heater represented by the heater temperature data, providing an invention based on the combination of the recording mediums according to the fifth and eighth aspects or an invention based on the combination thereof with the recording medium according to one or more of the sixth and seventh aspects.

By thus combining those aspects, the advantages of the aspects are added together for increasing the stability of the temperature of the heater with respect to the target temperature and for controlling the temperature of the active element more stably at a temperature corresponding to the target temperature for the heater.

In the temperature control apparatus according to the sixth aspect, the control input generated by the heater control means may include an input component depending on the target temperature (a target value for the temperature of the heater), providing an invention based on the combination of the temperature control apparatus according to the sixth and seventh aspects. Similarly, in the temperature control method according to the sixth aspect, when the control input is generated, the control input may be generated so as to further include an input component depending on the target temperature, providing an invention based on the combination of the temperature control methods according to the sixth and seventh aspects. Furthermore, in the recording medium according to the sixth aspect, the control input generating program may have an algorithm for enabling the computer to generate the control input so as to further include an input component depending on the target temperature, providing an invention based on the combination of the recording mediums according to the sixth and seventh aspects.

With the above arrangement, the advantages of the sixth and seventh aspects are added together for controlling the temperature of the heater more stably at the target temperature and for controlling the temperature of the active element more stably at a temperature corresponding to the target temperature for the heater.

Moreover, in the temperature control apparatus according to the sixth aspect or the combination thereof with the temperature control apparatus according to the seventh aspect, the control input generated by the heater control means may include an input component depending on the temperature of the heater represented by the heater temperature data, providing an invention based on the combination of the temperature control apparatus according to the sixth and eighth aspects or an invention based on the combination thereof with the temperature control apparatus according to the sixth through eighth aspects. Similarly, in the temperature control method according to the sixth aspect or the combination thereof with the temperature control method according to the seventh aspect, when the control input is generated, the control input may be generated so as to further include an input component depending on the temperature of the heater represented by the heater temperature data, providing an invention based on the combination of the temperature control methods according to the sixth and eighth aspects or an invention based on the combination thereof with the temperature control method according to the sixth through eighth aspects. Furthermore, in the recording medium according to the sixth aspect or the combination thereof with the recording medium according to the seventh aspect, the control input generating program may have an algorithm for enabling the computer to generate the control input so as to further include an input component depending on the temperature of the heater represented by the heater temperature data, providing an invention based on the combination of the recording mediums according to the sixth and eighth aspects or an invention based on the combination thereof with the recording medium according to the sixth through eighth aspects.

By thus combining those aspects, the advantages of the aspects are added together for increasing the stability of the temperature of the heater with respect to the target temperature and for controlling the temperature of the active element more stably at a temperature corresponding to the target temperature for the heater.

Moreover, in the temperature control apparatus according to the seventh aspect, the control input generated by the heater control means may include an input component depending on the temperature of the heater represented by the heater temperature data, providing an invention based on the combination of the temperature control apparatus according to the seventh and eighth aspects. Similarly, in the temperature control method according to the seventh aspect, when the control input is generated, the control input may be generated so as to further include an input component depending on the temperature of the heater represented by the heater temperature data, providing an invention based on the combination of the temperature control methods according to the seventh and eighth aspects. Furthermore, in the recording medium according to the seventh aspect, the control input generating program may have an algorithm for enabling the computer to generate the control input so as to further include an input component depending on the temperature of the heater represented by the heater temperature data, providing an invention based on the combination of the recording mediums according to the seventh and eighth aspects.

With this combination, the advantages of the seventh and eighth aspects are added together for increasing the stability of the temperature of the heater with respect to the target temperature and for controlling the temperature of the active element more stably at a temperature corresponding to the target temperature for the heater.

It is preferable to combine all the fifth through seventh aspects or all the fifth through eighth aspects in particular. If all the fifth through seventh aspects are combined, then the input component depending on the difference between the temperature of the heater and the target temperature should preferably comprise a component proportional to an accumulative sum (integrated value) of values of the difference at respective times and a component proportional to the difference, for example. If all the fifth through eighth aspects are combined, then the input component depending on the difference between the temperature of the heater and the target temperature should preferably comprise a component proportional to an accumulative sum (integrated value) of values of the difference at respective times.

In the temperature control apparatus according to the second aspect wherein the control input includes an input component depending on the temperature of the exhaust gas or in the invention based on the combination of the temperature control apparatus according to one or more of the first, third, and fourth aspects and the temperature control apparatus according to the second aspect, the input component depending on the temperature of the exhaust gas, in the control input sequentially generated by the heater control means, comprises an input component depending on time-series data of the temperature of the exhaust gas including a present value of the temperature of the exhaust gas and a future value of the temperature of the exhaust gas after a first predetermined time, wherein the heater control means preferably generates the control input including the input component according to a predictive control algorithm. Similarly, in the temperature control method according to the second aspect wherein the control input includes an input component depending on the temperature of the exhaust gas or in the invention based on the combination of the temperature control method according to one or more of the first, third, and fourth aspects and the temperature control method according to the second aspect, the input component depending on the temperature of the exhaust gas, included in the control input, comprises an input component depending on time-series data of the temperature of the exhaust gas including a present value of the temperature of the exhaust gas and a future value of the temperature of the exhaust gas after a first predetermined time, wherein the control input including the input component is preferably generated according to a predictive control algorithm. Furthermore, in the recording medium according to the second aspect wherein the control input includes an input component depending on the temperature of the exhaust gas or in the invention based on the combination of the recording medium according to one or more of the first, third, and fourth aspects and the recording medium according to the second aspect, the input component depending on the temperature of the exhaust gas, included in the control input, comprises an input component depending on time-series data of the temperature of the exhaust gas including a present value of the temperature of the exhaust gas and a future value of the temperature of the exhaust gas after a first predetermined time, wherein the control input generating program for enabling the computer to generate the control input including the input component preferably has a predictive control algorithm.

The foregoing also applies to the invention according to the sixth aspect or the invention based on the combination of one or more of the fifth, seventh, and eighth aspects and the sixth aspect, with respect to any of the temperature control apparatus, the temperature control method, and the recording medium according to the present invention for generating a control input to equalize the temperature of the heater to the target temperature.

With the above arrangement, the input component included in the control input which depends on the temperature of the exhaust gas is an input component depending on not only the present value of the temperature of the exhaust gas, but also the time-series data of the temperature of the exhaust gas including at least the future value after the first predetermined time. Therefore, the invention according to the second aspect or an invention including the same is capable of minimizing a change of the temperature of the active element with respect to a change of the temperature of the exhaust gas. Therefore, the stability with which to control the temperature of the active element at the target temperature can effectively be increased irrespective of variations of the temperature of the exhaust gas. Similarly, the invention according to the sixth aspect or an invention including the same is capable of minimizing a change of the temperature of the heater with respect to a change of the temperature of the exhaust gas. Therefore, the stability with which to control the temperature of the heater at the target temperature can effectively be increased irrespective of variations of the temperature of the exhaust gas, and the temperature of the active element can more stably be controlled at a temperature corresponding to the target temperature for the heater. The time-series data may include not only the present value of the temperature of the exhaust gas and the future value thereof after the first predetermined time, but also a plurality of future values of the temperature of the exhaust gas from present to a time after the first predetermined time.

If the control input is generated according to the predictive control algorithm taking into account the future value of the temperature of the exhaust gas, then the future value of the temperature of the exhaust gas which is required to generate the control input may be estimated according to a suitable algorithm. However, in general, the temperature of the exhaust gas does not change appreciably abruptly. In the temperature control apparatus according to the second aspect or the sixth aspect, the heater control means may generate the control input by determining the future value of the temperature of the exhaust gas until after the first predetermined time as being equal to the present value of the temperature of the exhaust gas. Similarly, in the temperature control method according to the second aspect or the sixth aspect, the predictive control algorithm may comprise an algorithm for generating the control input by determining the future value of the temperature of the exhaust gas until after the first predetermined time as being equal to the present value of the temperature of the exhaust gas. Furthermore, in the recording medium according to the second aspect or the sixth aspect, the algorithm of the control input generating program may enable the computer to generate the control input by determining the future value of the temperature of the exhaust gas until after the first predetermined time as being equal to the present value of the temperature of the exhaust gas.

With the above arrangement, since the present value of the temperature of the exhaust gas may sequentially be grasped, the algorithm for controlling the temperature of the exhaust gas sensor, including a process of grasping the temperature of the exhaust gas (acquiring the data representing the temperature of the exhaust gas), can easily be constructed.

In the temperature control apparatus according to the third aspect wherein the control input includes an input component depending on the target temperature for the active element or in the invention based on the combination of the temperature control apparatus according to one or more of the first, second, and fourth aspects and the temperature control apparatus according to the third aspect, the input component depending on the target temperature which is sequentially generated by the heater control means comprises an input component depending on time-series data of the target temperature including a present value of the target temperature and a future value of the target temperature after a second predetermined time, wherein the heater control means preferably generates the control input including the input component according to a predictive control algorithm. Similarly, in the temperature control method according to the third aspect or in the invention based on the combination of the temperature control method according to one or more of the first, second, and fourth aspects and the temperature control method according to the third aspect, the input component depending on the target temperature, included in the control input, comprises an input component depending on time-series data of the target temperature including a present value of the target temperature and a future value of the target temperature after a second predetermined time, wherein the control input including the input component is preferably generated according to a predictive control algorithm. Furthermore, in the recording medium according to the third aspect or in the invention based on the combination of the recording medium according to one or more of the first, second, and fourth aspects and the recording medium according to the third aspect, the input component depending on the target temperature, included in the control input, comprises an input component depending on time-series data of the target temperature including a present value of the target temperature and a future value of the target temperature after a second predetermined time, wherein the control input generating program for enabling the computer to generate the control input including the input component preferably has a predictive control algorithm.

The foregoing also applies to the invention according to the seventh aspect or the invention based on the combination of one or more of the fifth, sixth, and eighth aspects and the seventh aspect, with respect to any of the temperature control apparatus, the temperature control method, and the recording medium according to the present invention for generating a control input to equalize the temperature of the heater to the target temperature.

With the above arrangement, the input component included in the control input which depends on the target temperature is an input component depending on not only the present value of the target temperature, but also the time-series data of the target temperature including at least the future value after the second predetermined time. Therefore, the invention according to the third aspect or an invention including the same is capable of preventing the temperature of the active element from overshooting the target temperature therefor when the target temperature for the active element is changed. The rate at which the temperature of the active element converges to the target temperature can be increased. As a result, the temperature of the active element can quickly and smoothly follow the target temperature. In particular, immediately after the internal combustion engine has started to operate, the temperature of the active element can quickly be converted to and stabilized at the target temperature. Therefore, immediately after the internal combustion engine has started to operate, the output characteristics of the active element can quickly be stabilized at desired characteristics. As the ability of the temperature of the active element to follow a change of the target temperature for the active element is increased, the target temperature for the active element can variably be set to a value that is suitable for the operating state of the internal combustion engine.

Similarly, the invention according to the seventh aspect or an invention including the same is capable of preventing the temperature of the heater from overshooting the target temperature therefor when the target temperature for the heater is changed. The rate at which the temperature of the heater converges to the target temperature can be increased. As a result, the temperature of the heater can quickly and smoothly follow the target temperature. In particular, immediately after the internal combustion engine has started to operate, the temperature of the heater can quickly be converted to and stabilized at the target temperature, and the temperature of the active element can quickly be converted and stabilized at a temperature corresponding to the target temperature for the heater. Therefore, immediately after the internal combustion engine has started to operate, the output characteristics of the active element can quickly be stabilized at desired characteristics. As the ability of the temperature of the heater to follow a change of the target temperature for the heater is increased, the target temperature for the heater and a desired temperature of the active element can variably be set to a value that is suitable for the operating state of the internal combustion engine.

The time-series data of the target temperature may include not only the present value of the target temperature and the future value thereof after the second predetermined time, but also a plurality of future values of the target temperature from present to a time after the second predetermined time.

In the temperature control apparatus according to the first through fourth aspects of the present invention, the heater control means preferably generates the control input according to an optimum control algorithm. Similarly, in temperature control methods according to the first through fourth aspects, the control input is preferably generated according to an optimum control algorithm. In the recording medium according to the first through fourth aspects, the algorithm of the control input generating program preferably comprises an optimum control algorithm.

With the above arrangement, according to the first through fourth aspects, it is possible to generate the control input for minimizing variations of the temperature of the active element and the control input while holding in balance the ability of the temperature of the active element to converge to the target temperature and variations of the control input (variations of the heat generating energy supplied to the heater). As a result, the temperature of the active element can more stably be controlled at the target temperature (desired temperature), and at the same time, the amount of the heat generating energy supplied to the heater can be held to a required limit.

When the control input is generated according to the optimum control algorithm in the first through fourth aspects of the present invention, it is preferable to determine in advance a model to be controlled which has, as state quantities to be controlled, the difference between the temperature of the active element and the target temperature, a change per given time of the difference (a rate of change of the difference), and a change per given time of the temperature of the heater (a rate of change of the temperature of the heater), for example, and which also has, as an input quantity, at least a change per given time of the control input (a rate of change of the control input), and to construct the optimum control algorithm based on the model to be controlled. Alternatively, it is also preferable to determine in advance a model to be controlled which has, as state quantities to be controlled, the difference between the temperature of the active element and the target temperature, a change per given time of the temperature of the active element (a rate of change of the temperature of the active element), and a change per given time of the temperature of the heater (a rate of change of the temperature of the heater), for example, and which also has, as an input quantity, at least a change per given time of the control input (a rate of change of the control input), and to construct the optimum control algorithm based on the model to be controlled. At any rate, there is determined a control input capable of minimizing an evaluating function (which is represented as an integrated value (accumulated sum) of weighted sum of the squares of the above state quantities and the square of the change per given time of the control input) of the model to be controlled. With this arrangement, since the control input can be generated in a manner to not only eliminate the difference between the temperature of the active element and the target temperature, but also suppress variations of the state quantities of the model to be controlled and the control input while keeping them in balance, the stability of the temperature of the active element with respect to the target temperature can be increased.

If the model to be controlled, which serves as a basis for the optimum control algorithm in the first through fourth aspects has, as state quantities to be controlled, the difference between the temperature of the active element and the target temperature, the change per given time of the difference, and the change per given time of the temperature of the heater, it is possible to generate the control input which includes the input component depending on the difference between the temperature of the active element and the target temperature and the input component depending on the temperature of the heater. If the model to be controlled has, as state quantities to be controlled, the difference between the temperature of the active element and the target temperature, the change per given time of the temperature of the active element, and the change per given time of the temperature of the heater, it is possible to generate the control input which includes the input component depending on the difference between the temperature of the active element and the target temperature, the input component depending on the temperature of the heater, and the input component depending on the temperature of the active element. By including, as input quantities for the model to be controlled, a change per given time of the temperature of the exhaust gas and a change per given time of the target temperature for the temperature of the active element, in addition to the change per given time of the control input, it is possible to generate the control input including the input component depending on the temperature of the exhaust gas and the input component depending on the target temperature for the active element.

In the temperature control apparatus according to the fifth through eighth aspects of the present invention, the heater control means preferably generates the control input according to an optimum control algorithm. Similarly, in temperature control methods according to the fifth through eighth aspects, the control input is preferably generated according to an optimum control algorithm. In the recording medium according to the fifth through eighth aspects, the algorithm of the control input generating program preferably comprises an optimum control algorithm.

With the above arrangement, it is possible to generate the control input for minimizing variations of the temperature of the heater and the control input while holding in balance the ability of the temperature of the heater to converge to the target temperature and variations of the control input. As a result, the temperature of the heater can more stably be controlled at the target temperature and the temperature of the active element can more stably be controlled at a temperature (desired temperature) corresponding to the target temperature for the heater. At the same time, the amount of the heat generating energy supplied to the heater can be held to a required limit.

When the control input is generated according to the optimum control algorithm in the fifth through eighth aspects of the present invention, it is preferable to determine in advance a model to be controlled which has, as state quantities to be controlled, the difference between the temperature of the heater and the target temperature, a change per given time of the difference (a rate of change of the difference), and a change per given time of the temperature of the active element (a rate of change of the temperature of the active element), for example, and which also has, as an input quantity, at least a change per given time of the control input (a rate of change of the control input), and to construct the optimum control algorithm based on the model to be controlled. Alternatively, it is also preferable to determine in advance a model to be controlled which has, as state quantities to be controlled, the difference between the temperature of the heater and the target temperature, a change per given time of the temperature of the active element (a rate of change of the temperature of the active element), and a change per given time of the temperature of the heater (a rate of change of the temperature of the heater), for example, and which also has, as an input quantity, at least a change per given time of the control input (a rate of change of the control input), and to construct the optimum control algorithm based on the model to be controlled. At any rate, there is determined a control input capable of minimizing an evaluating function of the model to be controlled. With this arrangement, since the control input can be generated in a manner to not only eliminate the difference between the temperature of the heater and the target temperature, but also suppress variations of the difference, the temperature of the active element, and the control input while keeping them in balance, the stability of the temperature of the heater with respect to the target temperature and the stability of the temperature of the active element can be increased.

If the model to be controlled, which serves as a basis for the optimum control algorithm in the fifth through eighth aspects has, as state quantities to be controlled, the difference between the temperature of the heater and the target temperature, the change per given time of the difference, and the change per given time of the temperature of the active element, it is possible to generate the control input which includes the input component depending on the difference between the temperature of the heater and the target temperature and the input component depending on the temperature of the active element. If the model to be controlled has, as state quantities to be controlled, the difference between the temperature of the heater and the target temperature, the change per given time of the temperature of the active element, and the change per given time of the temperature of the heater, it is possible to generate the control input which includes the input component depending on the difference between the temperature of the heater and the target temperature, the input component depending on the temperature of the heater, and the input component depending on the temperature of the active element. By including, as input quantities for the model to be controlled, a change per given time of the temperature of the exhaust gas and a change per given time of the target temperature for the temperature of the heater, in addition to the change per given time of the control input, it is possible to generate the control input including the input component depending on the temperature of the exhaust gas and the input component depending on the target temperature for the heater.

When the optimum control algorithm according to the first through fourth aspects of the present invention and the predictive control algorithm for the temperature of the exhaust gas or the target temperature are combined, the control input is generated according to an optimum predictive control algorithm. When the control input is generated according to an optimum predictive control algorithm, the temperature of the active element can be controlled at the target temperature with high stability while keeping in balance and suppressing variations of the state quantities of the model to be controlled, which serves as a basis for the optimum control algorithm, and the input quantity. The optimum predictive control algorithm can be constructed based on a model to be controlled which includes a change per given time of the temperature of the exhaust gas and/or a change per given time of the target temperature for the active element, in addition to the change per given time of the control input, as the input quantities of the model to be controlled which has been given by way of example with respect to the first through fourth aspects, for example.

The foregoing also applies to a combination of the optimum control algorithm according to the fifth through eighth aspects of the present invention and the predictive control algorithm for the temperature of the exhaust gas or the target temperature. In this case, the control input is generated according to an optimum predictive control algorithm. When the control input is generated according to an optimum predictive control algorithm, the temperature of the heater can be controlled at the target temperature with high stability while keeping in balance and suppressing variations of the state quantities of the model to be controlled, which serves as a basis for the optimum control algorithm, and the input quantity. The optimum predictive control algorithm in this case can be constructed based on a model to be controlled which includes a change per given time of the temperature of the exhaust gas and/or a change per given time of the target temperature, in addition to the change per given time of the control input, as the input quantities of the model to be controlled which has been given by way of example with respect to the fifth through eighth aspects, for example.

In the temperature control apparatus, the temperature control method, and the recording medium according to the present invention as described above in any of the aspects, the target temperature (a target temperature for the active element or the heater) in a period immediately after the internal combustion engine has started to operate until a third predetermined time elapses is preferably set to a temperature which is lower than the target temperature after elapse of the period immediately after the internal combustion engine has started to operate.

Specifically, if the target temperature for the active element or the heater is high immediately after the internal combustion engine has started to operate, then when water in the exhaust passage is applied to the active element of the exhaust gas sensor, the active element tends to be damaged due to thermal stresses or the like which are caused by rapid heating of the active element. According to the present invention, the target temperature for the active element or the heater immediately after the internal combustion engine has started to operate is set to a temperature which is lower than the target temperature after elapse of the period immediately after the internal combustion engine has started to operate. In this manner, the active element of the exhaust gas sensor is prevented from being damaged by thermal stresses or the like.

In the temperature control apparatus according to the present invention as described above in any of the aspects, the heater comprises an electric heater for generating heat when energized by a battery according to a pulse width control (PWM control) process, if the control input generated by the heater control means comprises a duty cycle (the ratio of a pulse duration to one period of a pulsed signal used in the pulse with control process) in the pulse width control process, the temperature control apparatus is preferably further characterized by means for correcting the duty cycle depending on the voltage of the battery. Similarly, in the temperature control method according to the present invention in any of the aspects, the heater comprises an electric heater for generating heat when energized by a battery according to a pulse width control (PWM control) process, and the control input which is generated comprises a duty cycle in the pulse width control process, the temperature control method is preferably further characterized by the step of correcting the duty cycle depending on the voltage of the battery. Furthermore, in the recording medium according to the present invention in any of the aspects, the heater comprises an electric heater for generating heat when energized by a battery according to a pulse width control (PWM control) process, and the control input which is generated by the computer according to the control input program comprises a duty cycle in the pulse width control process, wherein the temperature control program preferably further includes a program for enabling the computer to perform a process of correcting the duty cycle generated by the control input generating program depending on the voltage of the battery.

Specifically, if the voltage of the battery is substantially constant, then the duty cycle defines an amount of electric power as an amount of heat generating energy supplied to the heater. If the voltage of the battery is varied by an alternator or the like, then the amount of electric power supplied to the heater is affected by not only the duty cycle but also the voltage of the battery. Therefore, by correcting the duty cycle as the control input depending on the voltage of the battery, variations of the voltage of the battery in controlling the temperature of the active element or the heater at the target temperature can be compensated for. As a result, the temperature of the active element or the temperature of the heater can stably be controlled at the target temperature without being affected by variations of the voltage of the battery, and the stability of the temperature of the active element can be increased.

According to the present invention, the exhaust gas sensor may comprise an O2 sensor disposed downstream of a catalytic converter for purifying the exhaust gas, for example. If the air-fuel ratio of the exhaust gas is controlled to keep the output voltage of the O2 sensor at a predetermined level in order for the catalytic converter to perform its desired exhaust gas purifying capability, the temperature of the active element of the O2 sensor should preferably basically be controlled at a temperature equal to or higher than 750° C. (e.g., 800° C.) for better air-fuel ratio control. In this case, when the heater is to be controlled with a target temperature determined for the active element, the target temperature may be set to a temperature equal to or higher than 750° C. (e.g., 800° C.). When the heater is to be controlled with a target temperature determined for the heater, the target temperature may be set to a temperature equal to or higher than 850° C. (e.g., 900° C.).

Furthermore, immediately after the internal combustion engine has started to operate (in a period in which a third predetermined time (e.g., 15 seconds) elapses after the internal combustion engine has started to operate), the temperature of the active element should preferably be controlled at a temperature (e.g., 600° C.) lower than the above temperature in order to prevent the active element of the O2 sensor from being damaged. In this case, when the heater is to be controlled with a target temperature determined for the active element, the target temperature for the active element immediately after the internal combustion engine has started to operate may be set to 600° C., for example. When the heater is to be controlled with a target temperature determined for the heater, the target temperature for the heater immediately after the internal combustion engine has started to operate may be set to 700° C., for example.

BEST MODE FOR CARRYING OUT THE INVENTION

Figure 1:
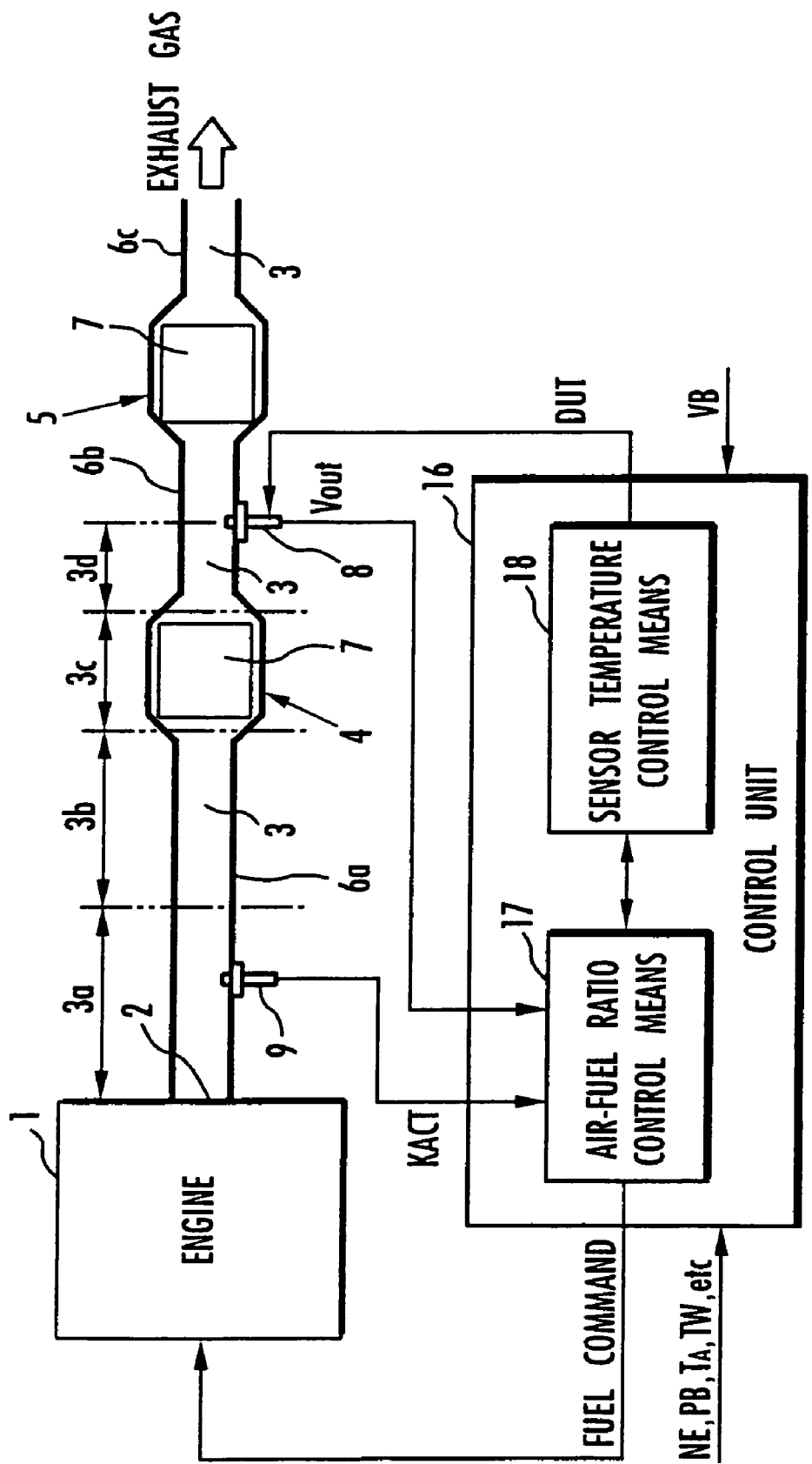
FIG. 1 is a block diagram of an apparatus according to a first embodiment of the present invention.

A first embodiment of the present invention ill be described below with reference to FIGS. 1 through 13. FIG. 1 shows in block form an overall arrangement of the apparatus according to the first embodiment of the present invention. In FIG. 1, an engine (an internal combustion engine) 1 mounted on an automobile, a hybrid vehicle, or the like combusts a mixture of fuel and air and generates an exhaust gas, which is discharged into the atmosphere through an exhaust passage 3 communicating with an exhaust port 2 of the engine 1. The exhaust passage 3 incorporates therein two catalytic converters 4, 5 disposed successively downstream for purifying the exhaust gas emitted from the engine 1 and flowing through the exhaust passage 3. The exhaust passage 3 includes a section upstream of the catalytic converter 4 (between the exhaust port 2 and the catalytic converter 4), a section between the catalytic converters 4, 5, and a section downstream of the catalytic converter 5. These sections of the exhaust passage 3 are provided by respective exhaust pipes 6a, 6b, 6c each in the form of a tubular passage-defining member.

Each of the catalytic converters 4, 5 contains a catalyst 7 (three-way catalyst in the present embodiment). The catalyst 7 has a passage-defining honeycomb structure and allows the exhaust gas to flow therethrough. Though the catalytic converters 4, 5 may be of a unitary structure with two catalytic beds, each comprising a three-way catalyst, disposed respectively in upstream and downstream regions thereof.

In the present embodiment, the air-fuel ratio in the exhaust gas emitted from the engine 1 is controlled in order for the upstream catalytic converter 4, in particular, to have a good exhaust gas purifying capability (the ability of the catalytic converter 4 to purify CO, HC, and NOx). For controlling the air-fuel ratio in the exhaust gas, an O2 sensor 8 is mounted on the exhaust passage 3 between the catalytic converters 4, 5, i.e., on the exhaust passage defined by the exhaust pipe 6b, and a wide-range air-fuel ratio sensor 9 is mounted on the exhaust passage 3 upstream of the catalytic converter 4, i.e., on the exhaust passage defined by the exhaust pipe 6a. When the catalytic converters 4, 5 take a unitary structure with two catalytic beds, the O2 sensor 8 may be mounted between the upstream catalytic bed and the downstream catalytic bed.

Figure 2:
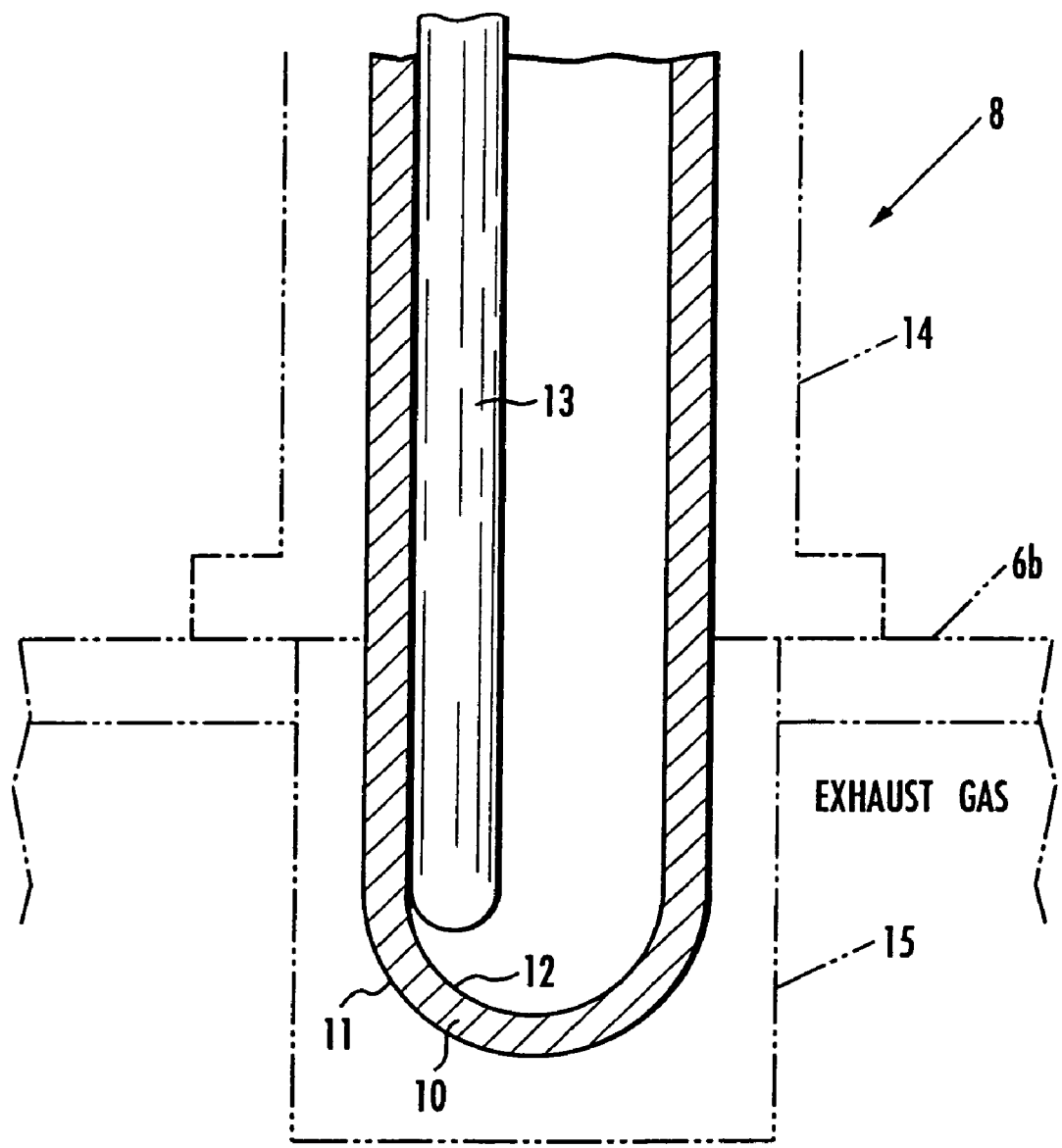
FIG. 2 is a fragmentary cross-sectional view showing a structure of an O2 sensor (exhaust gas sensor) in the apparatus shown in FIG. 1.

The O2 sensor 8 corresponds to an exhaust gas sensor according to the present invention. Basic structural details and characteristics of the O2 sensor 8 will be described below. As shown in FIG. 2, the O2 sensor 8 has an active element 10 (sensitive element) in the form of a hollow bottomed cylinder made primarily of a solid electrolyte permeable to oxygen ions, e.g., stabilized zirconia ($ZrO_2+Y_2O_3$). The active element 10 has outer and inner surfaces coated with porous platinum electrodes 11, 12, respectively. The O2 sensor 8 also has a rod-shaped ceramic heater 13 inserted as an electric heater into the active element 10 for heating the active element 10 for activation and controlling the temperature of the active element 10. The active element 10 is filled with air containing oxygen at a constant concentration, i.e., under a constant partial pressure, in a space around the ceramic heater 13. The O2 sensor 8 is placed in a sensor casing 14 mounted on the exhaust pipe 6b such that the tip end of the active element 10 has its outer surface positioned in contact with the exhaust gas flowing in the exhaust pipe 6b.

As shown in FIG. 2, the tip end of the active element 10 is covered with a tubular protector 15 which protects the active element 10 against the impingement of foreign matter thereon. The tip end of the active element 10 which is positioned in the exhaust pipe 6b contacts the exhaust gas through a plurality of holes (not shown) defined in the protector 15.

The O2 sensor 8 thus constructed operates as follows: An electromotive force depending on the concentration of oxygen in the exhaust gas is generated between the platinum electrodes 11, 12 based on the difference between the concentration of oxygen in the exhaust gas which is brought into contact with the outer surface of the tip end of the active element 10 and the concentration of oxygen in the air in the active element 10. The generated electromotive force is amplified by an amplifier (not shown), and then produced as the output voltage Vout from the O2 sensor 8.

Figure 3:
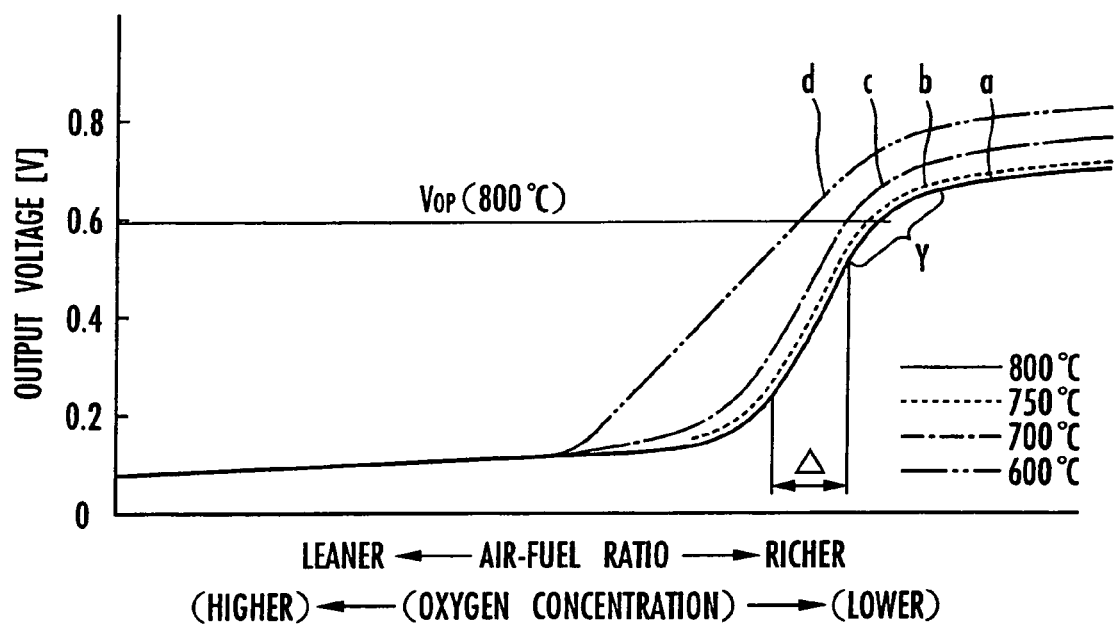
FIG. 3 is a graph illustrative of the output characteristics of the O2 sensor shown in FIG. 2.

The output voltage Vout of the O2 sensor 8 has characteristics (output characteristics) with respect to the concentration of oxygen in the exhaust gas or the air-fuel ratio in the exhaust gas which is recognized from the concentration of oxygen, as represented by a solid-line curve "a" (so-called "Z curve") in FIG. 3. The solid-line curve "a" in FIG. 3 represents the output characteristics of the O2 sensor 8 when the temperature of the active element 10 is 800° C. The relationship between the temperature of the active element 10 and the output characteristics of the O2 sensor 8 will be described later on.

As indicated by the curve "a" in FIG. 3, the output characteristics of the O2 sensor 8 are generally of such a nature that the output voltage Vout changes substantially linearly with high sensitivity with respect to the air-fuel ratio of the exhaust gas only when the air-fuel ratio represented by the concentration of oxygen in the exhaust gas is present in a narrow air-fuel ratio range Δ near a stoichiometric air-fuel ratio. In the air-fuel ratio range Δ (hereinafter referred to as "high-sensitivity air-fuel ratio range Δ"), the gradient of a change in the output voltage Vout with respect to a change in the air-fuel ratio, i.e., the gradient of the curve of the output characteristics of the O2 sensor 8, is large. In an air-fuel ratio range richer than the high-sensitivity air-fuel ratio range Δ and an air-fuel ratio range leaner than the high-sensitivity air-fuel ratio range Δ, the gradient of a change in the output voltage Vout with respect to a change in the air-fuel ratio, i.e., the gradient of the curve of the output characteristics of the O2 sensor 8, is smaller.

The wide-range air-fuel ratio sensor 9, which will not be described in detail below, comprises an air-fuel ratio sensor disclosed in Japanese laid-open patent publication No. 4-369471 by the applicant of the present application, for example. The wide-range air-fuel ratio sensor 9 is a sensor for generating an output voltage KACT which changes linearly with respect to the air-fuel ratio in the exhaust gas in the air-fuel ratio wider in range than the O2 sensor 8. The output voltage Vout of the O2 sensor 8 and the output voltage KACT of the wide-range air-fuel ratio sensor 9 will hereinafter be referred to as "output Vout" and "output KACT", respectively.

The apparatus according to the present embodiment also has a control unit 16 for controlling the air-fuel ratio in the exhaust gas and controlling the temperature of the active element 10 of the O2 sensor 8. The control unit 16 comprises a microcomputer including a CPU, a RAM, and a ROM (not shown). For carrying out a control process to be described later on, the control unit 16 is supplied with the outputs Vout and KACT from the O2 sensor 8 and the wide-range air-fuel ratio sensor 9, and also with data of detected values representing the rotational speed NE of the engine 1, the intake pressure PB (specifically, the absolute pressure in the intake pipe of the engine 1), the atmospheric temperature TA, the engine temperature TW (specifically, the temperature of the coolant of the engine 1), etc., from sensors (not shown) combined with the engine 1. The control unit 16 is also supplied with data of detected values representing the voltage VB (hereinafter referred to as "battery voltage VB") of a battery (not shown) as a power supply of electronic accessories including an ignition unit (not shown) of the engine 1, the control unit 16, the ceramic heater 13, etc., from a sensor (not shown). The ROM of the control unit 16 corresponds to a recording medium according to the present invention.

The control unit 16 has as its functional means an air-fuel ratio control means 17 for controlling the air-fuel ratio in the exhaust gas emitted from the engine 1, and a sensor temperature control means 18 for controlling the temperature of the active element 10 of the O2 sensor 8.

The air-fuel ratio control means 17 controls the air-fuel ratio in the exhaust gas supplied from the engine 1 to the catalytic converter 4 in order to achieve a good purifying ability (purification rate) of the catalytic converter 4 to purify CO (carbon monoxide), HC (hydrocarbon), and NOx (nitrogen oxide). When the O2 sensor 8 of the above output characteristics is disposed downstream of the catalytic converter 4, a good purifying ability of the catalytic converter 4 to purify CO, HC, and NOx can be achieved irrespective of the deteriorated state of the catalytic converter 4 by controlling the air-fuel ratio in the exhaust gas supplied to the catalytic converter 4, i.e., the air-fuel ratio in the exhaust gas upstream of the catalytic converter 4, to settle the output Vout of the O2 sensor 8 at a certain predetermined value Vop (see FIG. 3).

Specifically, the air-fuel ratio control means 17 uses the predetermined value Vop as a target value for the output Vout of the O2 sensor 8, and controls the air-fuel ratio in the exhaust gas supplied from the engine 1 to the catalytic converter 4 in order to settle and keep the output Vout of the O2 sensor 8 at the target value Vop. Such an air-fuel ratio control process is carried out by determining a target air-fuel ratio in the exhaust gas supplied to the catalytic converter 4 according to a feedback control process in order to converge the output Vout of the O2 sensor 8 to the target value Vop, and adjusting the amount of fuel to be supplied to the engine 1 according to a feedback control process in order to converge the output KACT (a detected value of the air-fuel ratio) of the wide-range air-fuel ratio sensor 9 to the target air-fuel ratio. Specific details of the air-fuel ratio control process carried by the air-fuel ratio control means 17 do not constitute an essential feature of the present invention, and will not be described below. The air-fuel ratio control process carried by the air-fuel ratio control means 17 is carried out as described in paragraphs [0071]-[0362] in the specification of Japanese laid-open patent publication No. 11-324767 or U.S. Pat. No. 6,188,953, for example.

The output characteristics of the O2 sensor 8 change depending on the temperature of the active element 10 thereof. In FIG. 3, the solid-line curve "a", a broken-line curve "b", a dot-and-dash-line curve "c", and a two-dot-and-dash-line curve "d" represent the output characteristics of the O2 sensor 8 when the active element 10 has temperatures of 800° C., 750° C., 700° C., and 600° C., respectively. As can be seen from FIG. 3, if the temperature of the active element 10 changes in a temperature range lower than 750° C., then the gradient (sensitivity) of a change in the output Vout of the O2 sensor 8 in the vicinity of the stoichiometric air-fuel ratio (the high-sensitivity air-fuel ratio range Δ) and the level of the output Vout at air-fuel ratios richer than the high-sensitivity air-fuel ratio range Δ tend to change. If the temperature of the active element 10 is 750° C. or higher, then a change in the output characteristics of the O2 sensor 8 with respect to a change in the temperature of the active element 10 is so small that the output characteristics of the O2 sensor 8 are substantially constant.

Since the output characteristics of the $O_2$ sensor 8 change depending on the temperature of the active element 10 as described above, the control properties (stability and quick response) of the air-fuel ratio control means 17 are likely to be lowered depending on the temperature of the active element 10. This is because in controlling the air-fuel ratio in the exhaust gas in order to keep the output Vout of the $O_2$ sensor 8 at the target value Vop, the output characteristics of the $O_2$ sensor 8 in the vicinity of the stoichiometric air-fuel ratio, i.e., the output characteristics of the $O_2$ sensor 8 in the high-sensitivity air-fuel ratio range Δ, are liable to greatly affect those control properties. The target value Vop for the output Vout of the O₂ sensor 8 to keep well the ability of the catalyst 7 of the catalytic converter 4 to purify the exhaust gas also changes depending on the temperature of the active element 10 in a temperature range lower than 750° C. Therefore, it is preferable to keep the temperature of the active element 10 of the O₂ sensor 8 basically at a constant level for the purpose of well controlling the air-air ratio with the air-fuel ratio control means 17, i.e., controlling the output Vout of the O₂ sensor 8 at the target value Vop, and achieving a good purifying ability of the catalytic converter 4.

If the temperature of the active element 10 of the O₂ sensor 8 is 750° C. or higher, then the output characteristics of the O₂ sensor 8 are substantially constant and stable. According to the inventors' knowledge, if the temperature of the active element 10 is kept at a temperature equal or higher than 750° C., e.g., 800° C., then the target value Vop for the output Vout of the O₂ sensor 8 to keep well the ability of the catalyst 7 of the catalytic converter 4 to purify the exhaust gas is present in an area denoted by Y on the curve "a" in FIG. 3, i.e., an inflection point Y where the gradient of the curve "a" representing the output characteristics of the O₂ sensor 8 switches from a larger value to a smaller value as the air-fuel ratio becomes richer. At this time, the air-fuel ratio can be controlled to keep the output Vout of the O₂ sensor 8 at the target value Vop. The reason for the above air-fuel fuel control appears to be that the sensitivity of the output Vout of the O₂ sensor 8 to the air-fuel ratio at the inflection point Y is neither excessively high nor small, but is appropriate.

According to the present embodiment, the sensor temperature control means 18 controls the ceramic heater 13 to keep the temperature of the active element 10 of the O2 sensor 8 at a desired temperature which is basically equal to or higher than 750° C., e.g., 800° C. A control process carried out by the sensor temperature control means 18 will be described below.

Figure 4:
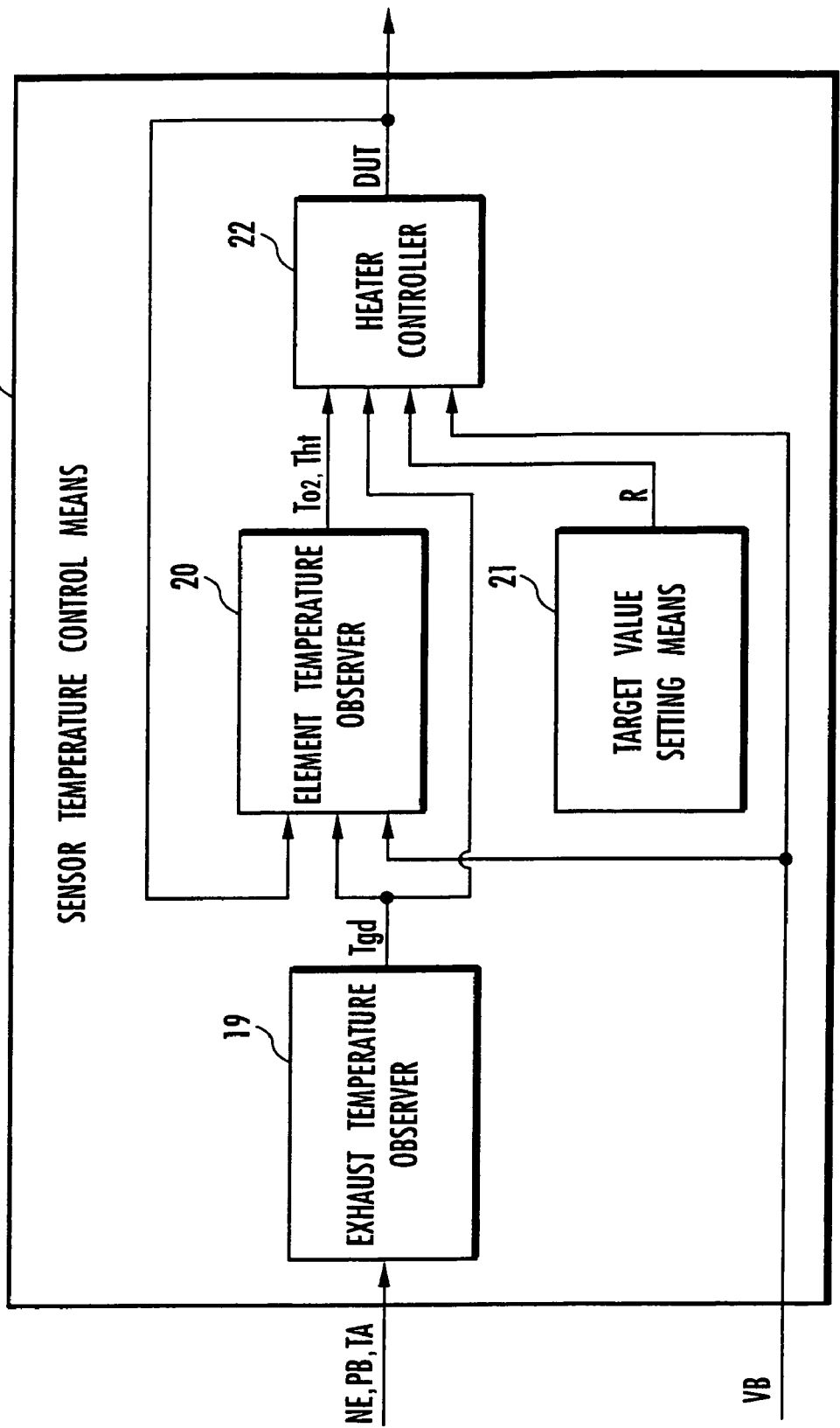
FIG. 4 is a block diagram showing a functional arrangement of a sensor temperature control means in the apparatus shown in FIG. 1.
Figure 5:
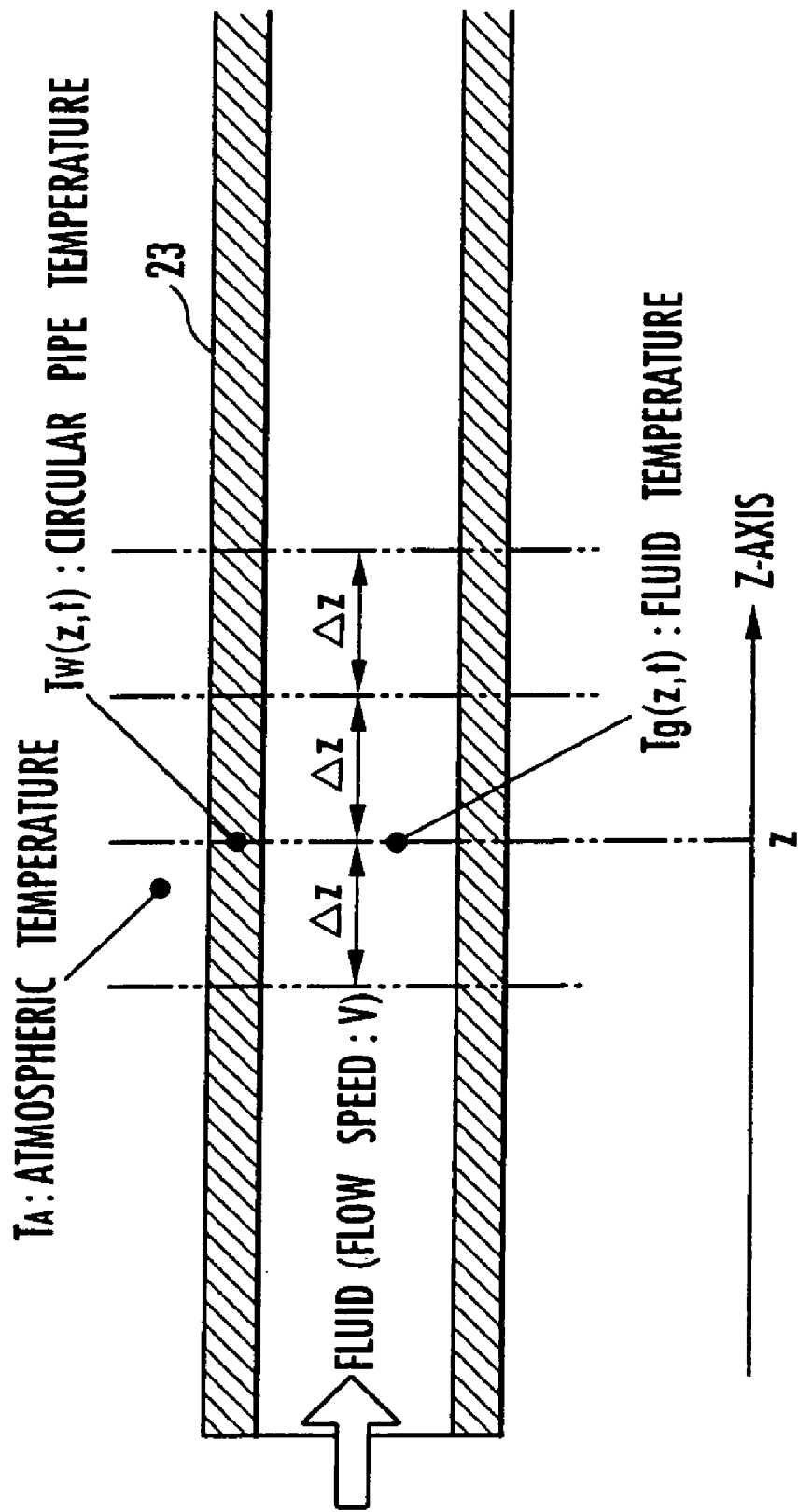
FIG. 5 is a cross-sectional view showing a processing operation of an exhaust temperature observer in the sensor temperature control means shown in FIG. 4.

As shown in FIG. 4, the sensor temperature control means 18 has as its major functions an exhaust temperature observer 19 for sequentially estimating an exhaust gas temperature Tgd in the exhaust passage 3 near the O2 sensor 8, i.e., at an intermediate portion of the exhaust pipe 6b, an element temperature observer 20 (temperature estimating means) for estimating the temperature TO2 of the active element 10 of the O2 sensor 8 and the temperature Tht of the ceramic heater 13 using the estimated value of the exhaust gas temperature Tgd, a target value setting means 21 for setting a target value R (target temperature) for the temperature of the active element 10, and a heater controller 22 (heater control means) for controlling energization of the ceramic heater 13, i.e., controlling the electric energy supplied to the ceramic heater 13, using the estimated values of the temperature TO2 of the active element 10 and the temperature Tht of the ceramic heater 13, the target value R, and the estimated value of the exhaust gas temperature Tgd. The exhaust temperature observer 19 is supplied with detected data of the rotational speed NE of the engine 1, the intake pressure PB, and the atmospheric temperature TA in order to estimate the exhaust gas temperature Tgd. The heater controller 22 and the element temperature observer 20 are supplied with the detected data of the battery voltage VB for performing their processing sequences as described later.

In the present embodiment, the ceramic heater 13 is controlled for its energization (PWM control) by giving a pulsed voltage to a heater energization circuit (not shown). The amount of electric energy supplied to the ceramic heater 13 can be controlled by adjusting the duty cycle DUT of the pulsed voltage (the ratio of the pulse duration to one period of the pulsed voltage). The heater controller 22 sequentially determines the duty cycle DUT of the pulsed voltage applied to the heater energization circuit as a control input (manipulated variable) for controlling the ceramic heater 13, and adjusts the duty cycle DUT to control the amount of electric energy supplied to the ceramic heater 13 and hence the amount of heat generated by the ceramic heater 13. The duty cycle DUT generated by the heater controller 22 is also used in the processing sequence of the element temperature observer 20.

According to the present embodiment, the portion of the exhaust passage 3 which extends from the exhaust port 2 of the engine 1 to the position where the O2 sensor 8 is located, i.e., the exhaust passage 3 upstream of the O2 sensor 8, is divided into a plurality of (four in the present embodiment) partial exhaust passageways 3a, 3b, 3c, 3d along the direction in which the exhaust passage 3 extends, i.e., the direction in which the exhaust gas flows. The exhaust temperature observer 19 estimates, in a predetermined cycle time (period), the temperature of the exhaust gas at the exhaust port 2 (the inlet of the exhaust passage 3) and the temperatures of the exhaust gas in the respective partial exhaust passageways 3a, 3b, 3c, 3d, or specifically, the temperatures of the exhaust gas in the downstream ends of the respective partial exhaust passageways 3a, 3b, 3c, 3d, successively in the downstream direction. Of the partial exhaust passageways 3a, 3b, 3c, 3d, the partial exhaust passageways 3a, 3b are two partial exhaust passageways divided from the exhaust passage 3 upstream of the catalytic converter 4, i.e., the exhaust passage defined by the exhaust pipe 6a, the partial exhaust passageway 3c is a partial exhaust passageway extending from the inlet to outlet of the catalytic converter 4, i.e., the exhaust passage defined in the catalyst 7 in the catalytic converter 4, and the partial exhaust passageway 3d is a partial exhaust passageway extending from the outlet of the catalytic converter 4 to the position where the O2 sensor 8 is located, i.e., the exhaust pipe 6b. The exhaust temperature observer 19 has its algorithm constructed as follows:

The temperature of the exhaust gas at the exhaust port 2 of the engine 1 basically depends on the rotational speed NE and the intake pressure PB of the engine 1 while the engine 1 is operating in a steady state in which the rotational speed NE and the intake pressure PB are kept constant. Therefore, the temperature of the exhaust gas at the exhaust port 2 can basically be estimated from detected values of the rotational speed NE and the intake pressure PB, which serve as parameters indicative of the operating state of the engine 1, based on a predetermined map which has been established by way of experimentation, for example. If the operating state (the rotational speed NE and the intake pressure PB) of the engine 1 varies, then the temperature of the exhaust gas at the exhaust port 2 suffers a time lag or delay in the response to the exhaust gas temperature determined by the map (hereinafter referred to as "basic exhaust gas temperature TMAP (NE,PB)").

According to the present embodiment, the exhaust temperature observer 19 determines, in a predetermined cycle time (processing period), the basic exhaust gas temperature TMAP (NE,PB) from the detected values (latest detected values) of the rotational speed NE and the intake pressure PB of the engine 1 based on the map, and thereafter sequentially estimates an exhaust gas temperature Texg at the exhaust port 2 as a value which follows, with a time lag of first order, the basic exhaust gas temperature TMAP(NE,PB) as expressed by the following equation (1):

$$Texg(k) = (1 - Ktex) \cdot Texg(k-1) + Ktex \cdot TMAP(NE, PB) \quad (1)$$

where k represents the ordinal number of a processing period of the exhaust temperature observer 19, and Ktex a coefficient (lag coefficient) predetermined by way of experimentation or the like (0<Ktex<1). In the present embodiment, the intake pressure PB of the engine 1 serves as a parameter representative of the amount of intake air introduced into the engine 1. Therefore, if a flow sensor is used for directly detecting the amount of intake air introduced into the engine 1, then the output of the flow sensor, i.e., a detected value of the amount of intake air, may be used instead of the detected value of the intake pressure PB. In the present embodiment, an initial value Texg(0) of the estimated value of the exhaust gas temperature Texg is set to the atmospheric temperature TA detected by an atmospheric temperature sensor (not shown) or the engine temperature TW (the temperature of the coolant of the engine 1) detected by an engine temperature sensor (not shown) when the engine 1 has started to operate (upon an engine startup), as described later.

Using the estimated value of the exhaust gas temperature Texg at the exhaust port 2, the temperatures of the exhaust gas in the respective partial exhaust passageways 3a, 3b, 3c, 3d are estimated as described below. For illustrative purpose, a general heat transfer that occurs when a fluid flows through a circular tube 23 (see FIG. 5) which extends in the direction of a Z-axis in the atmosphere while exchanging heat with the tube wall of the circular tube 23 will be described below. It is assumed that the fluid temperature Tg and the temperature Tw of the tube wall (hereinafter referred to as "circular tube temperature Tw") are functions Tg(t,z), Tw(t,z) of the time t and the position z in the direction of the Z-axis, the thermal conductivity of the tube wall of the circular tube 23 is infinite in the radial direction and nil in the direction of the Z-axis. It is also assumed that the heat transfer between the fluid and the tube wall of the circular tube 23 and the heat transfer between the tube wall of the circular tube 23 and the external atmosphere are proportional to their temperature differences according to the Newton law of cooling. At this time, the following equations (2-1), (2-2) are satisfied:

$$Sg \cdot \rho g \cdot Cg \cdot \left(\frac{\partial Tg}{\partial t} + V \cdot \frac{\partial Tg}{\partial z}\right) = \alpha 1 \cdot U \cdot (Tw - Tg) \quad (2\text{-}1)$$

$$Sw \cdot \rho w \cdot Cw \cdot \frac{\partial Tw}{\partial t} = \alpha 1 \cdot U \cdot (Tg - Tw) + \alpha 2 \cdot U \cdot (T_A - Tw) \quad (2\text{-}2)$$

where $S_g$, $\rho_g$, $C_g$ represent the density and specific heat of the fluid and the cross-sectional area of the fluid passage, respectively, $S_w$, $\rho_w$, $C_w$ the density, specific heat, and cross-sectional area of the tube wall of the circular tube 23, respectively, V the speed of the fluid flowing through the circular tube 23, $T_A$ the atmospheric temperature outside of the circular tube 23, U the inner circumferential length of the circular tube 23, $\alpha_1$ the heat transfer coefficient between the fluid and the tube wall of the circular tube 23, and $\alpha_2$ the heat transfer coefficient between the tube wall of the circular tube 23 and the atmosphere. It is assumed that the atmospheric temperature $T_A$ is kept constant around the circular tube 23.

The above equations (2-1), (2-2) are modified into the following equations (3-1), (3-2):

$$\frac{\partial Tg}{\partial t} = -V \cdot \frac{\partial Tg}{\partial z} + a \cdot (Tw - Tg) \quad (3\text{-}1)$$

-continued $$\frac{\partial Tw}{\partial t} = b \cdot (Tg - Tw) + c \cdot (T_A - Tw) \quad (3\text{-}2)$$

where a, b, c represent constants, $a = \alpha_1 \cdot U/(S_g \cdot \rho_g \cdot C_g)$, $b = \alpha_1 \cdot U/(S_w \cdot \rho_w \cdot C_w)$, $c = \alpha_2 \cdot U/(S_w \cdot \rho_w \cdot C_w)$.

The first term on the right side of the equation (3-1) is a shifting flow term representing a time-dependent rate of change of the fluid temperature Tg (a change in the temperature per unit time) depending on the temperature gradient in the flowing direction of the fluid and the speed of the fluid in a position z. The second term on the right side of the equation (3-1) is a heat transfer term representing a time-dependent rate of change of the fluid temperature Tg (a change in the temperature per unit time) depending on the difference between the fluid temperature Tg and the circular tube temperature Tw in the position z, i.e., a time-dependent rate of change of the fluid temperature Tg which is caused by the heat transfer between the fluid and the tube wall of the circular tube 23. Therefore, the equation (3-1) indicates that the time-dependent rate $\partial Tg/\partial t$ of change of the fluid temperature Tg in the position z depends on the temperature change component of the shifting flow term and the temperature change component of the heat transfer term, i.e., the sum of those temperature change components.

The first term on the right side of the equation (3-2) is a heat transfer term representing a time-dependent rate of change of the circular tube temperature Tw (a change in the temperature per unit time) depending on the difference between the circular tube temperature Tw and the fluid temperature Tg in the position z, i.e., a time-dependent rate of change of the circular tube temperature Tw which is caused by the heat transfer between the fluid and the tube wall of the circular tube 23 in the position z. The second term on the right side of the equation (3-2) is a heat radiation term representing a time-dependent rate of change of the circular tube temperature Tw (a change in the temperature per unit time) depending on the difference between the circular tube temperature Tw and the atmospheric temperature TA outside of the circular tube 23 in the position z, i.e., a time-dependent rate of change of the circular tube temperature Tw depending on the heat radiation from the tube wall of the circular tube 23 into the atmosphere in the position z. The equation (3-2) indicates that the time-dependent rate $\partial Tw/\partial t$ of change of the circular tube temperature Tw in the position z depends on the temperature change component of the heat transfer term and the temperature change component of the heat radiation term, i.e., the sum of those temperature change components.

According to the calculus of finite differences, the equations (3-1), (3-2) can be rewritten into the following equations (4-1), (4-2):

$$Tg(t + \Delta t, z) = Tg(t, z) - \frac{V \cdot \Delta t}{\Delta z} \cdot (Tg(t, z) - Tg(t, z - \Delta z)) + a \cdot \Delta t \cdot (Tw(t, z) - Tg(t, z)) \quad (4\text{-}1)$$

$$Tw(t + \Delta t, z) = Tw(t, z) + b \cdot \Delta t \cdot (Tg(t, z) - Tw(t, z)) + c \cdot \Delta t \cdot (T_A - Tw(t, z)) \quad (4\text{-}2)$$

The above equations (4-1), (4-2) indicate that if the fluid temperature Tg(t,z) and the circular tube temperature Tw(t,z) in the position z at the time t, and the fluid temperature Tg(t,z−Δz) in a position z−Δz which precedes the position z (upstream thereof) at the time t are known, then the fluid temperature Tg(t+Δt,z) and the circular tube temperature Tw(t+Δt,z) in the position z at a next time t+Δt can be determined, and that the fluid temperatures Tg and the circular tube temperatures Tw in successive positions z+Δz, z+2Δz, . . . can be determined by solving the equations (4-1), (4-2) simultaneously in sequence for those positions. Specifically, if initial values of the fluid temperature Tg and the circular tube temperature Tw (initial values at t=0) are given in the positions z, z+Δz, z+2Δz, . . . and the fluid temperature Tg(t,0) at an origin (e.g., the inlet of the circular tube 23) in the direction of the Z-axis of the circular tube 23 is given (it is assumed that z·Δz=0), then the fluid temperatures Tg and the circular tube temperatures Tw in successive positions z, z+Δz, z+2Δz, . . . at successive times t, t+Δt, t+2 Δt, . . . can be calculated.

The fluid temperature Tg(t,z) in the position z can be calculated by cumulatively adding (integrating), to the initial value Tg(0,z), the temperature change component depending on the fluid speed V and the temperature gradient in the position z (the temperature change component represented by the second term of the equation (4-1)) and the temperature change component depending on the difference between the fluid temperature Tg and the circular tube temperature Tw in the position z (the temperature change component represented by the third term of the equation (4-1)), at each given time interval. The fluid temperatures in the other positions z+Δz, z+2Δz, . . . can similarly be calculated. The circular tube temperature Tw(t,z) in the position z can be calculated by cumulatively adding (integrating), to the initial value Tw(0, z), the temperature change component depending on the difference between the fluid temperature Tg and the circular tube temperature Tw in the position z (the temperature change component represented by the second term of the equation (4-2)) and the temperature change component depending on the difference between the circular tube temperature Tw and the atmospheric temperature TA in the position z (the temperature change component represented by the third term of the equation (4-2)), at each given time interval.

In the present embodiment, the exhaust temperature observer 19 uses the model equations (4-1), (4-2) and determines the temperatures of the exhaust gas in the respective partial exhaust passageways 3a, 3b, 3c, 3d as follows:

Of the partial exhaust passageways 3a, 3b, 3c, 3d, each of the partial exhaust passageways 3a, 3b is defined by the exhaust pipe 6a. In order to estimate the temperatures of the exhaust gas in the partial exhaust passageways 3a, 3b, the temperature changes depending on the speed of the exhaust gas and the temperature gradient thereof (the temperature gradient in the direction in which the exhaust gas flows), the heat transfer between the exhaust gas and the exhaust pipe 6a, and the heat radiation from the exhaust pipe 6a into the atmosphere are taken into account in the same manner as described above with respect to the circular tube 23.

An estimated value of the exhaust gas temperature Tga in the partial exhaust passageway 3a and an estimated value of the temperature Twa (hereinafter referred to as "exhaust pipe temperature Twa") of the exhaust pipe 6a in the partial exhaust passageway 3a are determined by respective model equations (5-1), (5-2), shown below, in each cycle time of the processing sequence of the exhaust temperature observer 19. An estimated value of the exhaust gas temperature Tgb in the partial exhaust passageway 3b and an estimated value of the exhaust pipe temperature Twb in the partial exhaust passageway 3b are determined by respective model equations (6-1), (6-2), shown below, in each cycle time of the processing sequence of the exhaust temperature observer 19. More specifically, the exhaust gas temperature Tga and the exhaust pipe temperature Twa that are determined by the equations (5-1), (5-2) represent estimated values of the temperatures in the vicinity of the downstream end of the partial exhaust passageway 3a. Likewise, the exhaust gas temperature Tgb and the exhaust pipe temperature Twb that are determined by the equations (6-1), (6-2) represent estimated values of the temperatures in the vicinity of the downstream end of the partial exhaust passageway 3b.

$$Tga(k+1) = \qquad (5\text{-}1)$$
$$Tga(k) - Vg \cdot \frac{dt}{La} \cdot (Tga(k) - Texg(k)) + Aa \cdot dt \cdot (Twa(k) - Tga(k))$$

$$Twa(k+1) = \qquad (5\text{-}2)$$
$$Twa(k) + Ba \cdot dt \cdot (Tga(k) - Twa(k)) + Ca \cdot dt \cdot (T_A(k) - Twa(k))$$

$$Tgb(k+1) = \qquad (6\text{-}1)$$
$$Tgb(k) - Vg \cdot \frac{dt}{Lb} \cdot (Tgb(k) - Tga(k)) + Ab \cdot dt \cdot (Twb(k) - Tgb(k))$$

$$Twb(k+1) = \qquad (6\text{-}2)$$
$$Twb(k) + Bb \cdot dt \cdot (Tgb(k) - Twb(k)) + Cb \cdot dt \cdot (T_A(k) - Twb(k))$$

In the equations (5-1), (5-2), (6-1), (6-2), dt represents the period (cycle time) of the processing sequence of the exhaust temperature observer 19, and corresponds to Δt in the equations (4-1), (4-2). In the equations (5-1), (6-1), La, Lb represent the respective lengths (fixed values) of the partial exhaust passageways 3a, 3b, and correspond to Δz in the equation (4-1). Aa, Ba, Ca in the equations (5-1), (5-2) and Ab, Bb, Cb in the equations (6-1), (6-2) represent model coefficients corresponding respectively to a, b, c in the equations (4-1), (4-2), and the values of those model coefficients are set (identified) in advance by way of experimentation or simulation. In the equations (5-1), (6-1), Vg represents a parameter (to be determined as described later on) indicative of the speed of the exhaust gas, and corresponds to V in the equation (4-1).

The exhaust gas temperature Texg(k) (the exhaust gas temperature at the exhaust port 2) which is required to calculate a new estimated value Tga(k+1) of the exhaust gas temperature Tga according to the equation (5-1) is basically of the latest value determined according to the equation (1). Similarly, the exhaust gas temperature Tga(k) (the exhaust gas temperature in the partial exhaust passageway 3a) which is required to calculate a new estimated value Tgb(k+1) of the exhaust gas temperature Tgb according to the equation (6-1) is basically of the latest value determined according to the equation (5-1). The atmospheric temperature TA(k) which is required in the calculation of the equations (5-2), (6-2) is of the latest value of the atmospheric temperature detected by an atmospheric temperature sensor (in the present embodiment, a sensor on the engine 1 is used for this atmospheric temperature sensor), not shown. In the present embodiment, the gas speed parameter Vg which is required in the calculation of the equations (5-1), (6-1) is of a value which is calculated from latest detected values of the rotational speed NE and the intake pressure PB according to the following equation (7):

$$Vg = \frac{NE}{NEBASE} \cdot \frac{PB}{PBBASE} \qquad (7)$$

where NEBASE, PBBASE represent a predetermined rotational speed and a predetermined intake pressure, which are set to, for example, the maximum rotational speed of the engine 1 and 760 mmHg (≈101 kPa), respectively. The gas speed parameter Vg calculated according to the equation (7) is proportional to the speed of the exhaust gas, with $Vg \leqq 1$.

In the present embodiment, initial values $Tga(0)$, $Twa(0)$, $Tgb(0)$, $Twb(0)$ of the estimated values for the exhaust gas temperature Tga, the exhaust pipe temperature Twa, the exhaust gas temperature Tgb, and the exhaust pipe temperature Twb are set to the atmospheric temperature TA which is detected by the atmospheric temperature sensor (not shown) or the engine temperature TW (the temperature of the coolant of the engine 1) detected by the engine temperature sensor (not shown) when the engine 1 has started to operated (upon an engine startup).

The partial exhaust passageway 3c is defined by the catalyst 7 in the catalytic converter 4. The catalyst 7 generates heat by itself due to its own exhaust gas purifying action (specifically, an oxidizing/reducing action), and the amount of heat (the amount of heat per unit time) generated by the catalyst 7 is substantially in proportion to the speed of the exhaust gas. This is because as the speed of the exhaust gas is higher, the exhaust gas components reacting with the catalyst 7 per unit time increase.

According to the present embodiment, for estimating the exhaust gas temperature in the partial exhaust passageway 3c with high accuracy, the generation of heat by the catalyst 7 in the catalytic converter 4 as well as the temperature change depending on the speed and temperature gradient of the exhaust gas, the heat transfer between the exhaust gas and the catalyst 7, and the heat radiation from the catalyst 7 into the atmosphere are taken into account.

An estimated value of the exhaust gas temperature Tgc in the partial exhaust passageway 3c and an estimated value of the temperature Twc (hereinafter referred to as "catalyst temperature Twc") of the catalyst 7 which defines the partial exhaust passageway 3c are determined by respective model equations (8-1), (8-2), shown below, in each cycle time of the processing sequence of the exhaust temperature observer 19. More specifically, the exhaust gas temperature Tgc and the catalyst temperature Twc that are determined by the equations (8-1), (8-2) represent estimated values of the temperatures in the vicinity of the downstream end of the partial exhaust passageway 3c, i.e., in the vicinity of the outlet of the catalytic converter 4.

$$Tgc(k+1) = \qquad (8\text{-}1)$$
$$Tgc(k) - Vg \cdot \frac{dt}{Lc} \cdot (Tgc(k) - Tgb(k)) + Ac \cdot dt \cdot (Twc(k) - Tgc(k))$$

$$Twc(k+1) = Twc(k) + Bc \cdot dt \cdot (Tgc(k) - Twc(k)) + \qquad (8\text{-}2)$$
$$Cc \cdot dt \cdot (T_A(k) - Twc(k)) + Dc \cdot dt \cdot Vg$$

In the equation (8-1), Lc represents the length (fixed value) of the partial exhaust passageway 3c, and corresponds to $\Delta z$ in the equation (4-1). Ac, Bc, Cc in the equations (8-1), (8-2) represent model coefficients corresponding respectively to a, b, c in the equations (4-1), (4-2), and the values of those model coefficients are set (identified) in advance by way of experimentation or simulation. The fourth term on the right side of the equation (8-2) represents a temperature change component of the catalyst 7 in the catalytic converter 4 due to the heating of the catalyst 7 by itself, i.e., the temperature change per period of the processing sequence of the exhaust temperature observer 19, and is proportional to the gas speed parameter Vg. As with Ac through Cc, Dc in the fourth term represents a model coefficient that is set (identified) in advance by way of experimentation or simulation. Therefore, the equation (8-2) corresponds to the combination of the right side of the equation (4-2) with a temperature change component due to the heating of a passage-defining member (the catalyst 7).

dt, Vg in the equations (8-1), (8-2) have the same meanings and values as those in the equations (5-1) through (6-2). The value of TA used in the calculation of the equation (8-2) is identical to those used in the equation (5-2), (6-2). In the present embodiment, the initial values $Tgc(0)$, $Twc(0)$ of the exhaust gas temperature Tgc and the catalyst temperature Twc are equal to the detected value of the atmospheric temperature TA or the detected value of the engine temperature TW at the time the engine 1 has started to operate, as with the equations (5-1) through (6-2).

The partial exhaust passageway 3d is defined by the exhaust pipe 6b similar to the exhaust pipe 6a which define the partial exhaust passageways 3a, 3b. The exhaust gas temperature Tgd in the partial exhaust passageway 3d and the exhaust pipe temperature Twd of the exhaust pipe 6b, or more specifically the temperature at the downstream end of the partial exhaust passageway 3d, are determined respectively by the following equations (9-1), (9-2) which are similar to the equations (5-1) through (6-2):

$$Tgd(k+1) = \qquad (9\text{-}1)$$
$$Tgd(k) - Vg \cdot \frac{dt}{Ld} \cdot (Tgd(k) - Tgc(k)) + Ad \cdot dt \cdot (Twd(k) - Tgd(k))$$

$$Twd(k+1) = \qquad (9\text{-}2)$$
$$Twd(k) + Bd \cdot dt \cdot (Tgd(k) - Twd(k)) + Cd \cdot dt \cdot (T_A(k) - Twd(k))$$

In the equation (9-1), Ld represents the length (fixed value) of the partial exhaust passageway 3d, and corresponds to $\Delta z$ in the equation (4-1). Ad, Bd, Cd in the equations (9-1), (9-2) represent model coefficients corresponding respectively to a, b, c in the equations (4-1), (4-2), and the values of those model coefficients are set (identified) in advance by way of experimentation or simulation.

dt, Vg in the equations (9-1), (9-2) have the same meanings and values as those in the equations (5-1) through (6-2). The value of TA used in the calculation of the equation (9-2) is identical to those used in the equation (5-2), (6-2), (8-2). The initial values $Tgd(0)$, $Twd(0)$ of the exhaust gas temperature Tgd and the catalyst temperature Twd are equal to the detected value of the atmospheric temperature TA or the detected value of the engine temperature TW at the time the engine 1 has started to operate, as with the equations (5-1) through (6-2).

The processing sequence of the exhaust temperature observer 19, as described above, determines estimated values of the exhaust gas temperatures Texe, Tga, Tgb, Tgc, Tgd in the exhaust port 2 of the engine 1 and the partial exhaust passageways 3a, 3b, 3c, 3d successively downstream in each cycle time. The estimated value of the exhaust gas temperature Tgd in the partial exhaust passageway 3d which is located most downstream corresponds to the temperature of the exhaust gas in the vicinity of the location of the O2 sensor 8. The estimated value of the exhaust gas temperature Tgd is obtained as the estimated value of the exhaust gas temperature in the vicinity of the location of the O2 sensor 8. In the present embodiment, the estimated value of the exhaust gas temperature Tgd corresponds to exhaust gas temperature data according to the present invention.

Figure 6:
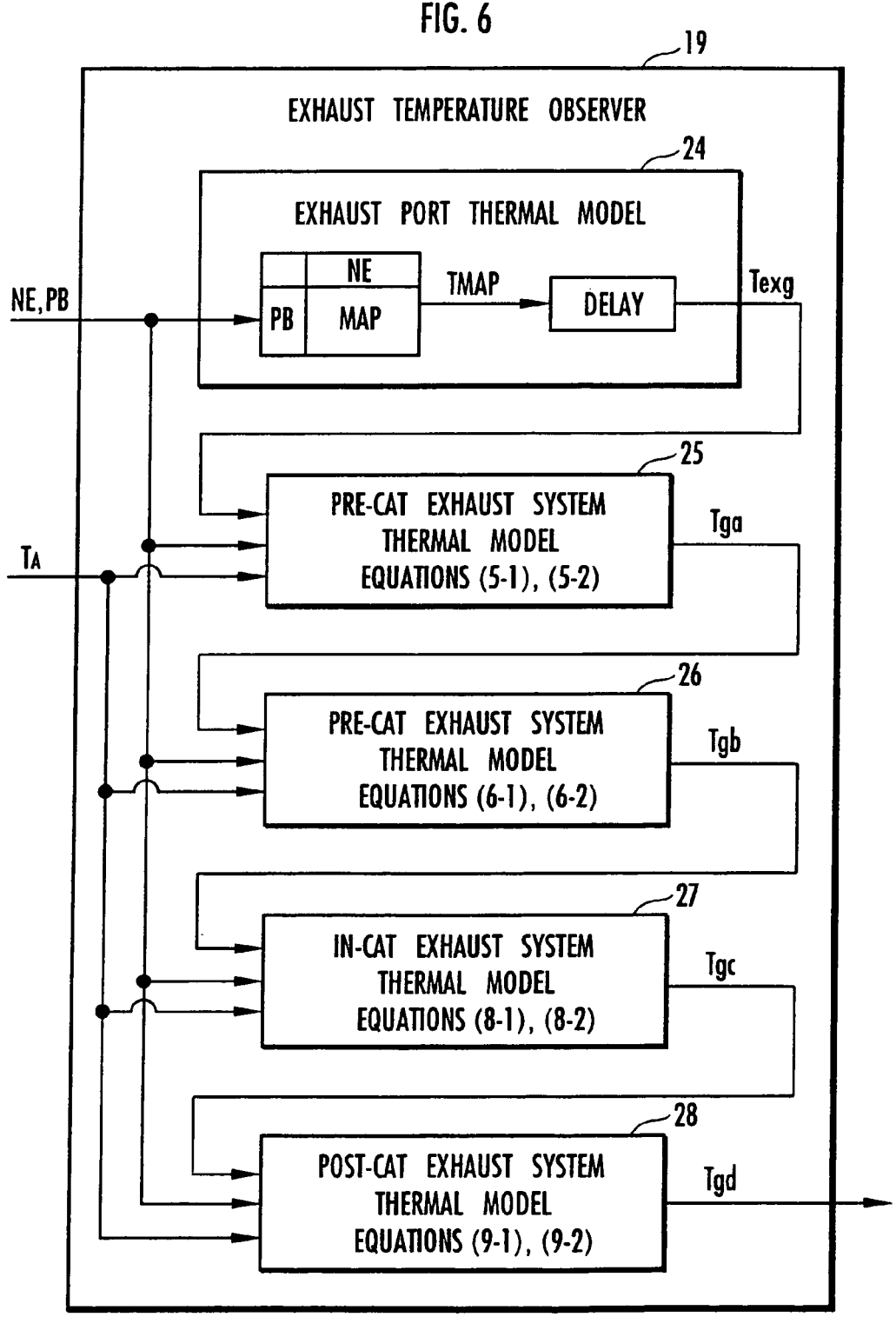
FIG. 6 is a block diagram showing a functional arrangement of the exhaust temperature observer in the sensor temperature control means shown in FIG. 4.

The algorithm of the estimating process of the exhaust temperature observer 19 is shown in block form in FIG. 6. In FIG. 6, the model equation (1) is referred to as an exhaust port thermal model 24, the model equations (5-1), (5-2) and the model equations (6-1), (6-2) as pre-CAT exhaust system thermal models 25, 26, respectively, the model equations (8-1), (8-2) as an in-CAT exhaust system thermal model 27, and the model equations (9-1), (9-2) as a post-CAT exhaust system thermal model 28. As shown in FIG. 6, each of the thermal models 24 through 28 is supplied with the detected values of the rotational speed NE and the intake pressure PB of the engine 1. The detected values of the rotational speed NE and the intake pressure PB which are supplied to the exhaust port thermal model 24 are used to determine the basic exhaust gas temperature TMAP, and the detected values of the rotational speed NE and the intake pressure PB which are supplied to the exhaust system thermal models 25 through 28 are used to determine the value of the gas speed parameter Vg. Each of the thermal models 25 through 28 is also supplied with the detected value of the atmospheric temperature TA. The pre-CAT exhaust system thermal model 25, the pre-CAT exhaust system thermal model 26, the in-CAT exhaust system thermal model 27, and the post-CAT exhaust system thermal model 28 are supplied with the estimated values of the exhaust gas temperatures Texg, Tga, Tgb, Tgc, respectively, which are outputted from the higher-level thermal models 24, 25, 26, 27. The post-CAT exhaust system thermal model 28 eventually produces the estimated value of the exhaust gas temperature Tgd in the vicinity of the location of the O2 sensor 8.

In the present embodiment, the detected value produced by the atmospheric temperature sensor on the engine 1 is used to estimate the temperatures of the passage-defining members (the exhaust pipe 6a, the catalyst 7 in the catalytic converter 4, and the exhaust pipe 6b) which define the partial exhaust passageways 3a, 3b, 3c, 3d. However, the detected value produced by an atmospheric sensor which is disposed outside of the exhaust passage 3 may be used to estimate the temperatures of those passage-defining members.

The element temperature observer 20 will be described below. The element temperature observer 20 estimates the temperature TO2 of the active element 10 of the O2 sensor 8 sequentially in given cycle times in view of the thermal transfer between the active element 10 and the exhaust gas held in contact therewith, the heat radiation from the active element 10 into the air within the active element 10, and the thermal transfer between the active element 10 and the ceramic heater 13 (hereinafter referred to simply as "heater 13") which heats the active element 10. The element temperature observer 20 also estimates the temperature Tht of the heater 13 in order to estimate the temperature TO2 of the active element 10. In estimating the temperature Tht of the heater 13, the element temperature observer 20 takes into account the heat transfer between the heater 13 and the active element 13 and the heat radiation from the heater 13 into the air within the active element 10, and also the heating of the heater 13 based on the electric energy supplied to the heater 13. The element temperature observer 20 has an estimating algorithm for estimating the temperature TO2 and the temperature Tht, which is constructed as follows:

The element temperature observer 20 determines an estimated value of the temperature TO2 of the active element 10 (hereinafter referred to as "element temperature TO2") of the O2 sensor 8 and an estimated value of the temperature Tht of the heater 13 (hereinafter referred to as "heater temperature Tht") sequentially in given cycle times respectively according to the model equations (10-1), (10-2) described below. The equation (10-1) is the equation of an element temperature model, and the equation (10-2) is the equation of a heater temperature model.

$$T_{O2}(k+1) = T_{O2}(k) + Ax \cdot dt \cdot (Tgd(k) - T_{O2}(k)) + \qquad (10\text{-}1)$$
$$Bx \cdot dt \cdot (Tht(k) - T_{O2}(k)) - Ex \cdot dt \cdot (T_{O2}(k) - TA'(k))$$

$$Tht(k+1) = Tht(k) - Cz \cdot dt \cdot (Tht(k) - T_{O2}(k)) - \qquad (10\text{-}2)$$
$$Fx \cdot dt \cdot (Tht(k) - TA'(k)) + Dx \cdot dt \cdot DUT(k) \cdot \frac{VB(k)^2}{NVB^2}$$

The equation (10-1) indicates that the temperature change of the active element 10 in each cycle time depends on a temperature change component (the second term on the right side of the equation (10-1)) depending on the difference between the exhaust gas temperature Tgd in the vicinity of the location of the O$_2$ sensor 8 (the exhaust gas temperature in the partial exhaust passageway 3d) and the element temperature $T_{O2}$, i.e., a temperature change component which is caused by the heat transfer between the active element 10 and the exhaust gas held in contact therewith, a temperature change component (the third term on the right hand of the equation (10-1)) depending on the difference between the element temperature $T_{O2}$ and the heater temperature Tht, i.e., a temperature change component which is caused by the heat transfer between the active element 10 and the ceramic heater 13, and a temperature change component (the fourth term on the right hand of the equation (10-1)) depending on the difference between the element temperature $T_{O2}$ and the temperature TA' of the air in the active element 10, i.e., a temperature change component due to the heat radiation from the active element 10 into the air therein, i.e., the sum of those temperature change components.

The equation (10-2) indicates that the temperature change of the heater 13 in each cycle time depends on a temperature change component (the second term on the right side of the equation (10-2)) depending on the difference between the element temperature TO2 and the heater temperature Tht, i.e., a temperature change component which is caused by the heat transfer between the active element 10 and the heater 13, a temperature change component (the third term on the right hand of the equation (10-2)) depending on the difference between the heater temperature Tht and the temperature TA' of the air in the active element 10, i.e., a temperature change component due to the heat radiation from the heater 13 into the air within the active element 10, and a temperature change component (the fourth term on the right side of the equation (10-2)) depending on the product of the duty cycle DUT (more accurately, the duty cycle DUT that is actually used for the heater controller 22 to control the energization of the heater 13) that is generated by the heat controller 22 as described later on and the square VB2 of the battery voltage VB, i.e., a temperature change component which is caused by the heating of the heater 13 based on the electric energy supplied thereto, i.e., the sum of those temperature change components.

In the equations (10-1), (10-2), Ax, Bx, Cx, Dx, Ex, Fx represent model coefficients whose values are set (identified) in advance by way of experimentation or simulation, and dt represents the period (cycle time) of the processing sequence of the element temperature observer 20. In the present embodiment, the period dt is set to the same value as the cycle time (represented by dt in the equations (5-1) through (9-2)) of the processing sequence of the exhaust temperature observer 19. In the equation (10-2), NVB represents a predetermined reference value (e.g., 14 V) of the battery voltage VB. The reference value may basically be set as desired as a standard voltage (a voltage that can normally be employed) for the battery voltage VB.

The fourth term on the right side of the equation (10-2) will supplementarily be described below. If the duty cycle of the PWM control for the heater 13 is constant and the resistance of the heater 13 upon its energization is constant, then the electric power supplied to the heater 13 is proportional to the square of the voltage applied to the heater 13, and the applied voltage is proportional to the battery voltage VB. The duty cycle DUT defines the period of time in which the heater 13 is energized, per period of the pulse voltage for the PWM control. Therefore, the product of the duty cycle DUT and the square VB2 of the battery voltage VB is proportional to the electric power supplied to the heater 13. The battery voltage VB changes as an alternator for charging the battery is turned on and off, for example. In the equation (10-2), the duty cycle DUT and the square VB2 of the battery voltage VB are multiplied in order to obtain a temperature change component due to the heating of the heater 13 when it is supplied with the electric power.

The duty cycle DUT(k) which is required in the calculation of the equation (10-2) is of the latest value of the duty cycle DUT that is actually used for the heater 22 to control the energization of the heater 13 (PWM control). In the present embodiment, the latest value of the atmospheric temperature TA detected by the atmospheric temperature sensor is substituted for the temperature TA'(k) of the air in the active element 10 which is required in the calculation of the equations (10-1), (10-2). In the present embodiment, therefore, TA'(k)=TA(k). Furthermore, the initial values TO2(0), Tht(0) of the element temperature TO2 and the heater temperature Tht are equal to the detected value of the atmospheric temperature TA or the detected value of the engine temperature TW at the time the engine 1 has started to operate, as described later.

The element temperature observer 20 sequentially calculates the estimated values of the element temperature TO2 and the heater temperature Tht according to the estimating algorithm described above. The estimated values of the element temperature TO2 and the heater temperature Tht correspond respectively to element temperature data and heater temperature data in the present invention.

The heater controller 22 will be described below. Basically, the heater controller 22 sequentially generates the duty cycle DUT as a control input (manipulated variable) for controlling the heater 13 according to an optimum predictive control algorithm, and controls the electric energy supplied to the heater 13 with the generated duty cycle DUT.

According to the present embodiment, attention is paid to the difference between the element temperature TO2 and a target value therefor, a change per given time in the difference (corresponding to a rate of change of the difference), and a change per given time in the heater temperature Tht (corresponding to a rate of change of the heater temperature Tht), and model equations for an object to be controlled by the heater controller 22 are introduced using the above differences and changes as state quantities relative to the object to be controlled by the heater controller 22. The heater controller 22 has its algorithm (optimum predictive control algorithm) constructed as described below. In the present embodiment, a duty cycle (control input) generated by the optimum predictive control algorithm, to be described below, is more precisely a duty cycle required to control the element temperature TO2 at a target value providing the battery voltage VB is kept constant at the reference value NVB represented by the equation (10-2). The duty cycle generated by the optimum predictive control algorithm which will be described below is referred to as a basic duty cycle SDUT or a basic control input SDUT.

First, model equations for the object to be controlled by the heater controller 22 will be described below. Changes $\Delta TO2$, $\Delta Tht$ per given time in the element temperature TO2 and the heater temperature Tht are expressed by the following equations (11-1), (11-2) based on the respective model equations (10-1), (10-2) with respect to the element temperature observer 20. The equation (11-2) is derived from an equation produced by using VB(k)=NVB and replacing DUT with SDUT in the equation (10-2). For deriving the equations (11-1), (11-2), the temperature TA' in the active element 10 is kept constant, i.e., remains unchanged, i.e., TA'(k+1)=TA'(k), in at least one cycle time of the processing sequence of the heater controller 22.

$$\Delta T_{O2}(k+1) = \Delta T_{O2}(k) + Ax \cdot dt \cdot (\Delta Tgd(k) - \Delta T_{O2}(k)) + Bx \cdot \quad (11\text{-}1)$$
$$dt \cdot (\Delta Tht(k) - \Delta T_{O2}(k)) - Ex \cdot dt \cdot \Delta T_{O2}(k)$$
$$= (1 - Ax \cdot dt - Bx \cdot dt - Ex \cdot dt) \cdot \Delta T_{O2}(k) +$$
$$Ax \cdot dt \cdot \Delta Tgd(k) + Bx \cdot dt \cdot \Delta Tht(k)$$

$$\Delta Tht(k+1) = \Delta Tht(k) - Cx \cdot dt \cdot (\Delta Tht(k) - \Delta T_{O2}(k)) - \quad (11\text{-}2)$$
$$Fx \cdot dt \cdot \Delta Tht(k) + Dx \cdot dt \cdot \Delta SDUT(k)$$
$$= (1 - Cx \cdot dt \cdot Fx \cdot dt) \cdot \Delta Tht(k) + Cx \cdot dt \cdot$$
$$\Delta T_{O2}(k) + Dx \cdot dt \cdot \Delta SDUT(k)$$

In the above equations (11-1), (11-2), $\Delta T_{O2}(k) = T_{O2}(k+1) - T_{O2}(k)$, $\Delta Tht(k) = Tht(k+1) - Tht(k)$, $\Delta Tgd(k) = Tgd(k+1) - Tgd(k)$, $\Delta SDUT(k) = SDUT(k+1) - SDUT(k)$.

A target value for the element temperature $T_{O2}$ is represented by R, and the difference e between the element temperature $T_{O2}$ and the target value R, i.e., the difference in each cycle time (hereinafter referred to as "element temperature difference e"), is defined according to the following equation (12):

$$e(k) = T_{O2}(k) - R(k) \quad (12)$$

A change $\Delta e$ in the element temperature difference e in each cycle time (hereinafter referred to as "element temperature difference change $\Delta e$") is expressed by the following equation (13) based on the above equations (11-1), (12):

$$\Delta e(k+1) = \Delta T_{O2}(k+1) - \Delta R(k+1) \quad (13)$$
$$= (1 - Ax \cdot dt - Bx \cdot dt - Ex \cdot dt) \cdot \Delta e(k) +$$
$$Ax \cdot dt \cdot \Delta Tgd(k) + Bx \cdot dt \cdot \Delta Tht(k) - \Delta R(k+1) +$$
$$(1 - Ax \cdot dt - Bx \cdot dt - Ex \cdot dt) \cdot \Delta R(k)$$

In the equation (13), $\Delta e(k) = e(k+1) - e(k)$, $\Delta R(k) = R(k+1) - R(k)$. In deriving the equation (13), the equation $\Delta T_{O2} = \Delta e(k) + \Delta R(k)$ (based on the equation (12)) is employed.

The equation $\Delta T_{O2} = \Delta e(k) + \Delta R(k)$ is applied to the equation (11-2), and the resulting equation is modified into the following equation (14):

$$\Delta Tht(k+1) = (1 - Cx \cdot dt - Fx \cdot dt) \cdot \Delta Tht(k) + \quad (14)$$
$$Cx \cdot dt \cdot \Delta e(k) + Dx \cdot dt \cdot \Delta SDUT(k) + Cx \cdot dt \cdot \Delta R(k)$$

If a state quantity vector $X0(k)=(e(k), \Delta e(k), \Delta Tht(k))^T$ (T represents a transposition) is introduced, then the following equation (15) is obtained from the equations (13), (14) and the equation $e(k+1)=e(k)+\Delta e(k)$:

$$X0(k+1) = \quad (15)$$
$$\Phi \cdot X0(k) + G \cdot \Delta SDUT(k) + Gd \cdot \Delta Tgd(k) + Gr \cdot R0(k+1)$$

where $X0(k) = (e(k), \Delta e(k), \Delta Tht(k))^T,$ $R0(k+1) = (\Delta R(k+1), \Delta R(k))^T,$ $G = (0, 0, Dx \cdot dt)^T,$ $Gd = (0, Ax \cdot dt, 0)^T,$ $$\Phi = \begin{bmatrix} 1 & 1 & 0 \\ 0 & 1 - Ax \cdot dt - Bx \cdot dt - Ex \cdot dt & Bx \cdot dt \\ 0 & Cx \cdot dtc & 1 - Cx \cdot dt - Fx \cdot dt \end{bmatrix}$$

$$Gr = \begin{bmatrix} 0 & 0 \\ -1 & 1 - Ax \cdot dt - Bx \cdot dt - Ex \cdot dt \\ 0 & Cx \cdot dt \end{bmatrix}$$

In the equation (15), R0, G, Gd represent vectors defined in the above definition clause, and Φ, Gr represent matrixes defined in the above definition clause.

The above equation (15) is a basic equation of the model of the object to be controlled by the heater controller 22.

In the above description, the period of the control process of the heater controller 22 is the same as the period dt of the processing sequences of the exhaust temperature observer 19 and the element temperature observer 20. Therefore, the period dt is used in the vectors G, Gd and the matrixes Φ, Gr in the equation (15). It is preferable to carry out the processing sequences of the exhaust temperature observer 19 and the element temperature observer 20 in a relatively short period (e.g., a period of 20 through 50 msec.) in order to increase the accuracy with which to estimate the temperatures. However, the period of the control process of the heater controller 22 may be longer than the period dt of the processing sequences of the exhaust temperature observer 19 and the element temperature observer 20 because the response speed of a change in the element temperature in response to the control input (duty cycle DUT) is relatively low (several Hz in terms of frequencies). According to an optimum predictive control process to be described later on, since future values of the target value R of the element temperature $T_{O2}$ need to be stored and held for a certain time, the storage capacity of a memory for storing the target value R becomes large if the period of the control process of the heater controller 22 is short.

According to the present embodiment, the period (cycle time) of the control process of the heater controller 22 is set to a value dtc (e.g., 300 through 500 msec.) longer than the period dt of the processing sequences of the exhaust temperature observer 19 and the element temperature observer 20.

In the present embodiment, the model equation of the object to be controlled by the heater controller 22 is rewritten from the equation (15) into the following equation (16), using the period dtc of the control process of the heater controller 22:

$$X0(n+1) = \quad (16)$$
$$\Phi \cdot X0(n) + G \cdot \Delta SDUT(n) + Gd \cdot \Delta Tgd(n) + Gr \cdot R0(n+1)$$

where $X0(n) = (e(n), \Delta e(n), \Delta Tht(n))^T,$ $R0(n+1) = (\Delta R(n+1), \Delta R(n))^T,$ $G = (0, 0, Dx \cdot dtc)^T,$ $Gd = (0, Ax \cdot dtc, 0)^T,$ $$\Phi = \begin{bmatrix} 1 & 1 & 0 \\ 0 & 1 - Ax \cdot dtc - Bx \cdot dtc - Ex \cdot dtc & Cx \cdot dtc \\ 0 & Cx \cdot dtc & 1 - Cx \cdot dtc - Fx \cdot dtc \end{bmatrix}$$

$$Gr = \begin{bmatrix} 0 & 0 \\ -1 & 1 - Ax \cdot dtc - Bx \cdot dtc - Ex \cdot dtc \\ 0 & Cx \cdot dt \end{bmatrix}$$

The equation (16) is a model equation of the object to be controlled which is actually used in the algorithm of the control process of the heater controller 22. In the equation (16), n represents the ordinal number of the period dtc of the control process of the heater controller 22.

Using the above model equation, the algorithm of the control process of the heater controller 22, i.e., the algorithm of the optimum predictive control process, is constructed as follows: It is assumed that the target value R of the element temperature $T_{O2}$ is set for the future until after Mr steps (until after a multiple by Mr of the period dtc of the control process of the heater controller 22), and the exhaust gas temperature Tgd which acts as a disturbance input is known in the future until after Md steps (until after a multiple by Md of the period dtc of the control process of the heater controller 22). The value Mr will be referred to as a target value predicting time Mr, and the value Md as an exhaust gas temperature predicting time Md. These predicting times Mr, Md are represented by integers whose unit is one period dtc of the control process of the heater controller 22.

A controller for generating a control input ΔSDUT for minimizing the value of an evaluating function J0 according to the following equation (17) serves as an optimum predictive servo controller:

$$J0 = \sum_{n=-M+1}^{\infty} [X0^T(n) \cdot Q0 \cdot X0(n) + \Delta SDUT^T(n) \cdot H0 \cdot \Delta SDUT(n)] \quad (17)$$

where M represents a larger one of the target value predicting time Mr and the exhaust gas temperature predicting time Md, i.e., M=max(Mr,Md), and Q0, H0 weighted matrixes for adjusting the convergence of the state quantity vector X0 and the power (size) of the control input ΔSDUT. Q0 represents a 3-row, 3-column diagonal matrix as X0 is a cubic matrix, and H0 is a Scalar quantity as ΔSDUT is a Scalar quantity. In the present embodiment, in order to reduce the power consumption of the heater 13, Q0 is set to a unit matrix (a diagonal matrix whose all diagonal components are "1") and H0 is set to a value (e.g., 1000) greater than the diagonal components of the matrix Q0. The target value predicting time Mr is set to 20, for example, and the exhaust gas temperature predicting time Md is set to 10, for example, with the period of the control process of the heater controller 22 being in the range from 300 to 500 msec.

The control input $\Delta SDUT$ for minimizing the value of the evaluating function according to the equation (17) is expressed by the equation (18) given below. In the present embodiment, it is assumed that the exhaust gas temperature Tgd is maintained at the present value in the future until after Md steps.

$$\Delta SDUT(n) = F0 \cdot X0(n) + \sum_{i=0}^{Mr} [Fr0(i) \cdot R0(n+1)] + Fdt \cdot \Delta Tgd(n) \quad (18)$$

In the equation (18), F0 in the first term on the right side represents a cubic row vector (Fs0, Fe0, Fx0), Fr0($i$) ($i$=1, 2, . . . , Mr) in the second term (the term of $\Sigma$) on the right side represent quadratic row vectors (Fr01($i$), Fr02($i$), and Fdt in the third term on the right side represents a Scalar quantity. They are expressed by the equations (19-1) through (19-3) given below.

$$F0 \equiv (Fs0, Fe0, Fx0) \quad (19\text{-}1)$$
$$= -[H0 + G^T \cdot P \cdot G]^{-1} \cdot G^T \cdot P \cdot \Phi$$

$$Fr0(i) \equiv (Fr01(i), Fr02(i)) \quad (19\text{-}2)$$
$$(i = 1, 2, \ldots, Mr)$$
$$= -[H0 + G^T \cdot P \cdot G]^{-1} \cdot G^T \cdot (\zeta^T)^{i-1} \cdot P \cdot Gr$$

$$Fdt = \sum_{i=0}^{Md} \{-[H0 + G^T \cdot P \cdot G]^{-1} \cdot G^T \cdot (\zeta^T)^i \cdot P \cdot Gd\} \quad (19\text{-}3)$$

where P represents a matrix (a 3-row, 3-column matrix) satisfying the following Ricatti equation (20-1), and $\zeta$ represents a matrix (a 3-row, 3-column matrix) expressed by the following equation (20-2):

$$P = Q0 + \Phi^T \cdot P \cdot \Phi - \Phi \cdot P \cdot G \cdot [H0 + G^T \cdot P \cdot G]^{-1} \cdot G^T \cdot P \cdot \Phi \quad (20\text{-}1)$$

$$\zeta = \Phi + G \cdot F0 \quad (20\text{-}2)$$

G, Gr, Gd, and $\Phi$ in the equations (19-1) through (19-3) and the equations (20-1), (20-2) are defined in the definition clause for the equation (16), and H0, Q0 in those equations represent weighted matrixes of the evaluating function J0 according to the equation (17) (H0 is a Scalar quantity).

The second term (the term of $\Sigma$) on the right side of the equation (18) is rewritten using the components of Fr0, R0 (see the definition clauses for the equations (19-2), (16)), and then modified into the following equation (21):

$$\sum_{i=1}^{Mr} [Fr0(i) \cdot R0(n+1)] = \sum_{i=1}^{Mr} [Fr(i) \cdot \Delta R(n+1)] \quad (21)$$

where $$Fr(i) = \begin{bmatrix} Fr02(1): & i = 0 \\ Fr01(i) + Fr02(i+1): & i = 1, 2, \ldots, Mr-1 \\ Fr01(Mr): & i = Mr \end{bmatrix}$$

By putting the equation (21) into the equation (18) and rewriting the first term on the right side of the equation (18) using the components of F0, X0 (see the definition clauses for the equations (19-1), (16)), the equation (18) is expressed by the following equation (22):

$$\Delta SDUT(n) = Fs0 \cdot e(n) + Fe0 \cdot \Delta e(n) + Fx0 \cdot \Delta Tht(n)$$

$$+ \sum_{i=0}^{Mr} [Fr(i) \cdot \Delta R(n+1)] + Fdt \cdot \Delta Tgd(n) \quad (22)$$

Since the basic control input SDUT(n) to be generated by the heater controller 22 is represented by the sum of its initial value SDUT(0) and $\Delta SDUT(1), \Delta SDUT(2), \ldots, \Delta SDUT(n)$ cumulatively added thereto, the following equation (23) is obtained from the above equation (22):

$$SDUT(n) = Fs0 \cdot \sum_{j=1}^{n} e(j) + Fe0 \cdot e(n) + Fx0 \cdot Tht(n) + \quad (23)$$

$$\sum_{i=1}^{Mr} [Fr(i) \cdot R(n+i)] + Fdt \cdot Tgd(n) - Fe0 \cdot e(0) -$$

$$Fx0 \cdot Tht(0) - \sum_{i=0}^{Mr} [Fr(i) \cdot R(0+i)] - Fdt \cdot Tgd(0) + SDUT(0)$$

By setting the initial value terms of the equation (23), i.e., the sixth term (the term of $Fe0 \cdot e(0)$) through the tenth term (SDUT(O)), to "0", the following equation (24) is obtained as an equation for calculating the basic control input SDUT(n) to be actually generated by the heater controller 22:

$$SDUT(n) = Fs0 \cdot \sum_{j=1}^{n} e(j) + Fe0 \cdot e(n) + \quad (24)$$

$$Fx0 \cdot Tht(n) + \sum_{i=1}^{Mr} [Fr(i) \cdot R(n+1)] + Fdt \cdot Tgd(n)$$

The equation (24) is a formula for calculating the basic control input SDUT(n) (basic duty cycle) for controlling the heater 13 with the heater controller 22 according to the optimum predictive control algorithm. The first through third terms (the term including $\Sigma e(j)$ through the term including Tht(n)) of the equation (24) represent control input components (a feedback component which will hereinafter be referred to as "optimum F/B component Uopfb") depending on the element temperature difference e and the heater temperature Tht. Specifically, the first and second terms represent a control input component depending on the element temperature difference e, and the third term represents a control input component depending on the heater temperature Tht. The fourth term (the term of $\Sigma Fr(i) \cdot R(n+1)$) on the right side of the equation (24) represents a control input component (a feed-forward component which will hereinafter be referred to as "optimum target value F/F component Uopfr") depending on the target value R. The fifth term (the term including Tgd(n)) represents a control input component (a feed-forward component which will hereinafter be referred to as "optimum disturbance F/F component Uopfd") depending on the exhaust gas temperature Tgd (which functions as a disturbance on the object to be controlled).

The basic control input SDUT(n) (basic duty cycle) determined by the equation (24) is a control input (duty cycle) that is required to control the element temperature $T_{O2}$ at the target value R in the case where the battery voltage VB is kept constant at the reference value SVB, as described above. Therefore, the heater controller 22 sequentially calculates a control input DUT(n) which is capable of controlling the element temperature $T_{O2}$ at the target value R independent of the battery voltage VB by correcting the basic control input SDUT(n), which has been calculated in each cycle time (period) of the control process according to the equation (24), with the ratio $NVB^2/VB(n)^2$ of the square of the present value VB(n) of the battery voltage VB and the square of the reference value NVB, as indicated by the following equation (25):

$$DUT(n) = \frac{NVB^2}{VB(n)^2} \cdot SDUT(n) \quad (25)$$

The heater controller 22 limits the control input DUT(n), i.e., the duty cycle DUT(n), within a predetermined range (0%≦DUT(n)≦100%), and then applies a pulse voltage having the duty cycle DUT(n) to a heater energization circuit (not shown) to adjust the electric power supplied to the heater 13.

Figure 7:
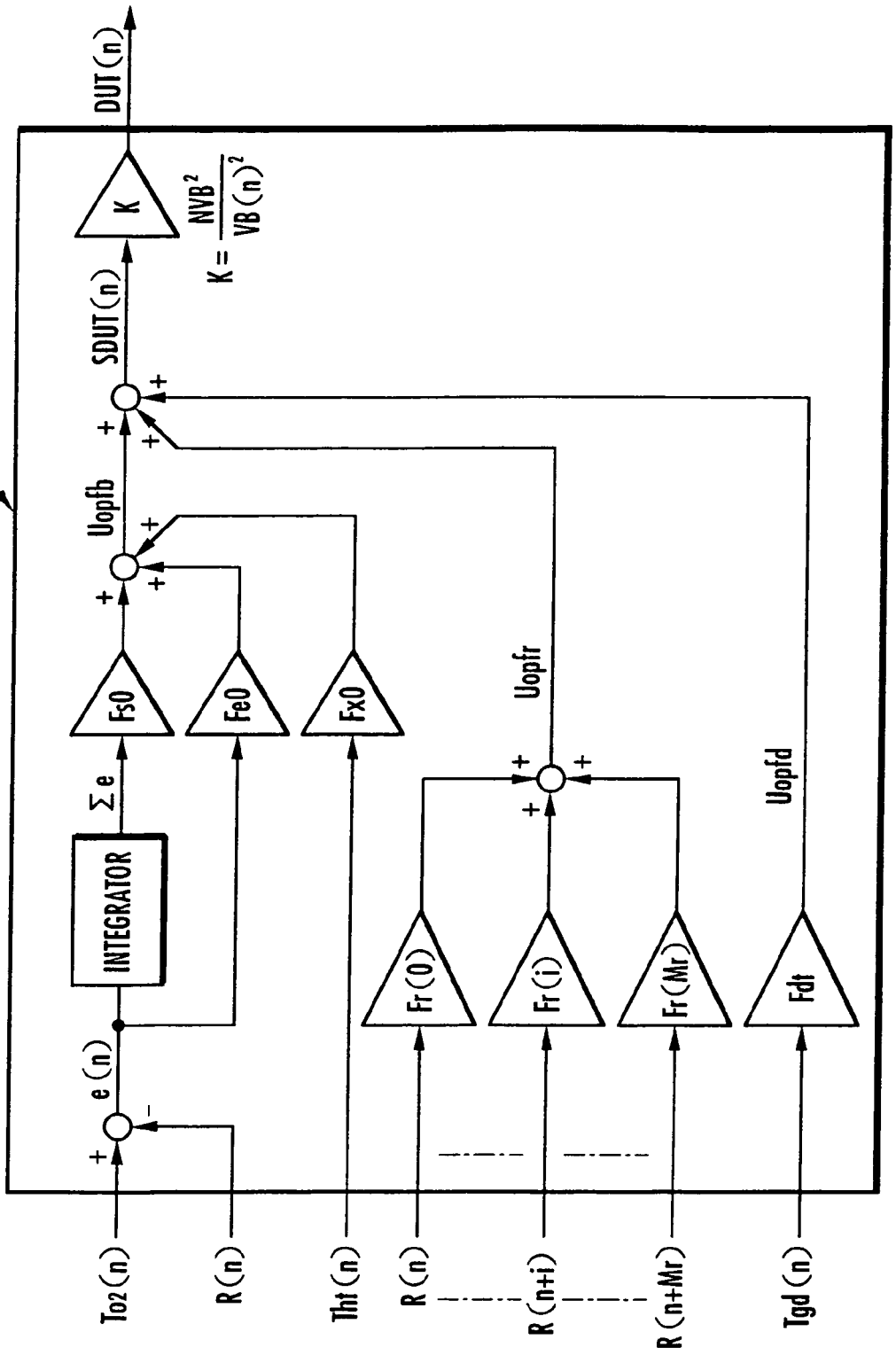
FIG. 7 is a block diagram showing a functional arrangement of a heater controller in the sensor temperature control means shown in FIG. 5.

The heater controller 22 which determines the duty cycle DUT as the control input according to the equations (24), (25) is expressed in block form as shown in FIG. 7.

In the present embodiment, since the exhaust gas temperature Tgd is maintained at the present value in the future until after Md steps, Fdt in the fifth term on the right side of the equation (24) is a Scalar quantity. If Tgd in each step in the future can be detected or estimated, then the control input DUT can be determined using those values of Tgd. In this case, Fdt is a vector comprising elements ((Md+1) elements) within { } of the equation (19-3). More specifically, if the series-series data of the exhaust gas temperature Tgd from the present until after Md steps is represented by Tgd(n), Tgd(n+1), ..., Tgd(n+Md), then the fifth term on the right side of the equation (24) is expressed by the inner product (Scalar product) of the vector comprising elements ((Md+1) elements) within { } of the equation (19-3) and a vector comprising, as elements, the series-series data Tgd(n), Tgd(n+1), ..., Tgd(n+Md) of the exhaust gas temperature Tgd. The inner product is in conformity with the fifth term on the right side of the equation (24) when Tgd(n)=Tgd(n+1)= . . . =Tgd(n+Md).

Fs0, Fe0, Fx0 which are required to determine the control input DUT(n) according to the equation (24) are of values calculated in advance according to the equation (19-1). Fr(i) (i=0, 1, ..., Mr) is of values calculated in advance according to the equations (21), (19-2). Fdt is of a value calculated in advance according to the equation (19-3). These coefficients Fs0, Fe0, Fx0, Fr(i), Fdt may not necessarily be of the values according to the defining equations, but may be of values adjusted by way of simulation or experimentation. Furthermore, the coefficients Fs0, Fe0, Fx0, Fr(i), Fdt may be changed depending on the element temperature, the heater temperature, etc.

The heater temperature Tht and the exhaust gas temperature Tgd which are required in the calculation of the equation (24) are of the latest estimated value of the heater temperature Tht determined by the element temperature observer 20 and the latest estimated value of the exhaust gas temperature Tgd determined by the exhaust temperature observer 19.

The element temperature difference e required in the calculation of the equation (24) is calculated from the latest estimated value of the element temperature TO2 determined by the element temperature observer 20 and the target value R which has been set in a cycle time prior to the target value predicting time Mr by the target value setting means 21.

The target value setting means 21 basically sets a temperature (e.g., 800° C. in the present embodiment) equal to or higher than 750° C. at which the output characteristics of the O2 sensor 8 are stably good, as the target value R for the temperature of the active element 10 in the same cycle time as the cycle time (period) of the processing sequence of the heater controller 22. In order to perform the processing sequence of the heater controller 22 according to the algorithm of the optimum predictive control process, the target value setting means 21 sets the target value R in each cycle time as a target value R(n+Mr) after the target value predicting time Mr from the present cycle time, and stores a series of target values R(n+Mr) for the target value predicting time Mr. Specifically, the target value setting means 21 stores Mr+1 target values R(n), R(n+1), ..., R(n+Mr) while sequentially updating them. The target value R used to determine the element temperature difference e that is required in the calculation of the equation (24) is the value R(n) set and stored by the target value setting means 21 as described above in the cycle time prior to the target value predicting time Mr. The target values R(n), R(n+1), ..., R(n+Mr) stored as described above are used to determine the value of the fourth term (the term of E including R(n+i)) of the equation (24).

If the target value R of the element temperature TO2 is set to a high temperature such as 800° C. from the start of operation of the engine 1, then the active element 10 tends to be damaged due to stresses caused by quick heating if water is applied to the active element 10 of the O2 sensor 8 when the engine 1 starts to operate. In the present invention, therefore, until a certain time (e.g., 15 seconds) elapses from the start of operation of the engine 1, the target value setting means 21 sets the target value R of the element temperature TO2 to a temperature lower than 750° C., e.g., 600° C. In the present embodiment, if the atmospheric temperature TA is low (e.g., TA<0° C.) upon elapse of a predetermined period of time after the engine 1 has started to operate, the target value R for the element temperature TO2 is set to a temperature (750° C.≦R<800° C.) slightly lower than the normal target value (800° C.) in order to prevent the heater 13 from being overheated.

Overall operation of the apparatus, particularly, the sensor temperature control means 18, according to the present embodiment will be described below.

When the engine 1 starts to operate (upon an engine startup), the sensor temperature control means 18 sets initial values Texg(0), Tga(0), Tgb(0), Tgc(0), Tgd(0), Twa(0), Twb(0), Twd(0), TO2(0), and Tht(0) of the estimated values of the exhaust gas temperatures Texg, Tga, Tgb, Tgc, Tgd, the exhaust pipe temperatures Twa, Twb, Twd, the catalyst temperature Twc, the element temperature TO2, and the heater temperature Tht, as follows: In the present embodiment, while the engine 1 stops its operation, the shutdown time of the engine 1 is measured. When the engine 1 starts to operate, the sensor temperature control means 18 determines whether the shutdown time immediately prior to the engine startup is in excess of a predetermined time (e.g., 2 hours) or not. If the shutdown time>the predetermined time, then since the temperature in the exhaust passage 3 and the tube wall thereof is considered to be substantially the same as the atmospheric temperature, the sensor temperature control means 18 sets the initial values Texg(0), Tga (0), Tgb(0), Tgc(0), Tgd(0), Twa (0), Twb(0), Twd(0), TO2(0), and Tht(0) to the detected value of the atmospheric temperature TA upon the startup of the engine 1. If the shutdown time≦ the predetermined time, then since the temperature in the exhaust passage 3 and the tube wall thereof is considered to be closer to the engine temperature TW (coolant temperature) than to the atmospheric temperature, because of the afterheat of the engine 1 after the engine 1 has stopped its preceding operation, the sensor temperature control means 18 sets the initial values Texg(0), Tga(0), Tgb(0), Tgc(0), Tgd(0), Twa(0), Twb(0), Twd(0), TO2(0), and Tht(0) to the detected value of the engine temperature TW upon the startup of the engine 1. These initial values are thus set to a temperature close to the actual temperature.

Figure 8:
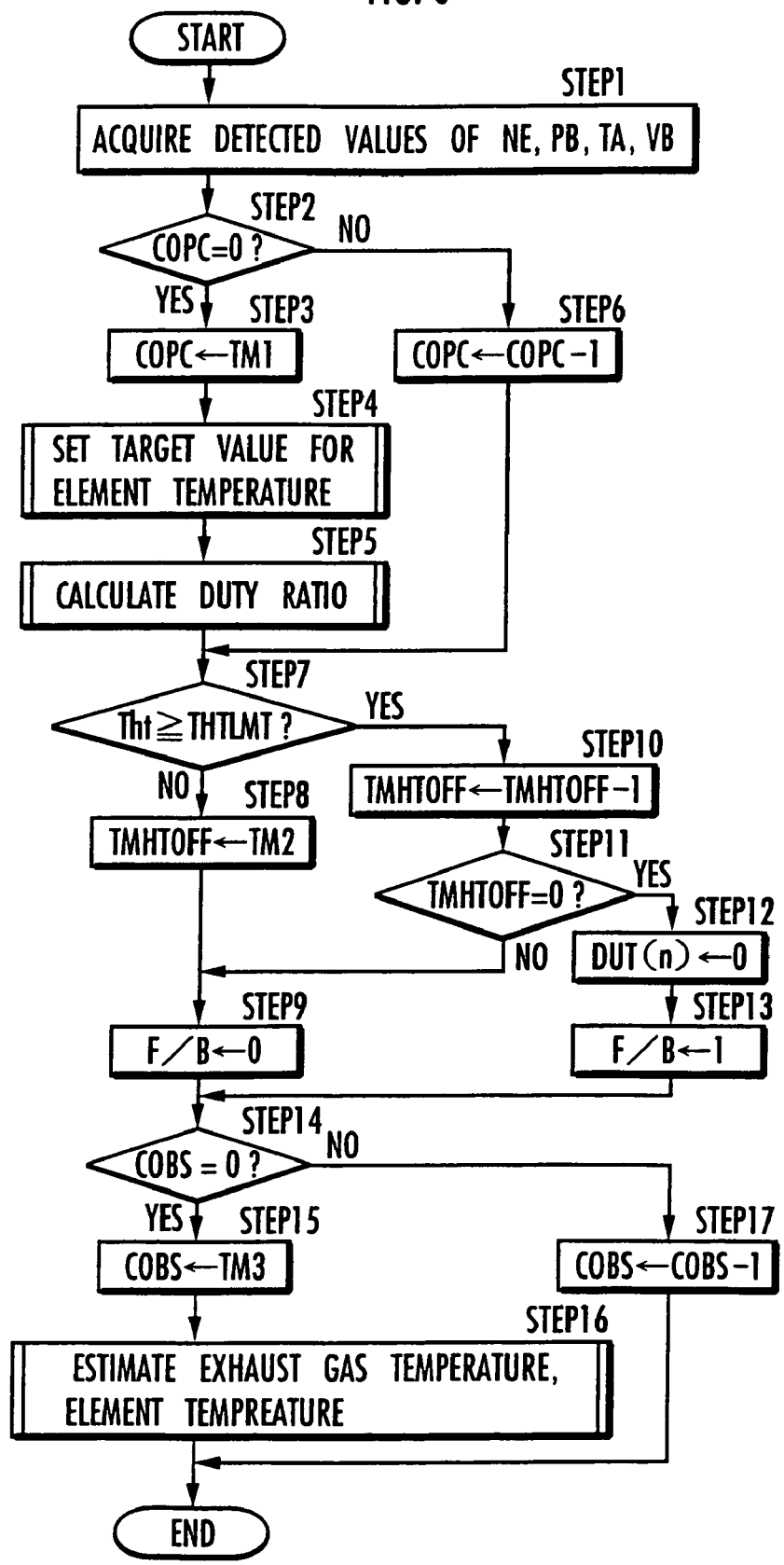
FIG. 8 is a flowchart of an overall processing sequence of the sensor temperature control means in the apparatus shown in FIG. 1.

When the engine 1 starts to operate, the sensor temperature control means 18 executes a main routine shown in FIG. 8 in a predetermined cycle time. The period in which the main routine is executed is shorter than the period dt of the processing sequence of the exhaust temperature observer 19 and the element temperature observer 20 and hence shorter than the period dtc of the processing sequence of the target value setting means 21 and the heater controller 22.

The sensor temperature control means 18 acquires detected values of the rotational speed NE and the intake pressure PB of the engine 1, the atmospheric temperature TA and the battery voltage VB in STEP1, and then determines the value of a countdown timer COPC for measuring the time dtc of one period of the processing sequence of the target value setting means 21 and the heater controller 22 in STEP2. The value of the countdown timer COPC has been initialized to "0" at the time when the engine 1 starts to operate.

If COPC=0, then the sensor temperature control means 18 newly sets the value of the countdown timer COPC to a timer setting time TM1 which corresponds to the period dtc of the control processes of the target value setting means 21 and the heater controller 22 in STEP3. Thereafter, the target value setting means 21 carries out a process of setting a target value R for the element temperature TO2 of the O2 sensor 8 in STEP4, and the heater controller 22 carries out a process of calculating a duty cycle DUT of the heater 13 in STEP5. If COPC≠0 in STEP2, then the sensor temperature control means 18 counts down the value of the countdown timer COPC in STEP6, and skips the processing in STEP4 and STEP5. Therefore, the processing in STEP4 and STEP5 is carried out at the period dtc determined by the timer setting time TM1.

Figure 9:
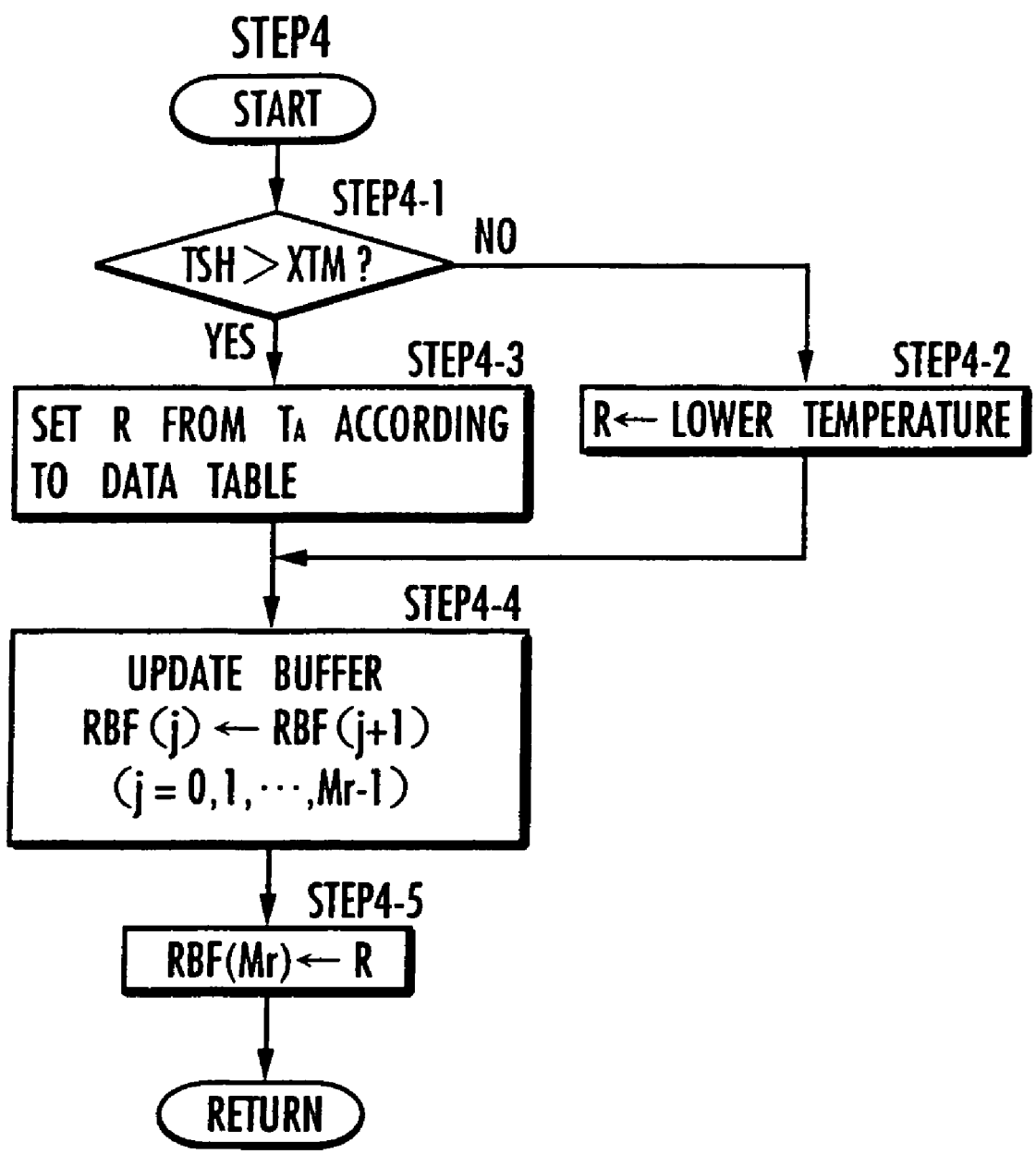
FIGS. 9 through 11 are flowcharts of subroutines of the flowchart shown in FIG. 8.

The processing in STEP4 and STEP5 is specifically carried out as follows: First, the processing in STEP4 is carried out by the target value setting means 21 as shown in FIG. 9.

The target value setting means 21 compares the value of a parameter TSH representative of the time that has elapsed from the start of the engine 1 with a predetermined value XTM (e.g., 15 seconds) in STEP4-1. If TSH≦XTM, i.e., if the engine 1 is in a state immediately after it has started to operate, then the target value setting means 21 sets the target value R for the element temperature TO2 to a low temperature (e.g., 600° C.) in order to prevent damage to the active element 10 of the O2 sensor 8 in STEP4-2. Specifically, the target value R that is set at this time is a target value R(n+Mr) after the target value predicting time Mr from the present.

If TSH>XTM in STEP4-1, then the target value setting means 21 sets the target value R for the element temperature TO2 from the present detected value (acquired in STEP1 shown in FIG. 8) of the atmospheric temperature TA based on a predetermined table in STEP4-3. The target value R that is set at this time is basically a predetermined value (800° C. in the present embodiment) equal to or higher than 750° C. if the atmospheric temperature TA is a normal temperature (e.g., TA≧0° C.). When the atmospheric temperature TA is low (e.g., TA<0° C.) as when the engine 1 is operating in a cold climate, if the target value R for the element temperature TO2 is a high temperature of 800° C., the temperature of the heater 13 is liable to be excessively high. In the present embodiment, when the temperature of the heater 13 becomes excessively high, the heater 13 is forcibly de-energized by an overheating prevention process (described later on) to prevent itself from a failure. In STEP4-3, according to the present embodiment, when the atmospheric temperature TA is low (e.g., TA<0° C.), the target value R for the element temperature TO2 is set to a value slightly lower than the normal value (e.g., 750° C.≦R<800° C.).

Specifically, as with the target value R set in STEP4-2, the target value R set in STEP4-3 is a target value R(n+Mr) after the target value predicting time Mr from the present.

After having set the target value R (=R(n+Mr)) in STEP4-2 or STEP4-3, the target value setting means 21 updates the values of Mr+1 buffers RBF(0), RBF(1), . . . , RBF(Mr) for storing target values R for the target value predicting time Mr in STEP4-4, STEP4-5. The processing in STEP4 is now finished.

In STEP4-4, specifically, the Mr buffers RBF(j) (j=0, 1, . . . , Mr−1) are updated from the values of RBF(j) to the values of RBF(j+1), and the value held in the buffer RBF(0) so far is erased. In STEP4-5, the buffer RBF(Mr) is updated to the target value newly set in STEP4-2 or STEP4-3. The values of the buffers RBF(0), RBF(1), . . . , RBF(Mr) thus updated correspond respectively to R(n), R(n+1), . . . , R(n+Mr) in the fourth term of the equation (24). The values of the buffers RBF(0), RBF(1), . . . , RBF(Mr) have been initialized to a predetermined value (e.g., the target value set in STEP4-2) at the time the engine 1 has started to operate.

Figure 10:
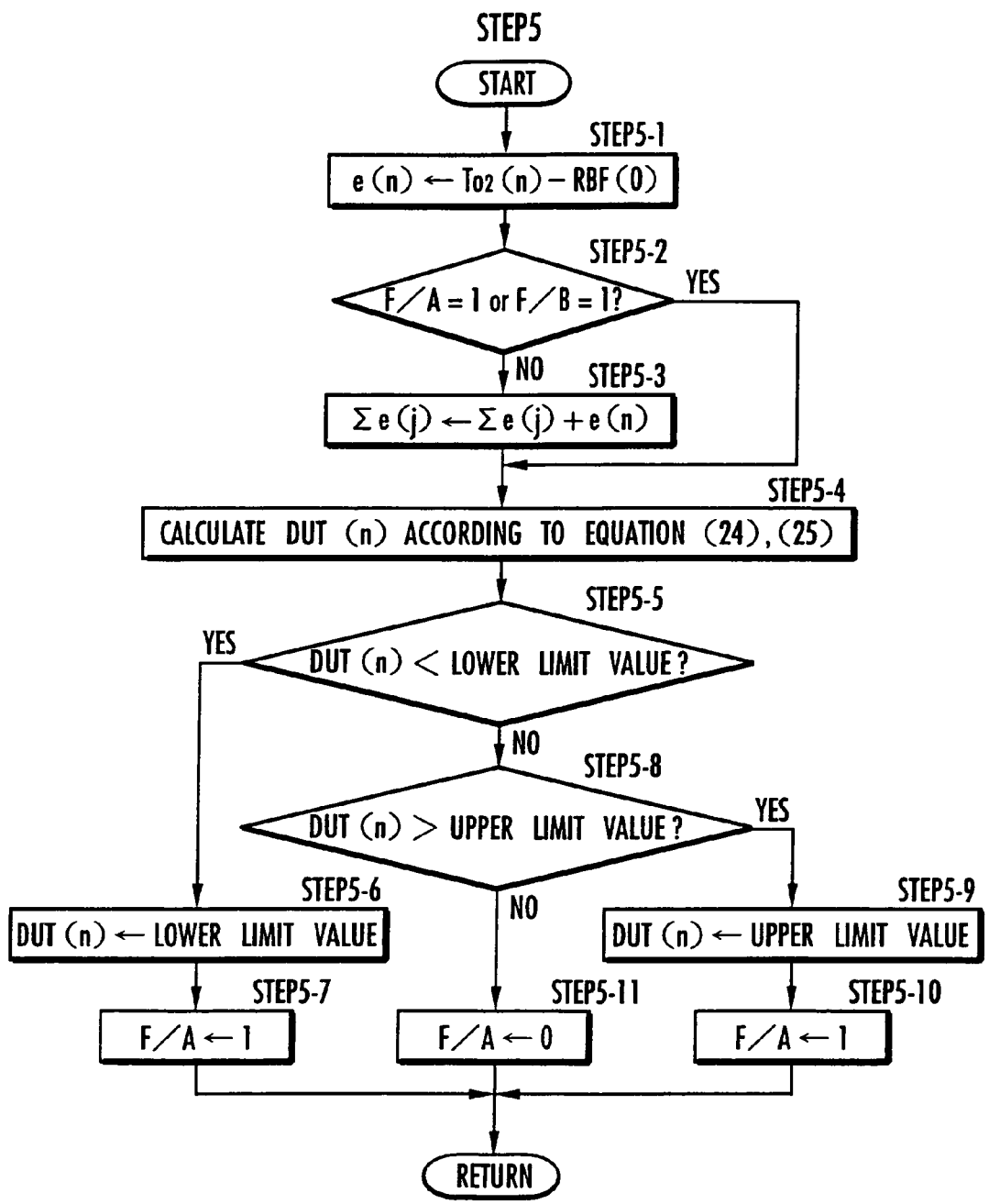

The processing in STEP5 is carried out by the heater controller 22 as shown in FIG. 10. The heater controller 22 calculates an element temperature difference e(n)=TO2(n)−RBF(0) between the present estimated value TO2(n) of the element temperature TO2 and the value of the buffer RBF(0) (=R(n)), i.e., the target value R set by the target value setting means 21 prior to the target value predicting time Mr in STEP5-1.

Then, the heater controller 22 determines the values of flags F/A, F/B in STEP5-2. The flag F/A is set to "0" or "1" in a limiting process (described later on) for limiting the duty cycle DUT. The flag F/A which is set to "1" means that the duty cycle DUT is forcibly limited to a predetermined upper or lower limit value, and the flag F/B which is set to "0" means that the duty cycle DUT is not limited to the predetermined upper or lower limit value (the upper limit value>DUT>the lower limit value). The flag F/B is set to "1" when the heater 13 is forcibly de-energized by the overheating prevention process. The flags F/A, F/B are initially set to "0".

If F/A=F/B=0 in STEP5-2, then the heater controller 22 adds the present value of Σe(j) in the first term of the equation (24) to the difference e(n) calculated in STEP5-1 in STEP5-3. In this manner, the difference e(n) is cumulatively added (integrated) in each cycle time dtc of the processing sequence of the heater controller 22. The initial value of Σe(j) is "0".

If F/A=1 or F/B=1 in STEP5-2, then since the present value of the duty cycle DUT is not a normal value, the heater controller 22 skips the processing in STEP5-3, but goes to STEP5-4, holding the present value of $\Sigma e(j)$.

Then, the heater controller 22 calculates the equations (24), (25) using the present value (latest value) of the element temperature difference e(n) determined in STEP5-1 and the present accumulated value of $\Sigma e(j)$, thus calculating the present value DUT(n) of the control input DUT for the heater 13 in STEP5-4. Specifically, the heater controller 22 calculates the basic duty cycle SDUT(n) according to the equation (24) from the present value of the difference e(n) determined in STEP5-1, the present accumulated value $\Sigma e(j)$, the present estimated value Tht(n) of the heater temperature Tht, the present values (=R(n), R(n+1), . . . , R(n+Mr)) of the buffers RBF(0), RBF(1), RBF(Mr), the present estimated value Tgd(n) of the exhaust gas temperature Tgd (the exhaust gas temperature at the location of the O2 sensor 8), and the values of predetermined coefficients Fs0, Fe0, Fx0, Fr(i) (i=0, 1, . . . , Mr), Fdt. The heater controller 22 then calculates the duty cycle DUT(n) by correcting the basic duty cycle SDUT(n) using the present value (the latest value acquired in STEP1 shown in FIG. 8) of the battery voltage VB. The initial value Tht(0) of the estimated value of the heater temperature Tht and the initial value Tgd(0) of the estimated value of the exhaust gas temperature Tgd, which are required for the first processing of STEP5-4 (at a stage where the processing sequences of the exhaust temperature observer 19 and the element temperature observer 20 are not executed) after the engine 1 has started to operate, are set to the atmospheric temperature TA or the engine temperature TW when the engine 1 starts to operate (an engine startup). Those initial values Tht(0), Tgd(0) are used in the calculation of the equation (24). After the processing sequences of the exhaust temperature observer 19 and the element temperature observer 20 are executed, the latest estimated values of the estimated values that are determined in the processing sequences of the exhaust temperature observer 19 and the element temperature observer 20 are used in the calculation of the equation (24).

Then, the heater controller 22 carries out a limiting process for limiting the duty cycle DUT(n) calculated in STEP5-4 in STEP5-5 through STEP5-11. Specifically, the heater controller 22 determines whether the duty cycle DUT(n) is smaller than a predetermined lower limit value (e.g., "0%") or not in STEP5-5. If DUT(n)<the lower limit value, then the heater controller 22 forcibly sets the value of DUT(n) to the lower limit value in STEP5-6. Thereafter, the value of the flag F/A (the flag used in STEP5-2) is set to "1" in STEP5-7.

If DUT(n)≧the lower limit value, then the heater controller 22 determines whether the duty cycle DUT(n) is greater than a predetermined upper limit value (e.g., 100%) or not in STEP5-8. If DUT(n)>the upper limit value, then the heater controller 22 forcibly sets the value of DUT(n) to the upper limit value in STEP5-9. Thereafter, the value of the flag F/A is set to "1" in STEP5-10. If the lower limit value≦DUT(n)≦the upper limit value, then the heater controller 22 holds the value of DUT(n), and sets the flag F/A to "0" in STEP5-11. The processing in STEP5 is now finished.

Control then returns to the main routine shown in FIG. 8. The sensor temperature control means 18 carries out the processing in STEP7 through STEP13. The processing in STEP7 through STEP13 represents a process of preventing the heater 13 from being overheated. In STEP7, the sensor temperature control means 18 determines whether or not the present estimated value (latest value) of the heater temperature Tht is equal to or higher than a predetermined upper limit value THTLMT (e.g., 930° C.). In the present embodiment, if Tht≧THTLMT, the sensor temperature control means 18 forcibly de-energizes the heater 13 to prevent the heater 13 from being damaged. However, the estimated value of Tht may temporarily rise to a value equal to or higher than the upper limit value THTLMT due to a disturbance or the like. According to the present embodiment, therefore, the sensor temperature control means 18 forcibly de-energizes the heater 13 if the state in which Tht≧THTLMT has continued for a predetermined time (e.g., 3 seconds, hereinafter referred to as "heater OFF delay time").

If Tht<THTLMT in STEP7, then the sensor temperature control means 18 sets the value of a countdown timer TMHTOFF for measuring the heater OFF delay time to a predetermined value TM2 corresponding to the heater OFF delay time in STEP8. Since the sensor temperature control means 18 does not forcibly de-energize the heater 13 at this time, the sensor temperature control means 18 sets the value of the flag F/B (the flag used in STEP5-2 shown in FIG. 10) to "0" in STEP9.

If Tht≧THTLMT in STEP7, then the sensor temperature control means 18 counts down the value of the countdown timer TMHTOFF by "1" in STEP10. Then, the sensor temperature control means 18 determines whether the value of the countdown timer TMHTOFF is "0" or not, i.e., whether the heater OFF delay time TM2 has elapsed with Tht≧THTLMT or not in STEP11.

If TMHTOFF≠0, then the sensor temperature control means 18 sets the flag F/B to "0" in STEP9. If TMHTOFF=0, then the sensor temperature control means 18 forcibly sets the present value of the duty cycle DUT to "0" in STEP12, and then sets the value of the flag F/B to "1" in STEP13.

When the flag F/B is set to "0" in STEP9, the sensor temperature control means 18 applies a pulsed voltage to the heater energization circuit according to the present value of the duty cycle DUT (the latest value calculated in STEP5), energizing the heater 13 with the electric energy depending on the duty cycle DUT. When the value of the flag F/B is set to "1" in STEP12, the sensor temperature control means 18 does not apply a pulsed voltage to the heater energization circuit, thus de-energizing the heater 13.

After having thus executed the processing in STEP7 through STEP13, i.e., the process of preventing the heater 13 from being overheated, the sensor temperature control means 18 determines the value of a countdown timer COBS for measuring the time dt of one period of the processing sequences of the exhaust temperature observer 19 and the element temperature observer 20 in STEP14. The value of the countdown timer COBS is initially set to "0" when the engine 1 has started to operate.

If COBS=0, then the sensor temperature control means 18 newly sets the value of COBS to a timer setting time TM3 (shorter than TM1 in STEP3) which corresponds to the period dt of the processing sequences of the exhaust temperature observer 19 and the element temperature observer 20 in STEP15. Then, the exhaust temperature observer 19 carries out a process of estimating the exhaust gas temperature Tgd (the exhaust gas temperature in the vicinity of the location of the O2 sensor 8), and the element temperature observer 20 carries out a process of estimating the element temperature TO2 (including a process of estimating the heater temperature Tht) in STEP16. If COBS≠0 in STEP14, the sensor temperature control means 18 counts down the value of COBC in STEP17, skipping the processing in STEP15 and STEP16. The processing in STEP16 is therefore carried out at a period dt which is determined by the timer setting time TM3. The main routine shown in FIG. 8 is now finished.

Figure 11:
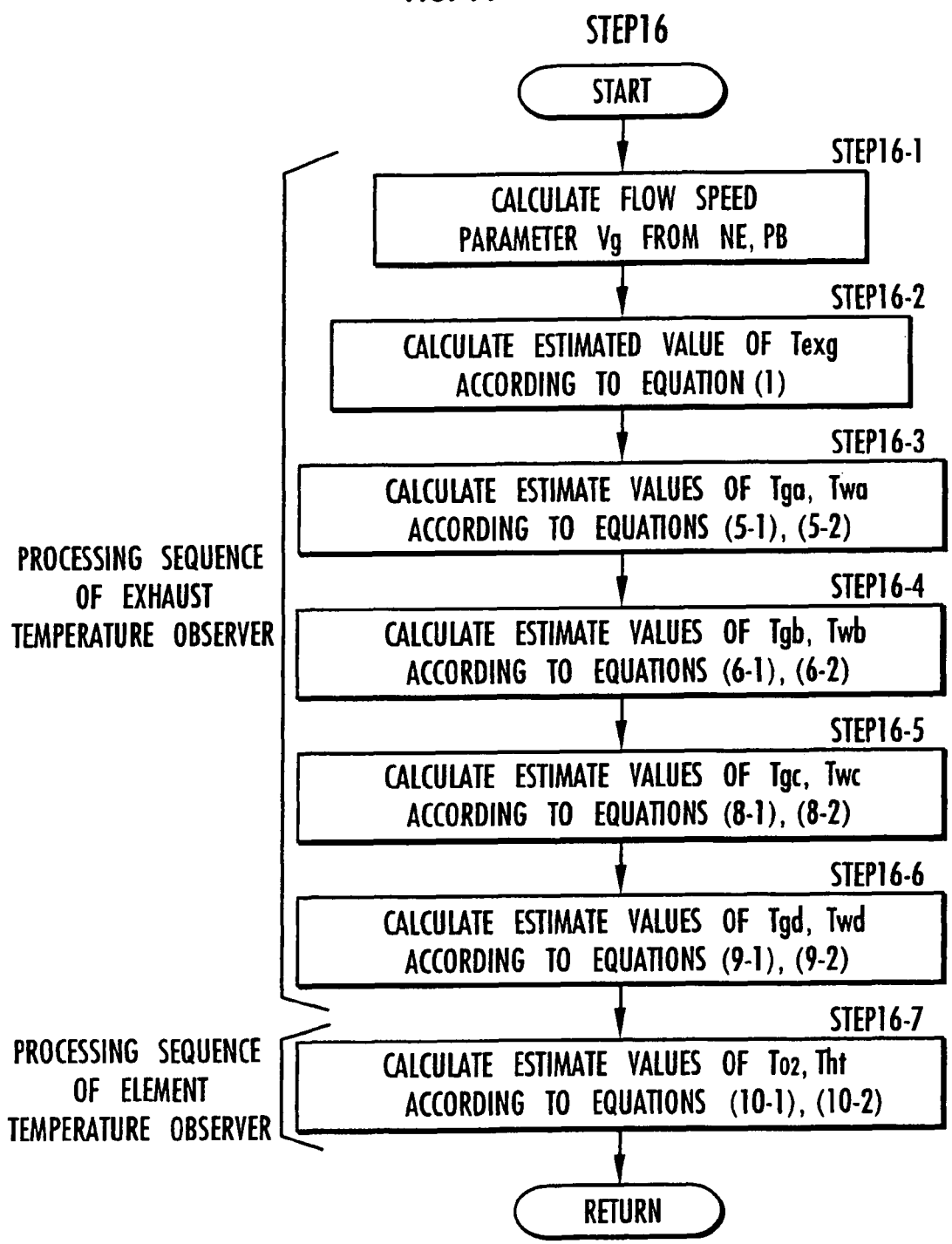

The processing in STEP16 is specifically carried out as shown in FIG. 11. The exhaust temperature observer 19 successively carries out the processing in STEP16-1 through STEP16-6 to determine an estimated value of the exhaust gas temperature Tgd in the vicinity of the location of the O2 sensor 8. In STEP16-1, the exhaust temperature observer 19 determines a gas speed parameter Vg according to the equation (7) using the present detected values (the latest values acquired in STEP1) of the rotational speed NE and the intake pressure PB of the engine 1. The gas speed parameter Vg is forcibly set to Vg=1 if the result calculated by the equation (7) exceeds "1" due to an excessive rotational speed of the engine 1.

Then, the exhaust temperature observer 19 calculates an estimated value of the exhaust gas temperature Texg at the exhaust port 2 of the engine 1 according to the equation (1) in STEP16-2. Specifically, the exhaust temperature observer 19 determines a basic exhaust gas temperature TMAP(NE,PB) from the present detected values of the rotational speed NE and the intake pressure PB of the engine 1 based on the predetermined map, and thereafter calculates the right side of the equation (1) using the basic exhaust gas temperature TMAP(NE,PB), the present estimated value Texg(k−1) (determined in STEP16-2 in the preceding cycle time) of the exhaust gas temperature Texg, and the value of a predetermined coefficient Ktex, thus calculating a new estimated value Texg(k) of the exhaust gas temperature Texg. In the present embodiment, while the engine 1 is idling and also while the supply of fuel to the engine 1 is being cut off, the basic exhaust gas temperature TMAP used in the calculation of the equation (1) is set to predetermined values corresponding to the respective engine operating states. When the engine 1 starts to operate (upon an engine startup), the atmospheric temperature TA or the engine temperature TW detected at this time is set as an initial value Texg(0) of the estimated value of the exhaust gas temperature Texg. When the equation (1) is calculated for the first time after the engine 1 has started to operate, the initial value Texg(0) is used as the value of Texg(k−1).

Then, the exhaust temperature observer 19 calculates an estimated value of the exhaust gas temperature Tga and an estimated value of the exhaust pipe temperature Twa in the partial exhaust passageway 3a according to the respective equations (5-1), (5-2) in STEP16-3. Specifically, the exhaust temperature observer 19 determines a new estimated value Tga(k+1) of the exhaust gas temperature Tga by calculating the right side of the equation (5-1) using the present estimated value Tga(k) (determined in STEP16-3 in the preceding cycle time) of the exhaust gas temperature Tga, the present estimated value (determined in STEP16-3 in the preceding cycle time) of the exhaust pipe temperature Twa, the present estimated value of the exhaust gas temperature Texg previously calculated in STEP16-2, the present value of the gas speed parameter Vg calculated in STEP16-1, the value of the predetermined model coefficient Aa, and the value of the period dt of the processing sequence of the exhaust temperature observer 19.

The exhaust temperature observer 19 calculates a new estimated value Twa(k+1) of the exhaust pipe temperature Twa by calculating the right side of the equation (5-2) using the present estimated value Tga(k) (determined in in the preceding cycle time) of the exhaust gas temperature Tga, the present estimated value (determined in STEP16-3 in the preceding cycle time) of the exhaust pipe temperature Twa, the values of the predetermined model coefficients Ba, Ca, and the value of the period dt of the processing sequence of the exhaust temperature observer 19.

When the engine 1 starts to operate (upon an engine startup), the atmospheric temperature TA or the engine temperature TW detected at this time is set as initial values Tga(0), Twa(0) of the estimated values of the exhaust gas temperature Tga and the exhaust pipe temperature Twa. When the equations (5-1), (5-2) are calculated for the first time after the engine 1 has started to operate, these initial values Tga(0), Twa(0) are used as the respective values of Tga(k−1), Twa(k−1).

Then, the exhaust temperature observer 19 calculates an estimated value of the exhaust gas temperature Tgb and an estimated value of the exhaust pipe temperature Twb in the partial exhaust passageway 3b according to the respective equations (6-1), (6-2) in STEP16-4. Specifically, the exhaust temperature observer 19 determines a new estimated value Tgb(k+1) of the exhaust gas temperature Tgb by calculating the right side of the equation (6-1) using the present estimated value Tgb(k) (the latest value determined in STEP16-4 in the preceding cycle time) of the exhaust gas temperature Tgb, the present estimated value (the latest value determined in STEP16-4 in the preceding cycle time) of the exhaust pipe temperature Twb, the present estimated value of the exhaust gas temperature Tga previously calculated in STEP16-3, the present value of the gas speed parameter Vg calculated in STEP16-1, the value of the predetermined model coefficient Ab, and the value of the period dt of the processing sequence of the exhaust temperature observer 19.

The exhaust temperature observer 19 calculates a new estimated value Twb(k+1) of the exhaust pipe temperature Twb by calculating the right side of the equation (6-2) using the present estimated value Tgb(k) (the latest value determined in STEP16-4 in the preceding cycle time) of the exhaust gas temperature Tgb, the present estimated value (the latest value determined in STEP16-4 in the preceding cycle time) of the exhaust pipe temperature Twb, the values of the predetermined model coefficients Bb, Cb, and the value of the period dt of the processing sequence of the exhaust temperature observer 19.

When the engine 1 starts to operate, the atmospheric temperature TA or the engine temperature TW detected at this time is set as initial values Tgb(0), Twb(0) of the estimated values of the exhaust gas temperature Tgb and the exhaust pipe temperature Twb. When the equations (6-1), (6-2) are calculated for the first time after the engine 1 has started to operate, these initial values Tgb(0), Twb(0) are used as the respective values of Tgb(k−1), Twb(k−1).

Then, the exhaust temperature observer 19 calculates an estimated value of the exhaust gas temperature Tgc and an estimated value of the catalyst temperature Twc in the partial exhaust passageway 3c according to the respective equations (8-1), (8-2) in STEP16-5. Specifically, the exhaust temperature observer 19 determines a new estimated value Tgc(k+1) of the exhaust gas temperature Tgc by calculating the right side of the equation (8-1) using the present estimated value Tgc(k) (the latest value determined in STEP16-5 in the preceding cycle time) of the exhaust gas temperature Tgc, the present estimated value (the latest value determined in STEP16-5 in the preceding cycle time) of the catalyst temperature Twc, the present estimated value of the exhaust gas temperature Tgb previously calculated in STEP16-4, the present value of the gas speed parameter Vg calculated in STEP16-1, the value of the predetermined model coefficient Ac, and the value of the period dt of the processing sequence of the exhaust temperature observer 19.

The exhaust temperature observer 19 calculates a new estimated value Twc(k+1) of the catalyst temperature Twc by calculating the right side of the equation (8-2) using the present estimated value Tgc(k) (the latest value determined in STEP16-5 in the preceding cycle time) of the exhaust gas temperature Tgc, the present estimated value (the latest value determined in STEP16-5 in the preceding cycle time) of the catalyst temperature Twc, the present value of the gas speed parameter Vg calculated in STEP16-1, the values of the predetermined model coefficients Bc, Cc, Dc, and the value of the period dt of the processing sequence of the exhaust temperature observer 19.

When the engine 1 starts to operate, the atmospheric temperature TA or the engine temperature TW detected at this time is set as initial values Tgc(0), Twc(0) of the estimated values of the exhaust gas temperature Tgc and the catalyst temperature Twc. When the equations (8-1), (8-2) are calculated for the first time after the engine 1 has started to operate, these initial values Tgc(0), Twc(0) are used as the respective values of Tgc(k−1), Twc(k−1).

Then, the exhaust temperature observer 19 calculates an estimated value of the exhaust gas temperature Tgd and an estimated value of the exhaust pipe temperature Twd in the partial exhaust passageway 3$d$ (near the location of the O2 sensor 8) according to the respective equations (9-1), (9-2) in STEP16-6. Specifically, the exhaust temperature observer 19 determines a new estimated value Tgd(k+1) of the exhaust gas temperature Tgd by calculating the right side of the equation (9-1) using the present estimated value Tgd(k) (the latest value determined in STEP16-6 in the preceding cycle time) of the exhaust gas temperature Tgd, the present estimated value (the latest value determined in STEP16-6 in the preceding cycle time) of the exhaust pipe temperature Twd, the present estimated value of the exhaust gas temperature Tgc previously calculated in STEP16-5, the present value of the gas speed parameter Vg calculated in STEP16-1, the value of the predetermined model coefficient Ad, and the value of the period dt of the processing sequence of the exhaust temperature observer 19.

The exhaust temperature observer 19 calculates a new estimated value Twd(k+1) of the exhaust pipe temperature Twd by calculating the right side of the equation (9-2) using the present estimated value Tgd(k) (the latest value determined in STEP16-6 in the preceding cycle time) of the exhaust gas temperature Tgd, the present estimated value (the latest value determined in STEP16-6 in the preceding cycle time) of the exhaust pipe temperature Twd, the values of the predetermined model coefficients Bd, Cd, and the value of the period dt of the processing sequence of the exhaust temperature observer 19.

When the engine 1 starts to operate, the atmospheric temperature TA or the engine temperature TW detected at this time is set as initial values Tgd(0), Twd(0) of the estimated values of the exhaust gas temperature Tgd and the exhaust pipe temperature Twd. When the equations (9-1), (9-2) are calculated for the first time after the engine 1 has started to operate, these initial values Tgd(0), Twd(0) are used as the respective values of Tgd(k−1), Twd(k−1).

Then, the element temperature observer 20 executes the processing in STEP16-7 to determine estimated values of the element temperature TO2 of the O2 sensor 8 and the heater temperature Tht according to the equations (10-1), (10-2). Specifically, the element temperature observer 20 determines a new estimated value TO2($k$+1) of the element temperature TO2 by calculating the right side of the equation (10-1) using the present estimated value TO2($k$) (the latest value determined in STEP16-7 in the preceding cycle time) of the element temperature TO2, the present estimated value Tht(k) (the latest value determined in STEP16-7 in the preceding cycle time) of the heater temperature Tht, the present estimated value Tgd(k) of the exhaust gas temperature Tgd previously calculated in STEP16-6, the present value TA(k) (the latest value acquired in STEP1 shown in FIG. 8) of the detected value of the atmospheric temperature TA as the temperature TA' of the air in the active element 10, the values of the predetermined model coefficients Ax, Bx, and the value of the period dt (=the period of the processing sequence of the exhaust temperature observer 19) of the processing sequence of the element temperature observer 20.

Then, the element temperature observer 20 determines a new estimated value Tht(k+1) of the heater temperature Tht by calculating the right side of the equation (10-2) using the present estimated value TO2($k$) (the latest value determined in STEP16-7 in the preceding cycle time) of the element temperature TO2, the present estimated value Tht(k) (the latest value determined in STEP16-7 in the preceding cycle time) of the heater temperature Tht, the present value TA(k) (the latest value acquired in STEP1 shown in FIG. 8) of the detected value of the atmospheric temperature TA as the temperature TA' of the air in the active element 10, the present value DUT(k) of the duty cycle DUT, the values of the predetermined model coefficients Cx, Dx, and the value of the period dt of the processing sequence of the element temperature observer 20.

When the engine 1 starts to operate, the atmospheric temperature TA or the engine temperature TW detected at this time is set as initial values TO2(0), Tht(0) of the estimated values of the element temperature TO2 and the heater temperature Tht. When the equations (10-1), (10-2) are calculated for the first time after the engine 1 has started to operate, these initial values TO2(0), Tht(0) are used as the respective values of TO2($k$−1), Tht(k−1). The duty cycle DUT(k) used in the equation (10-2) is basically of the latest value determined by the heater controller 22 in STEP5. However, if the value of the duty cycle DUT is limited in STEP12 to "0", i.e., to de-energize the heater 13, then the limited value of the duty cycle DUT is used in the equation (10-2).

The above processing sequence of the sensor temperature control means 18 controls the electric energy supplied to the heater 13 of the O2 sensor 8 in order to keep the element temperature TO2 of the O2 sensor 8 at the target value R. Except immediately after the engine 1 has started to operate and when the atmospheric temperature TA is considerably low, the target value R is normally set to 800° C. As a result, the output characteristics of the O2 sensor 8 can be maintained stably as the characteristics suitable for controlling the air-fuel ratio of the engine 1, i.e., for controlling the air-fuel ratio thereof for the catalytic converter 4 to perform a better exhaust purifying capability, and the air-fuel ratio of the engine 1 can well be controlled to allow the catalytic converter 4 to perform a better exhaust purifying capability.

According to the present embodiment, the duty cycle DUT as a control input for the heater 13 includes a control input component (the first and second terms of the equation (24)) depending on the difference (element temperature difference) e between the estimated value of the element temperature TO2 and the target value R, and also includes a control input component (the third term of the equation (24) depending on the estimated value of the heater temperature Tht. Therefore, when the element temperature TO2 varies with respect to the target value R, it is possible to converge the element temperature TO2 smoothly to the target value R while preventing the duty cycle DUT of the heater 13 from being excessively changed. According to the present embodiment, since ΔTht of the heater temperature Tht is a state quantity of the model to be controlled, the control input component depending on the estimated value of the heater temperature Tht is meant to be a feedback component.

According to the present embodiment, furthermore, the duty cycle DUT also includes a control input component depending on the estimated value of the exhaust gas temperature Tgd which acts as a disturbant factor for varying the element temperature TO2, i.e., the optimum disturbance F/F component Uopfd. The coefficient Fdt relative to the optimum disturbance F/F component Uopfd is determined according to a predictive control algorithm on the assumption that the present exhaust gas temperature will continue until after the exhaust gas temperature predicting time Md. Consequently, it is possible to control the element temperature TO2 at the target value R while suppressing variations of the element temperature TO2 due to variations of the exhaust gas temperature Tgd. In particular, as the coefficient Fdt relative to the optimum disturbance F/F component Uopfd is determined according to a predictive control algorithm, any variations of the element temperature TO2 due to variations of the exhaust gas temperature Tgd can be minimized. As a result, the stability of the process of controlling the element temperature TO2 at the target value R is effectively increased, and hence the stability of the output characteristics of the O2 sensor 8 is also effectively increased.

Furthermore, the control input DUT includes the control input component depending on the target value R for the element temperature TO2, i.e., the optimum target value F/F component Uopfr. In addition, the optimum target value F/F component Uopfr is turned into a control input component depending on the target value R from the present until after the target value predicting time Mr by the predictive control algorithm. Therefore, when the target value R changes from a low temperature (600° C.) immediately after the engine 1 has started to operate to a normal high temperature (750° C. through 800° C.) in particular, the control input DUT is prevented from becoming temporarily large excessively, and the element temperature TO2 is prevented from overshooting with respect to the target value R. The stability of the output characteristics of the O2 sensor 8 is also effectively increased.

Figure 12:
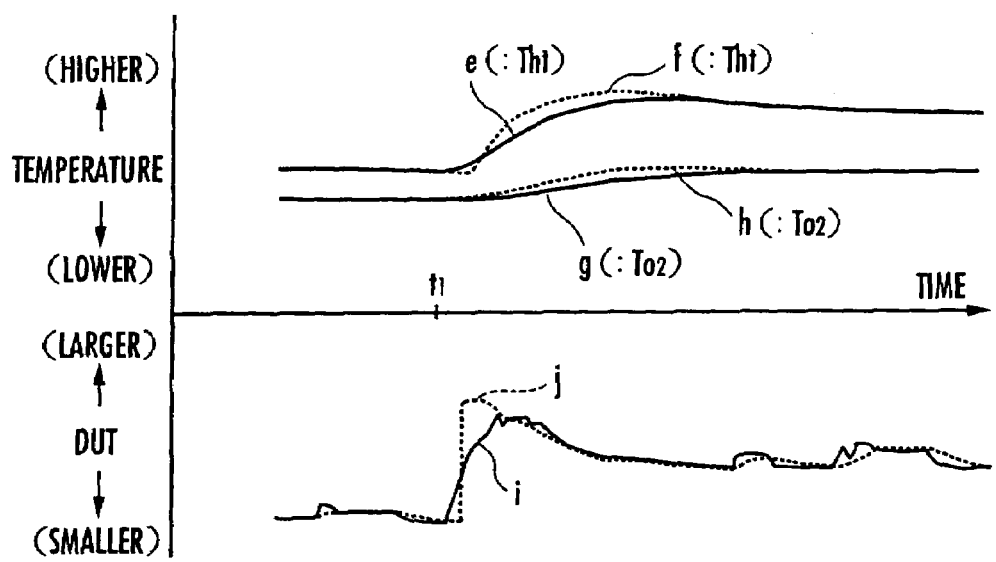
FIGS. 12 and 13 are graphs showing the results of simulations of the first embodiment.
Figure 13:
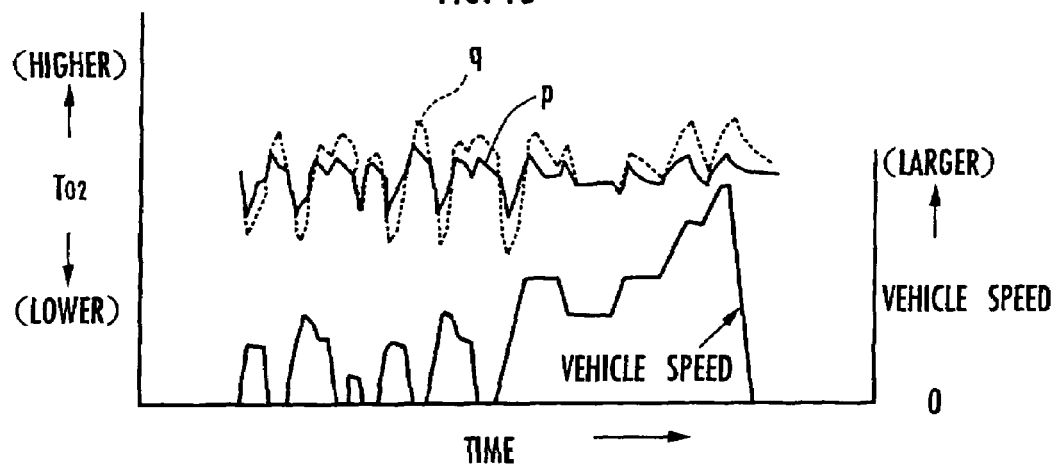

FIGS. 12 and 13 show the results of simulations of the present embodiment. FIG. 12 illustrates how the heater temperature Tht, the element temperature TO2, and the duty cycle DUT change when the target value R changes from a low-temperature target value (600° C.) to a high-temperature target value (800° C.) at a time t1 while a vehicle carrying the engine 1 is running at a constant speed (in a steady operating state of the engine 1). In FIG. 12, the solid-line curves e, g, i indicate how the heater temperature Tht, the element temperature TO2, and the duty cycle DUT, respectively, change when the heater 13 is controlled according to the present embodiment. The broken-line curves f, h, j indicate how the heater temperature Tht, the element temperature TO2, and the duty cycle DUT, respectively, change in a comparative example. According to the comparative example, the duty cycle DUT is determined using an equation similar to the equation (24) except that the optimum target value F/F component Uopfr (the fourth term of the equation (24)) depending on the target value R is removed from the equation (24).

It can be seen from FIG. 24 that according to the present embodiment, since the duty cycle DUT includes the optimum target value F/F component Uopfr depending on the target value R, when the target value R switches, the duty cycle DUT is prevented from becoming excessively large, and transient overshooting of the heater temperature Tht and the element temperature TO2 is reduced.

FIG. 13 shows how the element temperature TO2 changes while a vehicle carrying the engine 1 is running at varying vehicle speeds as indicated by a lower curve in FIG. 13 (in various changing operating states of the engine 1). In FIG. 13, the solid-line curve p indicates how the element temperature TO2 changes when the heater 13 is controlled according to the present embodiment. The broken-line curve q indicates how the element temperature TO2 changes in a comparative example. According to the comparative example, the duty cycle DUT is determined using an equation similar to the equation (24) except that the optimum disturbance F/F component Uopfd (the fifth term of the equation (24)) depending on the exhaust gas temperature Tgd is removed from the equation (24).

It can be seen from FIG. 13 that according to the present embodiment, since the duty cycle DUT includes the optimum disturbance F/F component Uopfd depending on the exhaust gas temperature Tgd, a range of variations of the element temperature TO2 due to changes in the exhaust gas temperature Tgd is reduced.

A second embodiment of the present invention will be described below with reference to FIG. 14. The second embodiment is partly different in arrangement or function from the first embodiment described above, and those structural or functional parts of the second embodiment which are identical to those of the first embodiment are denoted by identical reference characters, and will not be described in detail below.

Figure 14:
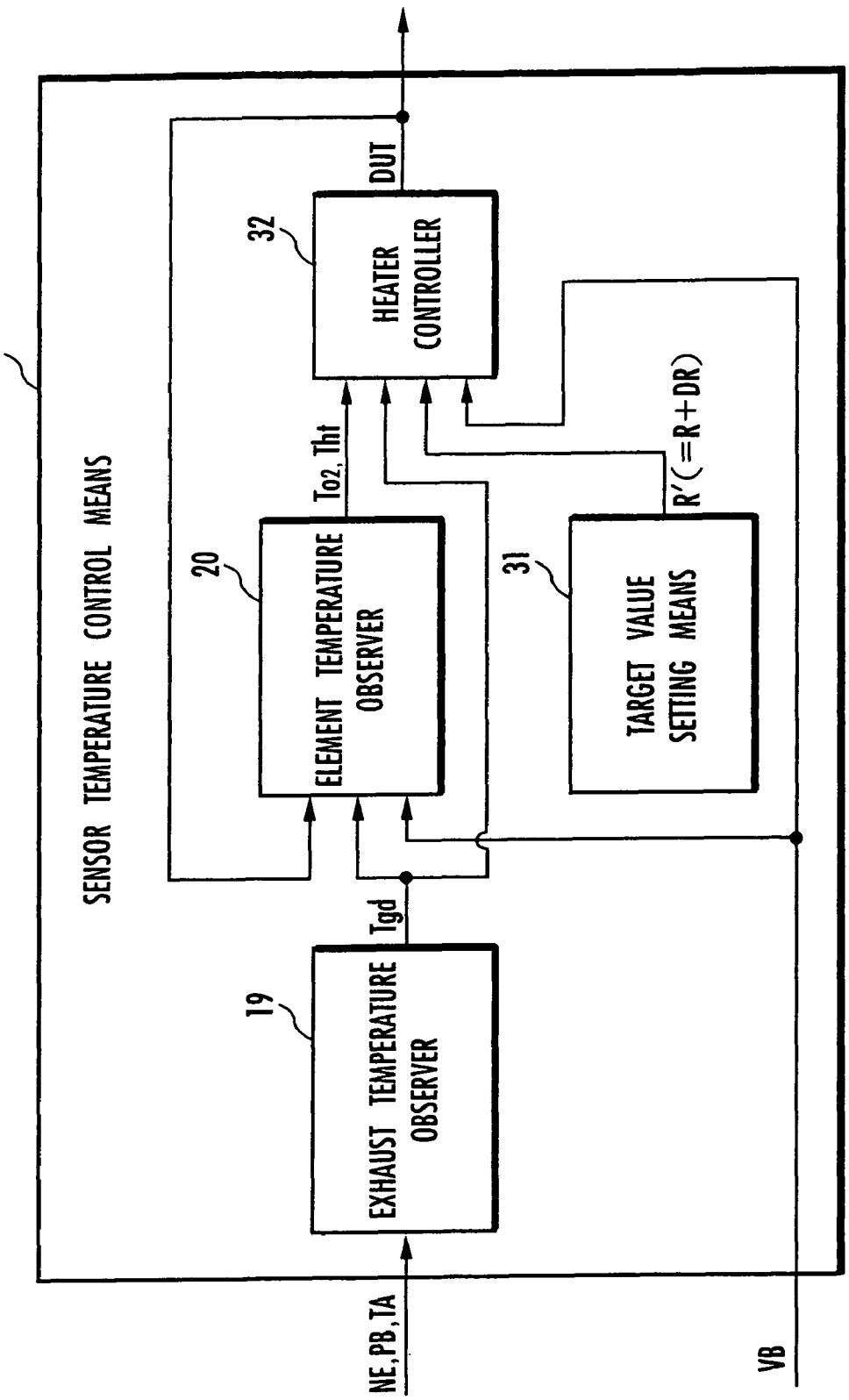
FIG. 14 is a block diagram showing a functional arrangement of a sensor temperature control means in an apparatus according to a second embodiment of the present invention.

According to the present embodiment, as shown in the block diagram of FIG. 14, the sensor temperature control means 18 of the control unit 16 shown in FIG. 1 comprises, as functional means, an exhaust temperature observer 19, an element temperature observer 20, a target value setting means 31, and a heater controller 32. The exhaust temperature observer 19 and the element temperature observer 20 are identical to those of the first embodiment. In the present embodiment, the target value setting means 31 and the heater controller 32 have their processing periods identical to the processing periods of the target value setting means 21 and the heater controller 22 according the first embodiment.

The target value setting means 31 serves to set a target value R' for the heater temperature Tht of the O2 sensor 8. According to the inventors' knowledge, the heater temperature Tht is relatively highly correlated to the element temperature TO2 and tends to be higher than the element temperature TO2 by a constant temperature in a steady state. According to the present embodiment, the target value setting means 31 sets, as the target value R' for the heater temperature Tht, a value R+DR which is higher than the target value R for the element temperature TO2 that is set as described in the first embodiment (the target value R set by the processing sequence shown in FIG. 9), by a predetermined value DR (e.g., 100° C.). As with the first embodiment, the target value R' that is set by the target value setting means 31 in each cycle time of its processing sequence is a target value after the target value predicting time Mr, and the target value R' in the period of the target value predicting time Mr is sequentially updated and stored.

The heater controller 32 sequentially generates the duty cycle DUT as a control input in order to keep the heater temperature Tht at the target value R'. In the present embodiment, as with the first embodiment, the heater controller 32 calculates a basic duty cycle SDUT according to an optimum predictive control algorithm, and corrects the basic duty cycle SDUT depending on the battery voltage VB according to the equation (25) thereby to generate the duty cycle DUT.

More specifically, according to the present embodiment, attention is paid to the difference e' between the heater temperature Tht and a target value R' therefor, a change Δe' per given time in the difference e' (corresponding to a rate of change of the difference e'), and a change ΔTO2 per given time in the element temperature TO2 (corresponding to a rate of change of the element temperature TO2), and a model equation for an object to be controlled by the heater controller 32 is introduced using the above differences and changes as state quantities relative to the object to be controlled by the heater controller 32.

If the difference e' (hereinafter referred to as "heater temperature difference e'") is defined as e'(n)=Tht(n)−R'(n), then the model equation is given as the following equation (26) based on the above equations (11-1), (11-2) according to the same idea as with the first embodiment:

$$X1(n+1) = \quad (26)$$

$$\Phi' \cdot X1(n) + G' \cdot \Delta SDUT(n) + Gd' \cdot \Delta Tgd(n) + Gr' \cdot R1(n+1)$$

where $$X1(n) = (e'(n), \Delta e'(n), \Delta T_{o2}(n))^T,$$

$$R1(n+1) = (\Delta R'(n+1), \Delta R'(n))^T,$$

$$G' = (0, Dx \cdot dtc, 0)^T,$$

$$Gd' = (0, 0Ax \cdot dtc)^T,$$

$$\Phi = \begin{bmatrix} 1 & 1 & 0 \\ 0 & 1 - Cx \cdot dtc - Fx \cdot dtc & Cx \cdot dtc \\ 0 & Bx \cdot dtc & 1 - Ax \cdot dtc - Bx \cdot dtc - Ex \cdot dtc \end{bmatrix}$$

$$Gr' = \begin{bmatrix} 0 & 0 \\ -1 & 1 - Cx \cdot dtc - Fx \cdot dtc \\ 0 & Bx \cdot dtc \end{bmatrix}$$

In the present embodiment, the basic control input SDUT (a control input at the time the battery voltage VB is equal to the reference value NVB) to be determined by the heater controller 22 is given by the equation (28) shown below as having integrated ΔSDUT (a control input on the model according to the equation (26)) which minimizes an evaluating function J1 according to the following equation (27):

$$J1 = \sum_{n=M+1}^{\infty} \begin{bmatrix} X1^T(n) \cdot Q0 \cdot X1(n) + \Delta SDUT^T(n) \cdot \\ H0 \cdot \Delta SDUT(n) \end{bmatrix} \quad (27)$$

where $$M = \max(Mr, Md)$$

$$SDUT(n) = Fs1 \cdot \sum_{j=1}^{n} e'(j) + Fe1 \cdot e'(n) + \quad (28)$$

$$Fx1 \cdot T_{02}(n) + \sum_{i=0}^{Mr} [Fr'(i) \cdot R'(n+i)] + Fdt' \cdot Tgd(n)$$

The coefficients Fs1, Fe1, Fx1 in the first through third terms, the coefficient Fr'(i) (i=0, 1, . . . , Mr) in the fourth term, and the coefficient Fdt' in the fifth term on the right side of the equation (28) are coefficients given respectively by the following equations (29-1) through (29-3):

$$F1 \equiv (Fs1, Fe1, Fx1) \quad (29\text{-}1)$$
$$= -[H0 + G'^T \cdot P' \cdot G']^{-1} \cdot G'^T \cdot P' \cdot \Phi'$$

$$Fr'(i) = \begin{cases} Fr12(1): & i = 0 \\ Fr11(i) + Fr12(i+1): & i = 1, 2, \ldots, Mr-1 \\ Fr11(Mr): & i = Mr \end{cases} \quad (29\text{-}2)$$

$$Fdt' = \sum_{i=0}^{Md} \{ -[H0 + G'^T \cdot P' \cdot G']^{-1} \cdot G'^T \cdot (\zeta^T)^i \cdot P' \cdot Gd' \} \quad (29\text{-}3)$$

where $$P' = $$
$$Q0 + \Phi'^T \cdot P' \cdot \Phi' - \Phi'^T \cdot P' \cdot G'[H0 + G'^T \cdot P' \cdot G']^{-1} \cdot G'^T \cdot P' \cdot \Phi'$$

$$\zeta' = \Phi' + G' \cdot F1$$

$$(Fr11(i), Fr12(i))$$
$$= -[H0 + G'^T \cdot P' \cdot G']^{-1} G'^T \cdot (\zeta^T)^{i-1} \cdot P' \cdot Gr'$$
$$(i = 1, 2, \ldots, Mr)$$

In the present embodiment, the weighted matrixes Q0, H0 with respect to the evaluating function J1, the target value predicting time Mr, and the exhaust gas temperature predicting time Md are identical to those in the first embodiment. However, they may be set to values different from those in the first embodiment. The coefficients Fs1, Fe1, Fx1, Fr'(i), Fdt' in the equation (28) may not necessarily be of the values according to the defining equations (29-1) through (29-3), but may be of values adjusted by way of simulation or experimentation. Furthermore, the coefficients Fs1, Fe1, Fx1, Fr'(i), Fdt' may be changed depending on the element temperature, the heater temperature, etc. In the present embodiment, as with the first embodiment, the exhaust gas temperature Tgd is maintained at the pre-sent value in the future until after Md steps. However, if Tgd at each time in the future can be detected or estimated, then the control input DUT may be determined using those values (in this case, Fdt' is a vector).

The above equation (28) is a formula for sequentially calculating a basic control input SDUT(n) with which the heater controller 32 controls the heater 13 in the present embodiment. Specifically, the heater controller 32 sequentially calculates the basic control input SDUT(n) in each cycle time (period) of the control processing of the heater controller 32 according to the equation (28), and corrects the basic control input SDUT(n) depending on the battery voltage VB according to the equation (25), thereby determining the duty cycle DUT(n). The terms on the right side of the equation (28) have the same meanings as those in the first embodiment. Specifically, the first through third terms (the term including Σe'(j) through the term including $T_{O2}(n)$) on the right side represent a control input component (a feedback component based on an optimum control algorithm) depending on the heater temperature difference e' and the element temperature $T_{O2}$. More specifically, the first and second terms represent a control input component depending on the heater temperature difference e', and the third term represents a control input component depending on the element temperature $T_{O2}$. The fourth term (the term of ΣFr'(i)·R'(n+1)) on the right side of the equation (28) and the fifth term (the term including Tgd(n)) on the right side thereof represent control input components (feed-forward components based on a predictive control algorithm) depending on the target value R and the exhaust gas temperature Tgd, respectively.

As the element temperature TO2 and the exhaust gas temperature Tgd which are required to determine the basic control input SDUT(n) according to the equation (28), there are employed, respectively, the latest value of the estimated value of the element temperature TO2 determined by the element temperature observer 20 and the latest value of the estimated value of the exhaust gas temperature Tgd determined by the exhaust temperature observer 19.

The heater temperature difference e' required for the calculation according to the equation (28) is calculated from the latest value of the estimated value of the heater temperature Tht determined by the element temperature observer 20 and the target value R' that has been set in a cycle time before the target value predicting time Mr by the target value setting means 31.

The other processing details than those described above are identical to those according to the first embodiment. In the present embodiment, the electric power supplied to the heater 13 of the O2 sensor 8 is controlled in order to maintain the heater temperature Tht of the O2 sensor 8 at the target value R'. In this case, except immediately after the engine 1 starts to operate or when the atmospheric temperature TA is considerably low (TA<0° C.), the target value R' is usually set to a temperature (900° C.) which is higher than a preferred target temperature of 800° C. for the active element 10 by a predetermined value DR (100° C. in the present embodiment). As a result, the temperature TO2 of the active element 10 of the O2 sensor 8 is indirectly controlled substantially at the temperature of 800° C. Therefore, as with the first embodiment, the output characteristics of the O2 sensor 8 can stably be kept as characteristics suitable for controlling the air-fuel ratio of the engine 1 (for controlling the air-fuel ratio to keep a good purifying capability of the catalytic converter 4), and hence the air-fuel ratio is controlled well to reliably keep a good purifying capability of the catalytic converter 4. During a predetermined period of time immediately after the engine 1 has started to operate, the target temperature R' for the heater 13 is set to a temperature (700° C.) which is higher than a low temperature (600° C.) as the target temperature R for the active element 10 than the predetermined value DR, for thereby preventing the active element 10 from being damaged by stresses due to abrupt heating. If the atmospheric temperature TA is low (TA<0° C.), then inasmuch as the target value R for the active element 10 is set to a value in the range of 750° C.≦R<800° C., the target value R' for the heater 13 is set to a value in the range of 850° C.≦R'<900° C. to prevent the heater 13 from being overheated.

According to the present embodiment, the duty cycle DUT as a control input to the heater 13 includes the control input component (the first term (the term including $\Sigma e'(j)$) and the second term (the term including e'(n)) of the equation (28)) depending on the difference between the estimated value of the heater temperature Tht an the target temperature R', and the control input component (the third term of the equation (28)) depending on the estimated value of the element temperature TO2, as feedback components. In addition, according to the present embodiment, a predictive control algorithm is also applied, and the duty cycle DUT includes the control input component (a feed-forward component of the fifth term on the right side of the equation (28)) depending on the exhaust gas temperature Tgd, and the control input component (a feed-forward component of the fourth term on the right side of the equation (28)) depending on the target value R'. As a result, the present embodiment provides the same operation and advantages as with the first embodiment. Thus, the heater temperature Tht can reliably be controlled stably at the desired target value R', and the element temperature TO2 can be controlled stably at a desired temperature.

A third embodiment of the present invention will be described below. The present embodiment is different from the first embodiment only as to the processing of the heater controller (specifically, the processing in STEP5-4 shown in FIG. 10), and those structural or functional parts of the third embodiment which are identical to those of the first embodiment are denoted by identical figures and reference characters, and will not be described in detail below.

According to the present embodiment, the heater controller 22 sequentially generates DUT as a control input according to an optimum predictive control algorithm, using the difference e (element temperature difference e) between the element temperature TO2 and the target value R, the element temperature TO2, and the heater temperature Tht as state quantities to be controlled. An algorithm of the processing sequence of the heater controller 22 is constructed as follows: The equations (11-1), (11-2) are brought together, providing the following equations (30-1), (30-2):

$$Xz(k+1) = Az \cdot Xz(k) + Bz \cdot \Delta SDUT(k) + Ez \cdot \Delta Tgd(k) \qquad (30\text{-}1)$$

$$\Delta T_{O2}(k) = Cz \cdot Xz(k) \qquad (30\text{-}2)$$

where $$Xz(k) = (\Delta T_{O2}(k), Tht(k))^T$$

$$Az = \begin{bmatrix} 1 - Ax \cdot dt - Bx \cdot dt - Ex \cdot dt & Bx \cdot dt \\ Cx \cdot dt & 1 - Cx \cdot dt - Fx \cdot dt \end{bmatrix}$$

$$Bx = (0, Dx \cdot dt)^T$$

$$Ez = (Ax \cdot dt, 0)^T$$

$$Cz = (1, 0)$$

From the equations (30-1), (30-2), there is obtained the following equation (31):

$$\begin{aligned}\Delta T_{O2}(k) &= Cz \cdot Xz(k+1) \\ &= Cz \cdot Az \cdot Xz(k) + Cz \cdot Bz \cdot \Delta SDUT(k) + \\ &\quad Cz \cdot Ez \cdot \Delta Tgd(k)\end{aligned} \qquad (31)$$

The equation (31) is the same as the equation (11-2), and is produced by rewriting the equation (11-2) using the matrix Az and the vectors Bz, Ez, Cz defined by the definition clauses of the equations (22-1), (22-2).

In the present embodiment, a change (difference) $\Delta e$ per each given time in the element temperature difference e defined by the equation (12) is defined by $\Delta e(k+1) = e(k+1) - e(k)$. The following equation (32) is obtained from this definition formula and the equation (31):

$$\begin{aligned}e(k+1) &= e(k) + \Delta e(k+1) \\ &= e(k) + (\Delta T_{O2}(k+1) - \Delta R(k+1)) \\ &= e(k) + Cz \cdot Az \cdot Xz(k) + Cz \cdot Bz \cdot \Delta SDUT(k) + \\ &\quad Cz \cdot Ez \cdot \Delta Tgd(k) - \Delta R(k+1)\end{aligned} \qquad (32)$$

The equation (32) and the above equation (30-1) are put together, providing the following equation (33):

$$X2(k+1) = \phi2 \cdot X2(k) + G2 \cdot \Delta SDUT(k) + Gd2 \cdot \Delta Tgd(k) + Gr2 \cdot \Delta R(k+1) \quad (33)$$

where $X2(k) = (e(k), T_{O2}(k), Tht(k))^T$ $$\Phi 2 = \begin{bmatrix} 1 & 1 - Ax \cdot dt - Bx \cdot dt - Ex \cdot dt & Bx \cdot dt \\ 0 & 1 - Ax \cdot dt - Bx \cdot dt - Ex \cdot dt & Bx \cdot dt \\ 0 & Cx \cdot dt & 1 - Cx \cdot dt - Fx \cdot dt \end{bmatrix}$$

$G2 = (0, 0, Dx \cdot dt)^T$ $Gd2 = (Ax \cdot dt, Ax \cdot dt, 0)^T$ $Gr2 = (-1, 0, 0)^T$ The equation (33) is a basic formula of the model to be controlled by the heater controller 22 according to the present embodiment. In this model to be controlled, the state quantity to be controlled is a state quantity vector $X2(k)=(e(k), \Delta T_{O2}(k), \Delta Tht(k))^T$ comprising the element temperature difference e, the change $\Delta T_{O2}$ per given time in the element temperature $T_{O2}$, and the change $\Delta Tht$ per given time in the heater temperature Tht.

In the present embodiment, for the reasons which are the same as with the first embodiment, the cycle time of the cycle time of the processing sequence of the heater controller 22 is longer than the period of the processing sequence of the element temperature observer 20 and the exhaust temperature observer 19. Consequently, the equation of the model to be controlled which is actually used in the present embodiment is the following equation (34) using the period dtc of the processing sequence of the heater controller 22 and the ordinal number n of the processing period thereof:

$$X2(n+1) = \phi2 \cdot X2(n) + G2 \cdot \Delta SDUT(n) + Gd2 \cdot \Delta Tgd(n) + Gr2 \cdot \Delta R(n+1) \quad (34)$$

where $X2(n) = (e(n), T_{O2}(n), Tht(n))^T$ $$\Phi 2 = \begin{bmatrix} 1 & 1 - Ax \cdot dtc - Bx \cdot dtc - Ex \cdot dtc & Bx \cdot dtc \\ 0 & 1 - Ax \cdot dtc - Bx \cdot dtc - Ex \cdot dtc & Bx \cdot dtc \\ 0 & Cx \cdot dtc & 1 - Cx \cdot dtc - Fx \cdot dtc \end{bmatrix}$$

$G2 = (0, 0, Dx \cdot dtc)^T$ $Gd2 = (Ax \cdot dtc, Ax \cdot dtc, 0)^T$ $Gr2 = (-1, 0, 0)^T$ The basic control input SDUT (a control input at the time the battery voltage VB is equal to the reference value NVB) to be determined by the heater controller 22 according to the optimum predictive control algorithm based on the model equation (34) is given by the equation (36) shown below as having integrated $\Delta SDUT$ (a control input on the model according to the equation (34)) which minimizes an evaluating function J2 according to the following equation (35):

$$J2 = \sum_{n=M+1}^{\infty} \left[ X2^T(n) \cdot Q0 \cdot X2(n) + \Delta SDUT^T(n) \cdot H0 \cdot \Delta SDUT(n) \right] \quad (35)$$

where $M = \max(Mr, Md)$

-continued $$SDUT(n) = Fs2 + \sum_{j=1}^{n} e(j) + Fx2 \cdot T_{O2}(n) + Fx3 \cdot Tht(n) + \sum_{i=1}^{Mr} [Fr2(i) \cdot R(n+I)] + Fdt2 \cdot Tgd(n) \quad (36)$$

The coefficients Fs2, Fx2, Fx3 in the first through third terms, the coefficient $Fr2(i)$ ($i=0, 1, \ldots, Mr$) in the fourth term, and the coefficient Fdt2 in the fifth term on the right side of the equation (36) are coefficients given respectively by the following equations (37-1) through (37-3):

$$F2 \equiv (Fs2, Fx2, Fx3) \quad (37\text{-}1)$$
$$= -[H0 + G2^T \cdot P2 \cdot G2]^{-1} \cdot G2^T \cdot P2 \cdot \Phi 2$$

$$Fr2(i) = \frac{-[H0 + G2^T \cdot P2 \cdot G2]^{-1} \cdot}{G2^T \cdot (\zeta 2^T)^{i-1} \cdot P2 \cdot Gr2} \quad (37\text{-}2)$$

$(i = 1, 2, \ldots, Mr)$ $$Fdt2 = \sum_{i=0}^{Md} \left\{ \begin{array}{l} -[H0 + G2^T \cdot P2 \cdot G2]^{-1} \cdot \\ G2^T \cdot (\zeta 2^T)^i \cdot P2 \cdot Gd2 \end{array} \right\} \quad (37\text{-}3)$$

where $P2 = Q0 + \Phi 2^T \cdot P2 \cdot \Phi 2 - \Phi 2 \cdot P2 \cdot G2 \cdot [H0 + G2^T \cdot P2 \cdot G2]^{-1} \cdot G2^T \cdot P2 \cdot \Phi 2$ $\zeta 2 = \Phi 2 + G2 \cdot F2$ In the present embodiment, the weighted matrixes Q0, H0 with respect to the evaluating function J2, the target value predicting time Mr, and the exhaust gas temperature predicting time Md are identical to those in the first embodiment. However, they may be set to values different from those in the first embodiment. The coefficients Fs2, Fx2, Fx3, Fr2(i), Fdt2 in the equation (36) may not necessarily be of the values according to the defining equations (37-1) through (37-3), but may be of values adjusted by way of simulation or experimentation. Furthermore, the coefficients Fs2, Fx2, Fx3, Fr2 (i), Fdt2 may be changed depending on the element temperature, the heater temperature, etc. In the present embodiment, as with the first embodiment, the exhaust gas temperature Tgd is maintained at the present value in the future until after Md steps. However, if Tgd at each time in the future can be detected or estimated, then the control input DUT may be determined using those values (in this case, Fdt2 is a vector).

The above equation (36) is a formula for sequentially calculating a basic control input SDUT(n) with which the heater controller 22 controls the heater 13 in the present embodiment. Specifically, the heater controller 22 sequentially calculates the basic control input SDUT(n) in each cycle time (period) of the control processing of the heater controller 22 according to the equation (36), and corrects the basic control input SDUT(n) depending on the battery voltage VB according to the equation (25), thereby determining the duty cycle DUT(n), as with the first embodiment. The first through third terms (the term including $\Sigma e(j)$ through the term including Tht(n)) on the right side of the equation (36) represent a control input component (a feedback component based on an optimum control algorithm) depending on the heater temperature difference e, the element temperature $T_{O2}$, and the heater temperature Tht. More specifically, the first term represents a control input component depending on the heater temperature difference e, the second term represents a control input component depending on the element temperature $T_{O2}$, and the third term represents a control input component depending on the heater temperature Tht. The fourth term (the term of $\Sigma Fr2(i) \cdot R(n+i)$) on the right side of the equation (36) and the fifth term (the term including Tgd(n)) on the right side thereof represent control input components (feed-forward components based on a predictive control algorithm) depending on the target value R and the exhaust gas temperature Tgd, respectively.

As the element temperature $T_{O2}$ and the heater temperature Tht which are required to determine the basic control input SDUT(n) according to the equation (36), there are employed, respectively, the latest value of the estimated value of the element temperature $T_{O2}$ determined by the element temperature observer 20 and the latest value of the estimated value of the heater temperature Tht. As the exhaust gas temperature Tgd in the equation (36), there is employed the latest value of the estimated value of the exhaust gas temperature Tgd determined by the exhaust temperature observer 19.

The heater temperature difference e required for the calculation according to the equation (36) is calculated from the latest value of the estimated value of the element temperature $T_{O2}$ determined by the element temperature observer 20 and the target value R(n) that has been set in a cycle time before the target value predicting time Mr by the target value setting means 21. The fourth term on the right side of the equation (36) is calculated using time-series data R(n+1), R(n+2), . . . , R(n+Mr) of the target value R which have been set from a cycle time which is one cycle time after the cycle time before the target value predicting time Mr to the present time by the target value setting means 21.

The other processing details than those described above are identical to those according to the first embodiment. More specifically, in the present embodiment, the heater controller 22 determines DUT(n) according to the equations (36), (37) in STEP5-4 shown in FIG. 10. The other processing details than the processing in STEP5-4 are exactly the same as those according to the first embodiment. In the present embodiment, as with the first embodiment, the element temperature $T_{O2}$ is controlled at the target value R. In this case, the basic control input SDUT does not include an input component that is directly proportional to the element temperature difference e, but includes a component (the second term of the equation (36)) depending on the element temperature $T_{O2}$, unlike the first embodiment. Therefore, immediately after the engine 1 starts to operate or when the target value R is changed by the target value setting means 21 from a low-temperature target value (600° C.) to a high-temperature target value (750° C. through 800° C.), as the element temperature $T_{O2}$ approaches the target value R, the element temperature $T_{O2}$ is effectively prevented from overshooting with respect to the target value R. The advantages produced by the basic control input SDUT and the duty cycle DUT which include input components depending on the heater temperature Tht, the target value R, and the exhaust gas temperature Tgd are the same as those according to the first embodiment.

A fourth embodiment of the present invention will be described below. The present embodiment is different from the second embodiment only as to the processing of the heater controller, and those structural or functional parts of the fourth embodiment which are identical to those of the second embodiment (including those of the first embodiment which are incorporated in the second embodiment) are denoted by identical figures and reference characters, and will not be described in detail below.

The present embodiment is different from the second embodiment only as to the processing sequence of the heater controller 32 (FIG. 14) described in the second embodiment, and determines the duty cycle DUT according to an optimum predictive control algorithm in the form described in the third embodiment. According to the present embodiment, specifically, the state quantity of an object to be controlled by the heater controller 32 is a state quantity vector $X3(n)=(e'(n), \Delta TO2(n), \Delta Tht(n))^T$ comprising the difference (heater temperature difference) e' between the heater temperature Tht and the target value R', a change $\Delta TO2$ per given time in the element temperature TO2, and a change $\Delta Tht$ per given time in the heater temperature Tht. That is, the state quantity of the object to be controlled uses the heater temperature difference e'(n), rather than the heater temperature difference e(n) of the state quantity vector $X2(n)=(e(n), \Delta TO2(n), \Delta Tht(n))^T$ in the third embodiment. If a change $\Delta e'$ per given time in the heater temperature difference e' is redefined as $\Delta e'(n+1)=e'(n+1)-e'(n)$, then a model to be controlled is expressed by the following equation (38) according to the same concept as with the third embodiment:

$$X3(n+1) = \qquad (38)$$
$$\phi 3 \cdot X3(n) + G3 \cdot \Delta SDUT(n) + Gd3 \cdot \Delta Tgd(n) + Gr3 \cdot \Delta R'(n+1)$$

where $X3(n) = (e'(n), T_{O2}(n), Tht(n))^T$ $$\Phi 3 = \begin{bmatrix} 1 & Cx \cdot dtc & 1 - Cx \cdot dtc - Fx \cdot dtc \\ 0 & 1 - Ax \cdot dtc - Bx \cdot dtc - Ex \cdot dtc & Bx \cdot dtc \\ 0 & Cx \cdot dtc & 1 - Cx \cdot dtc - Fx \cdot dtc \end{bmatrix}$$

$G3 = (Dx \cdot dtc, 0, Dx \cdot dtc)^T$ $Gd3 = (0, Ax \cdot dtc, 0)^T$ $Gr3 = (-1, 0, 0)^T$ The basic control input SDUT (a control input at the time the battery voltage VB is equal to the reference value NVB) to be determined by the heater controller 32 according to the present embodiment is given by the equation (40) shown below as having integrated $\Delta SDUT$ (a control input on the model according to the equation (38)) which minimizes an evaluating function J3 according to the following equation (39):

$$J3 = \sum_{n=M+1}^{\infty} \begin{bmatrix} X3^T(n) \cdot Q0 \cdot X3(n) + \Delta SDUT^T(n) \cdot \\ H0 \cdot \Delta SDUT(n) \end{bmatrix} \qquad (39)$$

where $M = \max(Mr, Md)$ $$SDUT(n) = Fs3 + \sum_{j=1}^{n} e'(j) + Fx4 \cdot T_{O2}(n) + \qquad (40)$$
$$Fx5 \cdot Tht(n) + \sum_{i=1}^{Mr} [Fr3(i) \cdot R'(n+i)] + Fdt3 \cdot Tgd(n)$$

The coefficients Fs3, Fx4, Fx5 in the first through third terms, the coefficient Fr3(i) (i=0, 1, . . . , Mr) in the fourth term, and the coefficient Fdt3 in the fifth term on the right side of the equation (40) are coefficients given respectively by the following equations (41-1) through (41-3):

$$F3 \equiv (Fs3, Fx4, Fx5) \qquad (41\text{-}1)$$
$$= -[H0 + G3^T \cdot P3 \cdot G3]^{-1} \cdot G3^T \cdot P3 \cdot \Phi 3$$

$$Fr3(i) = -[H0 + G3^T \cdot P3 \cdot G3]^{-1} \cdot G3^T \cdot (\zeta 3^T)^{i-1} \cdot P3 \cdot Gr3 \qquad (41\text{-}2)$$
$$(i = 1, 2, \ldots, Mr)$$

$$Fdt3 = \sum_{i=0}^{Md} \left\{ \begin{array}{l} -[H0 + G3^T \cdot P3 \cdot G3]^{-1} \cdot \\ G3^T \cdot (\zeta 3^T)^i \cdot P3 \cdot Gd3 \end{array} \right\} \qquad (41\text{-}3)$$

where
$$P3 = Q0 + \Phi 3^T \cdot P3 \cdot \Phi 3 -$$
$$\Phi 3 \cdot P3 \cdot G3 \cdot [H0 + G3^T \cdot P3 \cdot G3]^{-1} \cdot G3^T \cdot P3 \cdot \Phi 3$$
$$\zeta 3 = \Phi 3 + G3 \cdot F3$$

In the present embodiment, the weighted matrixes Q0, H0 with respect to the evaluating function J3, the target value predicting time Mr, and the exhaust gas temperature predicting time Md are identical to those in the first embodiment. However, they may be set to values different from those in the first embodiment. The coefficients Fs3, Fx4, Fx5, Fr3($i$), Fdt3 in the equation (40) may not necessarily be of the values according to the defining equations (41-1) through (41-3), but may be of values adjusted by way of simulation or experimentation. Furthermore, the coefficients Fs3, Fx4, Fx5, Fr3($i$), Fdt3 may be changed depending on the element temperature, the heater temperature, etc. In the present embodiment, as with the first embodiment, the exhaust gas temperature Tgd is maintained at the present value in the future until after Md steps. However, if Tgd at each time in the future can be detected or estimated, then the control input DUT may be determined using those values (in this case, Fdt3 is a vector).

The above equation (40) is a formula for sequentially calculating a basic control input SDUT(n) with which the heater controller 32 controls the heater 13 in the present embodiment. Specifically, the heater controller 32 sequentially calculates the basic control input SDUT(n) in each cycle time (period) of the control processing of the heater controller 32 according to the equation (40), and corrects the basic control input SDUT(n) depending on the battery voltage VB according to the equation (25), thereby determining the duty cycle DUT(n), as with the first embodiment. The first through third terms (the term including Σe'(j) through the term including Tht(n)) on the right side of the equation (40) represent a control input component (a feedback component based on an optimum control algorithm) depending on the heater temperature difference e', the element temperature $T_{O2}$, and the heater temperature Tht. More specifically the first term represents a control input component depending on the heater temperature difference e', the second term represents a control input component depending on the element temperature $T_{O2}$, and the third term represents a control input component depending on the heater temperature Tht. The fourth term (the term of ΣFr3($i$)·R'(n+i)) on the right side of the equation (40) and the fifth term (the term including Tgd(n)) on the right side thereof represent control input components (feed-forward components based on a predictive control algorithm) depending on the target value R' and the exhaust gas temperature Tgd, respectively.

As the element temperature $T_{O2}$ and the heater temperature Tht which are required to determine the basic control input SDUT(n) according to the equation (40), there are employed, respectively, the latest value of the estimated value of the element temperature $T_{O2}$ determined by the element temperature observer 20 and the latest value of the estimated value of the exhaust gas temperature Tgd determined by the exhaust temperature observer 19. The heater temperature difference e' required for the calculation according to the equation (40) is calculated from the latest value of the estimated value of the heater temperature Tht determined by the element temperature observer 20 and the target value R'(n) that has been set in a cycle time before the target value predicting time Mr by the target value setting means 31. The fourth term on the right side of the equation (40) is calculated using time-series data R'(n+1), R'(n+2), ..., R'(n+Mr) of the target value R' which have been set from a cycle time which is one cycle time after the cycle time before the target value predicting time Mr to the present time by the target value setting means 31.

The other processing details than those described above are identical to those according to the second embodiment. In the present embodiment, as with the second embodiment, the heater temperature Tht is controlled at the target value R', and the element temperature $T_{O2}$ is controlled at a temperature corresponding to the target value R'. In this case, the basic control input SDUT does not include an input component that is directly proportional to the element temperature difference e', but includes a component (the third term of the equation (40)) depending on the heater temperature Tht, unlike the second embodiment. Therefore, immediately after the engine 1 starts to operate or when the target value R' is changed by the target value setting means 31 from a low-temperature target value (700° C. in the present embodiment) to a high-temperature target value (850° C. through 900° C.), as the heater temperature Tht approaches the target value R', the heater temperature Tht is effectively prevented from overshooting with respect to the target value R'. The element temperature $T_{O2}$ is thus allowed to converge smoothly to a temperature corresponding to the target value R' for the heater temperature Tht. The advantages produced by the basic control input SDUT and the duty cycle DUT which include input components depending on the heater temperature $T_{O2}$, the target value R', and the exhaust gas temperature Tgd are the same as those according to the second embodiment.

In the first through fourth embodiments described above, the exhaust gas temperature Tgd is estimated. However, an exhaust gas sensor may be disposed in the vicinity of the O2 sensor 8, and the exhaust gas temperature Tgd may be detected by the exhaust gas sensor. Even if the exhaust gas sensor is disposed in a location remote from the O2 sensor 8, if the temperature detected by the exhaust gas sensor is substantially the same as the exhaust gas temperature Tgd near the O2 sensor 8 due to the layout of the exhaust system or the like, then the detected temperature may be substituted for the exhaust gas temperature Tgd near the O2 sensor 8. If the temperature detected by the exhaust gas sensor is used, then the temperature (the latest value) detected by the exhaust gas sensor is used as the value of the exhaust gas temperature Tgd in the equation (10-1) to estimate the element temperature TO2 and the heater temperature Tht. Furthermore, the temperature (the latest value) detected by the exhaust gas sensor is used as the value of the exhaust gas temperature Tgd in the equation (24), the equation (28), the equation (36), or the equation (40) to calculate the basic duty cycle SDUT and then calculate the duty cycle DUT according to the equation (25).

If the exhaust gas sensor is disposed in a location remote from the O2 sensor 8 and if the temperature detected by the exhaust gas sensor is not necessarily be same as the exhaust gas temperature Tgd near the O2 sensor 8, then it is possible to estimate the exhaust gas temperature Tgd near the O2 sensor 8 using the temperature detected by the exhaust gas sensor. For example, if an exhaust gas temperature sensor is provided which is capable of detecting the exhaust gas temperature Tgd in the partial exhaust passageway 3b, then the exhaust gas temperature Tgd near the O2 sensor 8 can be estimated by the calculations of the equations (8), (9) by using the detected temperature as the exhaust gas temperature Tgb in the equation (8-1). In this case, the calculations of the equations (1), (5), (6) are not required.

In the first and second embodiments, both the element temperature TO2 and the heater temperature Tht are estimated. However, either one of them may be detected directly by a temperature sensor. If the element temperature TO2 is detected, then the heater temperature Tht may be estimated using the detected value of the element temperature TO2 as the value of the element temperature TO2 in the equation (10-2). The duty cycle DUT may be calculated using the estimated value as the heater temperature Tht in the calculation of the equation (24), the equation (28), the equation (36), or the equation (40), and also using the detected value of the element temperature TO2 as the value of the element temperature TO2. If the heater temperature Tht is detected, then the element temperature TO2 may be estimated using the detected value of the heater temperature Tht as the value of the heater temperature Tht in the equation (10-1). The duty cycle DUT may be calculated using the estimated value as the element temperature TO2 in the calculation of the equation (24), the equation (28), the equation (36), or the equation (40), and also using the detected value of the heater temperature Tht as the value of the heater temperature Tht. If both the element temperature TO2 and the heater temperature Tht are detected by the temperature sensors, then the detected temperatures may be used as the values of the element temperature TO2 and the heater temperature Tht in the calculation of the equation (24), the equation (28), the equation (36), or the equation (40) to calculate the duty cycle DUT.

In the first and second embodiments, the element temperature TO2 of the O2 sensor 8 or the heater temperature Tht is controlled at the target value R or R' according to the optimum predictive control algorithm. However, the present invention is not limited to the optimum predictive control algorithm.

For example, the control input DUT may be determined according to an ordinary optimum control algorithm which includes no predictive control algorithm. In this case, the control input DUT may sequentially be calculated according to an equation which is produced by removing the fourth term (the term including R(n+i)) and the fifth term (the term including Tgd(n)) from the right side of the equation (24) or the equation (36) or by removing the fourth term (the term including R'(n+i)) and the fifth term (the term including Tgd(n)) from the right side of the equation (28) or the equation (40). According to this modification, the heater controller for determining the control input DUT is an optimum servocontroller for determining the control input DUT in order to minimize the value of the evaluating function J0 or J1 or J2 or J3 where M=0 in the equation (17), the equation (27), the equation (35) or the equation (39).

Alternatively, the control input DUT may calculated according to an equation which is produced by removing one or two of the third term (the component depending on the heater temperature Tht), the fourth term (the term including R(n+i)), and the fifth term (the term including Tgd(n)) from the right side of the equation (24). Further alternatively, the control input DUT may calculated according to an equation which is produced by removing one or two of the third term (the component depending on the element temperature TO2), the fourth term (the term including R'(n+i)), and the fifth term (the term including Tgd(n)) from the right side of the equation (28). Further alternatively, the control input DUT may calculated according to an equation which is produced by removing one or two of the third term (the component depending on the heater temperature Tht), the fourth term (the term including R(n+i)), and the fifth term (the term including Tgd(n)) from the right side of the equation (36). Further alternatively, the control input DUT may calculated according to an equation which is produced by removing one or two of the second term (the component depending on the element temperature TO2), the fourth term (the term including R'(n+i)), and the fifth term (the term including Tgd(n)) from the right side of the equation (40). The component depending on the element temperature difference e in the equation (24) or the equation (36) and the component depending on the heater temperature difference e' in the equation (28) or the equation (40) may be determined according to a PI control law or a PID control law.

In each of the embodiments described above, the element temperature TO2 of the O2 sensor 8 is controlled. However, the present invention is also applicable to an exhaust gas sensor other than the O2 sensor 8 (e.g., the wide-range air-fuel ratio sensor 9 or a humidity sensor for generating an output signal representative of the water content of the exhaust gas).

The internal combustion engine to which the present invention is applicable may be an ordinary port-injected internal combustion engine, a spark-ignition internal combustion engine with direct fuel injection into cylinders, a diesel engine, an internal combustion engine for use as an outboard engine on a boat, etc.

INDUSTRIAL APPLICABILITY

As described above, the present invention is useful as a technology for appropriately controlling the temperature of an exhaust gas sensor disposed in the exhaust system of an internal combustion engine mounted on an automobile, a hybrid vehicle, an outboard engine assembly, or the like, at a desirable temperature for stabilizing the output characteristics of the exhaust gas sensor.

The invention claimed is:

1. An apparatus for controlling the temperature of an exhaust gas sensor disposed in an exhaust passage of an internal combustion engine and having an active element for contacting an exhaust gas flowing through the exhaust passage and a heater for heating the active element, characterized by comprising:
    means for sequentially acquiring element temperature data representing the temperature of said active element, means for sequentially acquiring heater temperature data representing the temperature of said heater, and heater control means for sequentially generating a control input which defines an amount of heat generating energy supplied to said heater so as to equalize the temperature of the heater represented by said heater temperature data to a predetermined target temperature, and controlling the heater depending on the control input, characterized in that said control input generated by said heater control means includes at least an input component depending on the difference between the temperature of the heater represented by said heater temperature data and said target temperature, and an input component depending on the temperature of the active element represented by said element temperature data.

2. An apparatus for controlling the temperature of an exhaust gas sensor according to claim 1, characterized by comprising means for sequentially acquiring exhaust gas temperature data representing the temperature of said exhaust gas, and characterized in that said control input generated by said heater control means includes an input component depending on the temperature of the exhaust gas represented by said exhaust gas temperature data.

3. An apparatus for controlling the temperature of an exhaust gas sensor according to claim 1, characterized in that said control input generated by said heater control means includes an input component depending on said target temperature.

4. An apparatus for controlling the temperature of an exhaust gas sensor according to claim 1, characterized in that said control input generated by said heater control means includes an input component depending on the temperature of the heater represented by said heater temperature data.

5. A method of controlling the temperature of an exhaust gas sensor disposed in an exhaust passage of an internal combustion engine and having an active element for contacting an exhaust gas flowing through the exhaust passage and a heater for heating the active element, characterized by comprising the steps of:

sequentially acquiring element temperature data representing the temperature of said active element and heater temperature data representing the temperature of said heater, sequentially generating a control input which defines an amount of heat generating energy supplied to said heater so as to equalize the temperature of the heater represented by said heater temperature data to a predetermined target temperature, and controlling the heater depending on the control input, and characterized in that when said control input is generated, said control input is generated so as to include at least an input component depending on the difference between the temperature of the heater represented by said heater temperature data and said target temperature, and an input component depending on the temperature of the active element represented by said element temperature data.

6. A method of controlling the temperature of an exhaust gas sensor according to claim 5, further characterized by comprising the step of sequentially acquiring exhaust gas temperature data representing the temperature of said exhaust gas, wherein when said control input is generated, said control input is generated so as to further include an input component depending on the temperature of the exhaust gas represented by said exhaust gas temperature data.

7. A method of controlling the temperature of an exhaust gas sensor according to claim 5, characterized in that when said control input is generated, said control input is generated so as to further include an input component depending on said target temperature.

8. A method of controlling the temperature of an exhaust gas sensor according to claim 5, characterized in that said control input is generated, said control input is generated so as to further include an input component depending on the temperature of the heater represented by said heater temperature data.

9. A recording medium readable by a computer and storing a temperature control program for enabling the computer to perform a process of controlling the temperature of an active element of an exhaust gas sensor disposed in an exhaust passage of an internal combustion engine and having the active element for contacting an exhaust gas flowing through the exhaust passage and a heater for heating the active element, characterized in that said temperature control program includes a program for enabling said computer to perform a process of sequentially acquiring element temperature data representing the temperature of said active element and heater temperature data representing the temperature of said heater, a control input generating program for enabling said computer to perform a process of sequentially generating a control input which defines an amount of heat generating energy supplied to said heater so as to equalize the temperature of the heater represented by said heater temperature data to a predetermined target temperature, and a program for enabling said computer to perform a process of controlling the heater depending on the control input, wherein said control input generating program has an algorithm for enabling said computer to generate said control input so as to include at least an input component depending on the difference between the temperature of the heater represented by said heater temperature data and said target temperature, and an input component depending on the temperature of the active element represented by said element temperature data.

10. A recording medium storing a temperature control program for an exhaust gas sensor according to claim 9, characterized in that said temperature control program further includes a program for enabling said computer to perform a process of sequentially acquiring exhaust gas temperature data representing the temperature of said exhaust gas, wherein said control input generating program has an algorithm for enabling said computer to generate said control input so as to further include an input component depending on the temperature of the exhaust gas represented by said exhaust gas temperature data.

11. A recording medium storing a temperature control program for an exhaust gas sensor according to claim 9, characterized in that said control input generating program has an algorithm for enabling said computer to generate said control input so as to further include an input component depending on said target temperature.

12. A recording medium storing a temperature control program for an exhaust gas sensor according to claim 9, characterized in that said control input generating program has an algorithm for enabling said computer to generate said control input so as to further include an input component depending on the temperature of the heater represented by said heater temperature data.

* * * * *

UNITED STATES PATENT AND TRADEMARK OFFICE
CERTIFICATE OF CORRECTION

Page 1 of 1

PATENT NO. : 7,765,996 B2
APPLICATION NO. : 12/292612
DATED : August 3, 2010
INVENTOR(S) : Yuji Yasui and Yoshihisa Iwaki It is certified that error appears in the above-identified patent and that said Letters Patent is hereby corrected as shown below:

On the Front Page of the Patent, Section (62) Related U.S. Application Data should read:

--Division of application No. 10/517,139, filed as application No. PCT/JP03/03956 on March 28, 2003, now Pat. No. 7,490,596--

Signed and Sealed this
Twenty-fifth Day of January, 2011

David J. Kappos
*Director of the United States Patent and Trademark Office*